United States Patent
Park et al.

(10) Patent No.: US 12,404,249 B2
(45) Date of Patent: Sep. 2, 2025

(54) HETEROCYCLIC DERIVATIVES AND USE THEREOF

(71) Applicant: C&C RESEARCH LABORATORIES, Gyeonggi-do (KR)

(72) Inventors: Chan Hee Park, Gyeonggi-do (KR); Jun Hwan Im, Gyeonggi-do (KR); Soon Ok Lee, Gyeonggi-do (KR); Sang Hwi Lee, Gyeonggi-do (KR); Kwang Seok Ko, Gyeonggi-do (KR); Byung Ho Kim, Gyeonggi-do (KR); Hyung Jo Moon, Gyeonggi-do (KR); Jae Ill Kim, Gyeonggi-do (KR); Heon Kyu Park, Gyeonggi-do (KR); Yeon Ju Hong, Gyeonggi-do (KR)

(73) Assignee: C&C RESEARCH LABORATORIES, Gyeonggi-do (KR)

( * ) Notice: Subject to any disclaimer, the term of this patent is extended or adjusted under 35 U.S.C. 154(b) by 0 days.

(21) Appl. No.: 17/058,209

(22) PCT Filed: May 31, 2019

(86) PCT No.: PCT/KR2019/006554
§ 371 (c)(1),
(2) Date: Nov. 24, 2020

(87) PCT Pub. No.: WO2019/231271
PCT Pub. Date: Dec. 5, 2019

(65) Prior Publication Data
US 2021/0155594 A1 May 27, 2021

(30) Foreign Application Priority Data

May 31, 2018 (KR) .................. 10-2018-0062450

(51) Int. Cl.
*C07D 239/72* (2006.01)
*C07D 215/38* (2006.01)
*C07D 215/48* (2006.01)
*C07D 473/34* (2006.01)

(52) U.S. Cl.
CPC ......... *C07D 239/72* (2013.01); *C07D 215/38* (2013.01); *C07D 215/48* (2013.01); *C07D 473/34* (2013.01)

(58) Field of Classification Search
CPC .. C07D 239/72; C07D 215/38; C07D 215/48; C07D 473/34
See application file for complete search history.

(56) References Cited

U.S. PATENT DOCUMENTS 7,601,836 B2 * 10/2009 Pitts ................ A61K 31/517
544/279
2006/0074105 A1 * 4/2006 Ware, Jr. ............ C07D 401/12
546/159
2009/0004185 A1 * 1/2009 Venkatesan ......... C07D 403/12
514/266.4
2010/0234324 A1 9/2010 Eggenweiler et al.
2011/0172429 A1 7/2011 Asai et al.

FOREIGN PATENT DOCUMENTS

| JP | 2008-513413 A | 5/2008 |
| JP | 2009-502801 A | 1/2009 |
| JP | 2009-523845 A | 6/2009 |
| JP | 2011-513322 A | 4/2011 |
| JP | 2012-503664 A | 2/2012 |
| WO | WO-1996/006084 A1 | 2/1996 |
| WO | WO-2001/081345 A1 | 11/2001 |
| WO | WO-2005/061516 A1 | 7/2005 |
| WO | WO-2006/030031 A1 | 3/2006 |
| WO | WO-2007/013964 A1 | 2/2007 |
| WO | WO-2007/083978 A1 | 7/2007 |
| WO | WO-2008/086462 A2 | 7/2008 |
| WO | WO-2009/007422 A1 | 1/2009 |
| WO | WO-2009/108670 A1 | 9/2009 |
| WO | WO-2010/036629 A2 | 4/2010 |
| WO | WO-2010/036632 A1 | 4/2010 |
| WO | WO-2010/093419 A1 | 8/2010 |
| WO | WO-2012/079079 A1 | 6/2012 |
| WO | WO-2014/145512 A2 | 9/2014 |
| WO | WO-2019/046778 A1 | 3/2019 |

OTHER PUBLICATIONS

Cancer and Metastasis Reviews (1998), 17(1), 91-106.*
Science (1999), vol. 286, 531-537.*
Registry No. 1647716-82-2, File Registry on STN, Feb. 15, 2015.*
Registry No. 1291764-19-6, File Registry on STN, May 8, 2011.*
Registry No. 1191438-67-1, file Registry on STN, entered STN Nov. 6, 2009.*
Registry No. 1305730-95-3, file Registry on STN, entered STN Jun. 5, 2011.*
Registry No. 479072-23-6, File Registry on STN, entered STN: Jan. 15, 2003.*
Registry No. 1039736-54-3, file Registry on STN, entered STN Aug. 10, 2008.*
International Search Report from corresponding PCT Application No. PCT/KR2019/006554, dated Sep. 3, 2019.
Akira et al., Cell, 1994, 76.
Akira et al., Oncogene 2000, 19.
Becker S et al., Nature, 1998, 394.
Benekli et al., Blood, 2002, 99.
Chen X et al., Cell, 1998, 93.
Coleman et al., J. Med. Chem., 2005, 48.

(Continued)

*Primary Examiner* — Rebecca L Anderson
(74) *Attorney, Agent, or Firm* — Harness, Dickey & Pierce, P.L.C.

(57) ABSTRACT

The present invention relates to novel heterocyclic compounds useful in preparing drugs for the prevention or treatment of diseases associated with STAT3 protein. Specifically, these drugs are useful in the prevention or treatment of solid tumors, blood cancers, radiation or drug-resistant cancers, metastatic cancers, inflammatory diseases, immune system diseases, diabetes, macular degeneration, papillomavirus infections and tuberculosis.

17 Claims, No Drawings

(56) References Cited

OTHER PUBLICATIONS

D. Neculai et al., J. Biol. Chem., 2005, 280.
Ho AS et al., Proc. Natl. Acad. Sci., 1993, 90.
Levy et al., Nat. Rev. Mol. Cell Biol., 2002, 3.
LLL-12 (Lin et al., Neoplasia, 2010, 12).
Masuda et al., Cancer Res., 2002, 62.
Novick D et al., Cell, 1994, 77.
S3I1-M2001 (Siddiquee et al., Chem. Biol., 2007, 2).
Schindler C et al., Annu. Rev. Biochem., 1995, 64.
SF-1-066 (Zhang et al., Biochem. Pharm., 2010, 79).
Siddiquee et al., Proc. Natl. Acad. Sci., 2007, 104).
STA-21 (Song et al., Proc. Natl. Acad. Sci., 2005, 102).
Stark et al., Annu. Rev. Biochem., 1998, 67.
Stattic (Schust et al., Chem. Biol. 2006, 13).
STX-0119 (Matsuno et al., ACS Med. Chem. Lett., 2010, 1).
Turkson J et al., Mol Cancer Ther. 2004, 261.
Valeria Poli et al., Review, Landes Bioscience, 2009.
Vinkemeier U et al., Science, 1998, 279.
Yuichi et al., Int. J. Oncology, 2007, 30.
Zhong et al., Science, 1994, 264.
Extended European Search Report from corresponding European Patent Application No. 19812552.8, dated Mar. 13, 2022.
Acta Poloniae Pharmaceutica, 1984, vol. 41, pp. 161-165.
STN Registry 1970292-07-9, Aug. 10, 2016.
STN Registry 1972027-76-1, Aug. 12, 2016.
STN Registry 1920445-10-8, May 29, 2016.
STN Registry 1183216-02-5, Sep. 13, 2009.
STN Registry 1183089-50-0, Sep. 13, 2009.

* cited by examiner

HETEROCYCLIC DERIVATIVES AND USE THEREOF

CROSS-REFERENCE TO RELATED APPLICATIONS

This application is a national phase application of PCT Application No. PCT/KR2019/006554, filed on May 31, 2019, which claims benefit of Korean Patent Application No. 10-2018-0062450, filed May 31, 2018.

TECHNICAL FIELD

The present invention relates to novel heterocyclic compounds, uses thereof for the prevention or treatment of diseases associated with the activation of STAT proteins, particularly, STAT3 protein and pharmaceutical compositions comprising same.

BACKGROUND ART

STAT (signal transducer and activator of transcription) proteins are transcription factors which transduce signals from various extracellular cytokines and growth factors to a nucleus. Seven (7) subtypes of STAT proteins (STAT1, STAT2, STAT3, STAT4, STAT5a, STAT5b, STAT6) are currently known, and generally they consist of about 750-850 amino acids. In addition, each subtype of STAT proteins contains several conserved domains which play an important role in exhibiting the function of STAT proteins. Specifically, five (5) domains from N-terminus to C-terminus of STAT proteins have been reported including coiled-coiled domain, DNA binding domain, linker domain, SH2 domain and transactivation domain (TAD). Further, X-ray crystalline structures of STAT1, STAT3, STAT4 and STAT5 have been reported since 1998 (Becker S et al., Nature, 1998, 394; Vinkemeier U et al., Science, 1998, 279; Chen X et al., Cell, 1998, 93; D. Neculai et al., J. Biol. Chem., 2005, 280). In general, receptors to which cytokines and growth factors bind are categorized into Class I and Class II. IL-2, IL-3, IL-5, IL-6, IL-12, G-CSF, GM-CSF, LIF, thrombopoietin, etc., bind to Class I receptors, while INF-α, INF-γ, IL-10, etc., bind to Class II receptors (Schindler C et al., Annu. Rev. Biochem., 1995, 64; Novick D et al., Cell, 1994, 77; Ho A S et al., Proc. Natl. Acad. Sci., 1993, 90). Among them, the cytokine receptors involved in activation of STAT proteins can be classified depending on their structural forms of extracellular domains into a gp-130 family, an IL-2 family, a growth factor family, an interferon family and a receptor tyrosine kinase family. Interleukin-6 family cytokines are representative multifunctional cytokines which mediate various physiological activities. When IL-6 binds to the IL-6 receptor which is present on the cell membrane surface, it attracts gp-130 receptor to form an IL-6-gp-130 receptor complex. At this time, JAK kinases (JAK1, JAK2, JAK3 and Tyk2) in the cytoplasm are recruited to a cytoplasmic region of gp130 to be phosphorylated and activated. Subsequently, latent cytoplasmic STAT proteins are attracted to a receptor, phosphorylated by JAK kinases and activated. Tyrosine-705 adjacent to the SH2 domain located in the C-terminus of STAT proteins is phosphorylated, and the activated tyrosine-705 of each STAT protein monomer binds to the SH2 domain of another monomer in a reciprocal manner, thereby forming a homo- or heterodimer. The dimer are translocalized into a nucleus and bind to a specific DNA binding promoter to promote the transcription. Through its transcription process, various proteins (Myc, Cyclin D1/D2, BCLxL, Mcl, survivin, VEGF, HIF1, Immunosuppressive factor, etc.) through transcription process (Stark et al., Annu. Rev. Biochem., 1997, 67; Levy et al., Nat. Rev. Mol. Cell Biol., 2002, 3).

In particular, STAT3 protein is known to play a crucial role in the acute inflammatory response and the signal transduction pathway of IL-6 and EGF (Akira et al., Cell, 1994, 76; Zhong et al., Science, 1994, 264). According to the recent clinical report, STAT3 protein is constantly activated in patients with solid cancers occurring in prostate, stomach, breast, lung, pancreas, kidney, uterine, ovary, head and neck, etc., and also in patients with blood cancer such as acute and chronic leukemia, multiple myeloma, etc. Further, it has been reported that the survival rate of a patient group with activated STAT3 is remarkably lower than that of a patient group with inactivated STAT3 (Masuda et al., Cancer Res., 2002, 62; Benekli et al., Blood, 2002, 99; Yuichi et al., Int. J. Oncology, 2007, 30). Meanwhile, STAT3 was identified to be an essential factor for the growth and maintenance of murine embryonic stem cells in a study employing a STAT3 knockout mouse model. Also, a study with a tissue-specific STAT3-deficient mouse model reveals that STAT3 plays an important role in cell growth, apoptosis, and cell motility in a tissue-specific manner (Akira et al., Oncogene 2000, 19). Moreover, since apoptosis induced by anti-sensing STAT3 was observed in various cancer cell lines, STAT3 is considered as a promising new anticancer target. STAT3 is also considered as a potential target in the treatment of patients with diabetes, immune system diseases, hepatitis C, macular degeneration, papilloma virus infection, non-Hodgkin's lymphoma and tuberculosis patients. Contrary to this, STAT1 increases inflammation, innate, acquired immunity with the same cytokines and growth factors, while sharing the intracellular down-pathway of the same cytokines and growth factors, leading to anti-proliferation or pro-apoptotic responses in most cases. As such, it has been known that STAT1 plays an opposite role to STAT3 (Valeria Poli et al., Review, Landes Bioscience, 2009).

The strategies for developing STAT3 inhibitors can be largely divided into i) inhibition of STAT3 protein phosphorylation by IL-6/gp-130/JAK kinase, ii) direct inhibition of dimerization of activated STAT3, and iii) inhibition of binding of STAT3 dimer to DNA in the nucleus of STAT3.

As small molecule STAT3 inhibitors under development, it has been reported that OPB-31121, OPB-51602 and OPB-111077, which are being developed by Otsuka Pharmaceutical Co., Ltd., are undergoing clinical trials for solid tumor and blood cancer patients, and S3I-201 (Siddiquee et al., Proc. Natl. Acad. Sci., 2007, 104), S3I-M2001 (Siddiquee et al., Chem. Biol., 2007, 2), LLL-12 (Lin et al., Neoplasia, 2010, 12), Stattic (Schust et al., Chem. Biol. 2006, 13), STA-21 (Song et al., Proc. Natl. Acad. Sci., 2005, 102), SF-1-066 (Zhang et al., Biochem. Pharm., 2010, 79) and STX-0119 (Matsuno et al., ACS Med. Chem. Lett., 2010, 1), etc. have been reported to be effective in a cancer cell growth inhibition experiment and in animal model (in vivo Xenograft model). Furthermore, although peptide compounds mimicking the sequence of amino acid of pY-705 (STAT3) adjacent to the binding site to SH2 domain or the amino acid sequence of gp-130 receptor in which JAK kinases bind were studied (Turkson J et al., Mol Cancer Ther. 2004, 261, Coleman et al., J. Med. Chem., 2005, 48), the development of the peptide compounds has not been successful due to the problems such as solubility and membrane permeability.

PRIOR DOCUMENTS

Non-Patent Documents (Non-patent document 1) Becker S et al., Nature, 1998, 394.
(Non-patent document 2) Vinkemeier U et al., Science, 1998, 279
(Non-patent document 3) Chen X et al., Cell, 1998, 93
(Non-patent document 4) D. Neculai et al., J. Biol. Chem., 2005, 280
(Non-patent document 5) Schindler C et al., Annu. Rev. Biochem., 1995, 64
(Non-patent document 6) Novick D et al., Cell, 1994, 77
(Non-patent document 7) Ho A S et al., Proc. Natl. Acad. Sci., 1993, 90
(Non-patent document 8) Stark et al., Annu. Rev. Biochem., 1997, 67
(Non-patent document 9) Levy et al., Nat. Rev. Mol. Cell Biol., 2002, 3
(Non-patent document 10) Akira et al., Cell, 1994, 76
(Non-patent document 11) Zhong et al., Science, 1994, 264
(Non-patent document 12) Masuda et al., Cancer Res., 2002, 62
(Non-patent document 13) Benekli et al., Blood, 2002, 99
(Non-patent document 14) Yuichi et al., Int. J. Oncology, 2007, 30
(Non-patent document 15) Akira et al., Oncogene 2000, 19
(Non-patent document 16) Valeria Poli et al., Review, Landes Bioscience, 2009
(Non-patent document 17) Siddiquee et al., Proc. Natl. Acad. Sci., 2007, 104
(Non-patent document 18) Siddiquee et al., Chem. Biol., 2007, 2
(Non-patent document 19) Lin et al., Neoplasia, 2010, 12
(Non-patent document 20) Schust et al., Chem. Biol. 2006, 13
(Non-patent document 21) Song et al., Proc. Natl. Acad. Sci., 2005, 102
(Non-patent document 22) Zhang et al., Biochem. Pharm., 2010, 79
(Non-patent document 23) Matsuno et al., ACS Med. Chem. Lett., 2010, 1
(Non-patent document 24) Turkson J et al., Mol Cancer Ther. 2004, 261
(Non-patent document 25) Coleman et al., J. Med. Chem., 2005, 48

DISCLOSURE OF INVENTION

Technical Problem

Accordingly, the purpose of the present invention is the provision of a novel heterocyclic compounds which inhibit the activation of STAT3 protein.

Another purpose of the present invention is the provision of a pharmaceutical composition for the prevention or treatment of diseases associated with the activation of STAT3 protein.

Solution to Problem

According to the present invention, there is provided a heterocyclic compound of the following Formula 1, or a pharmaceutically acceptable salt or isomer thereof:

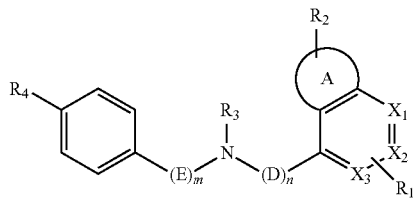

[Formula 1]

wherein
each of $X_1$, $X_2$ and $X_3$ is independently C or N, provided that at least one of $X_1$, $X_2$ and $X_3$ is N;
$R_1$ is hydrogen, halo, alkyl, haloalkyl, alkoxy or alkylamino;
$R_2$ is hydrogen, hydroxy, halo, carboxy, —C(=O)—NH—$NH_2$, alkyl, alkoxy, haloalkoxy, alkoxy-carbonyl, carboxy-alkoxy, aminocarbonyl-alkoxy, alkoxy-carbonyl-alkoxy, aryl, aryl-oxy, aryl-alkyl-aminosulfonyl, aryl-carbonyl, aminocarbonyl, 5- to 8-membered heterocycloalkyl or 5- to 8-membered heterocycloalkyl-carbonyl, wherein the heterocycloalkyl has 1 to 3 heteroatoms selected from N, O and S, and the aryl is optionally substituted with nitro or halo;
$R_3$ is hydrogen or aryl-alkyl;
$R_4$ is nitro, nitroso, amino, amino-sulfonyl, alkylsulfonyl-amino, alkylsulfonylhydroxyamino(-N(OH)S($O_2$)alkyl) or haloalkylsulfonyl-amino; provided that when $R_1$ is alkyl, $R_4$ is not alkylsulfonyl-amino;
A ring is aryl or 3- to 8-membered saturated or unsaturated heterocycle having 1 to 3 heteroatoms selected from N, O and S;
D is —$CH_2$— optionally substituted with oxo;
E is —$CH_2$— optionally substituted with oxo or halo;
n is an integer of 0 to 2; and
m is an integer of 1 to 4.

Unless mentioned otherwise, herein the term "alkyl," either alone or in combination with further terms (for example, alkoxy), means a radical of saturated aliphatic hydrocarbyl group having preferably 1 to 6 carbon atoms, which may be linear or branched.

Unless mentioned otherwise, herein the term "alkoxy" means alkyloxy, preferably alkyloxy having 1 to 6 carbon atoms.

Unless mentioned otherwise, herein the term "halo" means a radical of fluorine (F), chlorine (Cl), bromine (Br) or iodine (I).

Unless mentioned otherwise, herein the term "aryl" means an aromatic radical having preferably 6 to 10 carbon atoms. Concrete examples of aryl include, but are not limited to, phenyl and naphthyl.

Unless mentioned otherwise, herein the term "heterocycloalkyl" means 5- to 10-membered saturated monocyclic or bicyclic ring having preferably 1 to 3 heteroatoms selected from N, O and S. Concrete examples of heterocycloalkyl include, but are not limited to, pyrrolidine, piperidine, tetrahydrofuran, tetrahydropyran, morpholine, thiomorpholine and piperazine.

Unless mentioned otherwise, herein the term "heterocycle" means 5- to 8-membered saturated or unsaturated monocyclic ring having preferably 1 to 3 heteroatoms selected from N, O and S. Concrete examples of heterocycle include, but are not limited to, pyridine, imidazole, pyrimidine, thiophene and furan.

According to one embodiment of the present invention, in Formula 1, each of $X_1$, $X_2$ and $X_3$ is independently C or N, provided that at least one of $X_1$, $X_2$ and $X_3$ is N;

$R_1$ is hydrogen, halo, $C_1$-$C_6$-alkyl, halo-$C_1$-$C_6$-alkyl, $C_1$-$C_6$ alkoxy or $C_1$-$C_6$-alkylamino;

$R_2$ is hydrogen, hydroxy, halo, carboxy, —C(=O)—NH—NH$_2$, $C_1$-$C_6$-alkyl, $C_1$-$C_6$-alkoxy, halo-$C_1$-$C_6$-alkoxy, $C_1$-$C_6$-alkoxy-carbonyl, carboxy-$C_1$-$C_6$-alkoxy, aminocarbonyl-$C_1$-$C_6$-alkoxy, $C_1$-$C_6$-alkoxy-carbonyl-$C_1$-$C_6$-alkoxy, $C_6$-$C_{10}$-aryl, $C_6$-$C_{10}$-aryl-oxy, $C_6$-$C_{10}$-aryl-$C_1$-$C_6$-alkyl-aminosulfonyl, $C_6$-$C_{10}$-aryl-carbonyl, aminocarbonyl, 5- to 8-membered heterocycloalkyl or 5- to 8-membered heterocycloalkylcarbonyl, wherein the heterocycloalkyl has 1 to 3 heteroatoms selected from N, O and S, and the aryl is optionally substituted with nitro or halo;

$R_3$ is hydrogen or $C_6$-$C_{10}$-aryl-$C_1$-$C_6$-alkyl;

$R_4$ is nitro, nitroso, amino, amino-sulfonyl, $C_1$-$C_6$-alkylsulfonyl-amino, $C_1$-$C_6$-alkylsulfonylhydroxyamino or halo-$C_1$-$C_6$-alkylsulfonyl-amino; provided that when $R_1$ is $C_1$-$C_6$-alkyl, $R_4$ is not $C_1$-$C_6$-alkylsulfonyl-amino;

A ring is $C_6$-$C_{10}$-aryl or 5- or 6-membered saturated or unsaturated heterocycle having 1 to 3 heteroatoms selected from N, O and S;

D is —CH$_2$— optionally substituted with oxo;

E is —CH$_2$— optionally substituted with oxo or halo;

n is an integer of 0 to 2; and m is an integer of 1 to 4.

According to another embodiment of the present invention, in Formula 1, $X_1$ is N, and each of $X_2$ and $X_3$ is independently C or N.

According to still another embodiment of the present invention, in Formula 1, $R_1$ is halo, $C_1$-$C_6$-alkyl, halo-$C_1$-$C_4$-alkyl, $C_1$-$C_4$ alkoxy or $C_1$-$C_4$-alkylamino.

According to still another embodiment of the present invention, in Formula 1, $R_2$ is hydrogen, hydroxy, halo, carboxy, —C(=O)—NH—NH$_2$, $C_1$-$C_4$-alkyl, $C_1$-$C_4$-alkoxy, halo-$C_1$-$C_4$-alkoxy, $C_1$-$C_4$-alkoxy-carbonyl, carboxy-$C_1$-$C_4$-alkoxy, aminocarbonyl-$C_1$-$C_4$-alkoxy, $C_1$-$C_4$-alkoxy-carbonyl-$C_1$-$C_4$-alkoxy, phenyl, phenoxy, phenyl-$C_1$-$C_4$-alkyl-aminosulfonyl, phenyl-carbonyl, aminocarbonyl, 5- or 6-membered heterocycloalkyl, or 5- or 6-membered heterocycloalkylcarbonyl, wherein the heterocycloalkyl has 1 to 3 heteroatoms selected from N, O and S, and the phenyl is optionally substituted with nitro or halo.

According to still another embodiment of the present invention, in Formula 1, $R_3$ is hydrogen or phenyl-$C_1$-$C_4$-alkyl.

According to still another embodiment of the present invention, in Formula 1, $R_4$ is nitro, nitroso, amino, amino-sulfonyl, $C_1$-$C_4$-alkylsulfonyl-amino, $C_1$-$C_4$-alkylsulfonylhydroxyamino or halo-$C_1$-$C_4$-alkylsulfonyl-amino.

According to still another embodiment of the present invention, in Formula 1, A ring is phenyl or 5- or 6-membered unsaturated heterocycle having 1 to 3 heteroatoms selected from N and S.

As representative examples of the compound of Formula 1 according to the present invention, the following compounds may be mentioned, but are not limited thereto:

2-chloro-N-(4-nitrophenethyl)quinolin-4-amine;
N-(4-(2-((2-chloroquinolin-4-yl)amino)ethyl)phenyl)-N-hydroxymethanesulfonamide;
4-(2-((2-chloroquinolin-4-yl)amino)ethyl)benzenesulfonamide;
4-(2-((2-chloroquinolin-4-yl)(phenethyl)amino)ethyl)benzenesulfonamide;
2-methyl-N-(4-nitrophenethyl)quinolin-4-amine;
N-(4-aminophenethyl)-2-chloroquinolin-4-amine;
N-(4-(2-((2-chloroquinolin-4-yl)amino)ethyl)phenyl)methanesulfonamide;
2-chloro-8-ethyl-N-(4-nitrophenethyl)quinolin-4-amine;
2-chloro-6-methoxy-N-(4-nitrophenethyl)quinolin-4-amine;
2-chloro-8-methoxy-N-(4-nitrophenethyl)quinolin-4-amine;
N-(4-(2-((2-chloro-6-methoxyquinolin-4-yl)amino)ethyl)phenyl)methanesulfonamide;
2-chloro-N-(4-nitrophenethyl)-7-(trifluoromethoxy)quinolin-4-amine;
2-chloro-N-(4-nitrophenethyl)-5-(trifluoromethoxy)quinolin-4-amine;
2-chloro-6-fluoro-N-(4-nitrophenethyl)quinolin-4-amine;
2-chloro-8-methyl-N-(4-nitrophenethyl)quinolin-4-amine;
ethyl 2-chloro-4-((4-nitrophenethyl)amino)quinolin-6-carboxylate;
N-(4-nitrophenethyl)quinolin-4-amine;
2-chloro-N-(4-nitrophenethyl)quinazolin-4-amine;
2-chloro-N-(4-nitrophenethyl)-4-((4-nitrophenethyl)amino)quinolin-6-sulfonamide;
2-chloro-N-(4-nitrosophenethyl)quinolin-4-amine;
N-(4-(2-((6-fluoroquinolin-4-yl)amino)ethyl)phenyl)methanesulfonamide;
N-(4-(2-((2-chloro-6-fluoroquinolin-4-yl)amino)ethyl)phenyl)methanesulfonamide;
N-(4-(2-((2-chloroquinazolin-4-yl)amino)ethyl)phenyl)methanesulfonamide;
N-(4-(2-((2-chloro-7-(trifluoromethoxy)quinolin-4-yl)amino)ethyl)phenyl)methanesulfonamide;
N-(4-(2-((7-(trifluoromethoxy)quinolin-4-yl)amino)ethyl)phenyl)methanesulfonamide;
N-(4-(2-((2-chloro-5-(trifluoromethoxy)quinolin-4-yl)amino)ethyl)phenyl)methanesulfonamide;
N-(4-(2-((5-(trifluoromethoxy)quinolin-4-yl)amino)ethyl)phenyl)methanesulfonamide;
2-chloro-6-morpholino-N-(4-nitrophenethyl)quinolin-4-amine 2,2,2-trifluoroacetate;
2-chloro-5-fluoro-N-(4-nitrophenethyl)quinolin-4-amine;
2-chloro-7-fluoro-N-(4-nitrophenethyl)quinolin-4-amine;
2-chloro-8-fluoro-N-(4-nitrophenethyl)quinolin-4-amine;
2,6-dichloro-N-(4-nitrophenethyl)quinolin-4-amine;
2-chloro-N-(4-nitrophenethyl)-6-phenoxyquinolin-4-amine;
(2-chloro-4-((4-nitrophenethyl)amino)quinolin-6-yl)(phenyl)methanone:
2-chloro-4-((4-nitrophenethyl)amino)quinolin-6-ol;
N-(4-nitrophenethyl)quinazolin-4-amine;
ethyl 2-((2-chloro-4-((4-nitrophenethyl)amino)quinolin-6-yl)oxy)acetate;
N-(4-(2-(quinazolin-4-ylamino)ethyl)phenyl)methanesulfonamide;
2-((2-chloro-4-((4-nitrophenethyl)amino)quinolin-6-yl)oxy)acetamide;
2-chloro-4-((4-nitrophenethyl)amino)quinolin-6-carboxylic acid;
2-chloro-4-((4-nitrophenethyl)amino)quinolin-6-carboxamide;
(2-chloro-4-((4-nitrophenethyl)amino)quinolin-6-yl)(morpholino)methanone;
2-((2-chloro-4-((4-nitrophenethyl)amino)quinolin-6-yl)oxy)acetic acid;
2-chloro-4-((4-nitrophenethyl)amino)quinolin-6-carbohydrazide;
N-(4-(2-((2-chloro-8-fluoroquinolin-4-yl)amino)ethyl)phenyl)methanesulfonamide;
N-(4-(2-((8-fluoroquinolin-4-yl)amino)ethyl)phenyl)methanesulfonamide;
2-chloro-N-(4-nitrophenethyl)-9H-purin-6-amine;

N-(4-nitrophenethyl)-2-(trifluoromethyl)quinazolin-4-amine;
N-(4-nitrophenethyl)-2-(trifluoromethyl)quinolin-4-amine;
2-fluoro-N-(4-nitrophenethyl)-9H-purin-6-amine;
$N^2$-methyl-$N^4$-(4-nitrophenethyl)quinolin-2,4-diamine 2,2,2-trifluoroacetate;
N-(4-(2-((2-(trifluoromethyl)quinolin-4-yl)amino)ethyl) phenyl)methanesulfonamide;
N-(4-(2-((2-(trifluoromethyl)quinazolin-4-yl)amino)ethyl) phenyl)methanesulfonamide;
6-(2,4-dichlorophenyl)-N-(4-nitrophenethyl)quinazolin-4-amine;
2-chloro-6-(2,4-dichlorophenyl)-N-(4-nitrophenethyl)quinolin-4-amine;
N-(4-(2-((6-(2,4-dichlorophenyl)quinazolin-4-yl)amino) ethyl)phenyl)methanesulfonamide;
N-(4-(2-((2-chloro-6-(2,4-dichlorophenyl)quinolin-4-yl) amino)ethyl)phenyl)methane sulfonamide;
2-chloro-N-(4-(methylsulfonamido)benzyl)quinolin-4-carboxamide;
N-(2,2-difluoro-2-(4-nitrophenyl)ethyl)quinazolin-4-amine;
1,1,1-trifluoro-N-(4-(2-(quinazolin-4-ylamino)ethyl)phenyl)methanesulfonamide;
6-fluoro-N-(4-nitrophenethyl)quinazolin-4-amine;
N-(4-nitrophenethyl)isoquinolin-4-amine;
N-(4-(2-(isoquinolin-4-ylamino)ethyl)phenyl)methanesulfonamide;
N-(4-(2-((6-fluoroquinazolin-4-yl)amino)ethyl)phenyl) methanesulfonamide;
2-(4-nitrophenyl)-N-(quinazolin-4-yl)acetamide;
N-(4-(2-(thieno[3,2-d]pyrimidin-4-ylamino)ethyl)phenyl) methanesulfonamide;
2-chloro-N-(4-nitrophenethyl)pyrido[2,3-d]pyrimidin-4-amine;
N-(4-(2-(thieno[2,3-d]pyrimidin-4-ylamino)ethyl)phenyl) methanesulfonamide;
N-(4-(2-(thiazolo[5,4-d]pyrimidin-7-ylamino)ethyl)phenyl) methanesulfonamide;
N-(4-(2-((7H-pyrrolo[2,3-d]pyrimidin-4-yl)amino)ethyl) phenyl)methanesulfonamide;
N-(4-(2-(pyrido[3,4-b]pyrazin-5-ylamino)ethyl)phenyl) methanesulfonamide;
N-(4-(2-((3-methylquinolin-4-yl)amino)ethyl)phenyl)methanesulfonamide;
N-(4-(2-(furo[3,2-c]pyridin-4-ylamino)ethyl)phenyl)methanesulfonamide;
N-(4-(2-((4-chloroisoquinolin-1-yl)amino)ethyl)phenyl) methanesulfonamide;
N-(4-(2-(isoquinolin-1-ylamino)ethyl)phenyl)methanesulfonamide; and
N-(4-(2-((2-methoxyquinolin-4-yl)amino)ethyl)phenyl) methanesulfonamide.

The above-listed names of the compounds are described in accordance with the nomenclature method provided by ChemDraw Professional (Version 15.0.0.106) of PerkinElmer.

The compound of Formula 1 according to the present invention may also form a pharmaceutically acceptable salt. Representative acids useful in preparing such a pharmaceutically acceptable salt include, but not limited to, hydrochloric acid, sulfuric acid, nitric acid, phosphoric acid, hydrobromic acid, hydroiodic acid, formic acid, citric acid, acetic acid, trichloroacetic acid or trifluoroacetic acid, benzoic acid, fumaric acid, maleic acid, methane sulfonic acid, benzene sulfonic acid, p-toluene sulfonic acid, 2,2-dichloroacetic acid, acylated amino acids, adipic acid, alginic acid, ascorbic acid, L-aspartic acid, 4-acetamidobenzoic acid, (+)-camphoric acid, camphorsulfonic acid, (+)-(1S)-camphorsulfonic acid, capric acid, caproic acid, caprylic acid, cinnamic acid, cyclamic acid, dodecyl sulfuric acid, ethane-1,2-disulfonic acid, ethanesulfonic acid, 2-hydroxyethanesulfonic acid, galactaric acid, gentisic acid, glucoheptanoic acid, D-gluconic acid, D-glucuronic acid, L-glutamic acid, α-oxo-glutaric acid, glycolic acid, hippuric acid, (+)-L-lactic acid, (±)-DL-lactic acid, lactobionic acid, (−)-L-malic acid, malonic acid, (±)-DL-mandelic acid, methane sulfonic acid, naphthalene-2-sulfonic acid, naphthalene-1,5-disulfonic acid, 1-hydroxy-2-naphthoic acid, nicotinic acid, oleic acid, orotic acid, oxalic acid, palmitic acid, pamoic acid, L-pyroglutamic acid, salicylic acid, 4-amino-salicylic acid, sebacic acid, stearic acid, succinic acid, tannic acid, (+)-L-tartaric acid, thiocyanic acid, undecylenic acid and the like. In addition, other acid salts that are known and used in the art of amine derivatives may be included. They may be prepared by conventionally known processes.

The compound of Formula 1 as defined above according to the present invention may be prepared by, but not limited to, the methods described in the following Examples.

The compound of Formula 1 according to the present invention has an excellent activity for inhibiting the activation of STAT3 protein. Therefore, the present invention also provides a pharmaceutical composition comprising a therapeutically effective amount of a compound of Formula 1, or a pharmaceutically acceptable salt or isomer thereof as an active ingredient, and a pharmaceutically acceptable carrier.

The compound of Formula 1 according to the present invention—which inhibits the activation of STAT3 protein—is useful for preventing or treating solid tumors, blood cancers, radiation or drug-resistant cancers, metastatic cancers, inflammatory diseases, immune system diseases, diabetes, macular degeneration, papillomavirus infections and tuberculosis.

The compound of Formula 1 according to the present invention—which inhibits the activation of STAT3 protein—is useful for preventing or treating diseases associated with the activation of STAT3 protein, for example breast cancer, lung cancer, stomach cancer, prostate cancer, uterine cancer, ovarian cancer, renal cancer, pancreatic cancer, liver cancer, colon cancer, skin cancer, head and neck cancer, thyroid cancer, osteosarcoma, acute or chronic leukemia, multiple myeloma, non-Hodgkin's lymphoma, autoimmune diseases including rheumatoid arthritis, psoriasis, hepatitis, inflammatory bowel disease, Crohn's disease, diabetes, macular degeneration, papillomavirus infections and tuberculosis.

A pharmaceutical composition according to the present invention may be prepared by mixing a therapeutically effective amount of a compound of Formula 1, or a pharmaceutically acceptable salt or isomer thereof as an active ingredient, with a pharmaceutically acceptable carrier, binder, stabilizer and/or diluent. In addition, when the pharmaceutical composition according to the present invention is prepared in an injection liquid form, a pharmaceutically acceptable buffer, dissolution adjuvant and/or isotonic agent may be mixed with the compound of Formula 1, or a pharmaceutically acceptable salt or isomer thereof.

The pharmaceutical composition according to the prevent invention may be prepared in a delivery form of a pharmaceutical composition comprising one or more dosage units of pharmaceutical agent by using a preparation technique known or available to a skilled artisan, and a suitable pharmaceutical excipient. In a method of the present invention, the composition may be administered via suitable delivery route, for example, such as oral or parenteral, percutaneous, rectal, topical or ocular administration, or by inhalation. The pharmaceutical formulation may be in a form of tablet, capsule, sachet, sugar-coated pill, powder, granule, lozenge, powder for reconstitution, liquid preparation or suppository. For example, the composition may be formulated in a form for intravenous injection, spray, topical or oral administration.

In case of preparing a formulation in oral dosage form, any conventional pharmaceutical carriers may be used. For example, water, glycols, oils, alcohols and the like may be used as a carrier in case of oral liquid formulations such as suspensions, syrups, elixirs and solutions; and starches, sugars, kaolin, lubricants, binders, disintegrating agents and the like may be used as a carrier in case of solid formulations such as powders, pills, capsules and tablets. Because of the easiness of administration, tablets and capsules are the most convenient dose forms, and tablets and pills are preferably prepared as enteric coating formulations.

In case of parenteral formulations, sterilized water is used usually and other ingredient(s) such as a dissolution adjuvant may also be comprised. Injection formulations, for example, sterilized aqueous- or oil-based suspension for injection may be prepared according to known techniques by using appropriate dispersing agent, wetting agent or suspending agent. The solvents useful for this purpose include water, ringer solution and isotonic NaCl solution, and sterilized, immobilized oils are also used as a solvent or a suspending medium conventionally. Any non-irritant immobilized oils including mono- and di-glycerides may be used for this purpose, and fatty acids such as an oleic acid may be used for an injection formulation.

In case of percutaneous formulations, a penetration-enhancing agent and/or a suitable wetting agent may be used as a carrier, optionally in combination with suitable non-irritant additive(s) to the skin. As such additives, those helpful in enhancing the administration through the skin and/or preparing the desired composition may be selected. The percutaneous formulation may be administered in various ways, for example, such as a transdermal patch, a spot-on treatment or an ointment.

The administration time and dosage of the pharmaceutical composition according to the present invention may be suitably determined according to the patient's disease, condition, age, body weight and administration form. In case of adults, the pharmaceutical composition may be administered in an amount of 0.1-2,000 mg, preferably 1-200 mg per day, in a single dose or multiple doses, but not limited thereto.

Advantageous Effects of Invention

The heterocyclic compound of Formula 1, or a pharmaceutically acceptable salt or isomer thereof according to the present invention exhibits an excellent inhibitory effect against the activation of STAT3 protein, and thus a pharmaceutical composition comprising the same is useful in the prevention or treatment of diseases associated with the activation of STAT3 protein.

MODE FOR THE INVENTION

Hereinafter, the present invention is explained in more detail with the following examples. However, the following examples are only intended to facilitate understanding of the present invention, and the protection scope of the present invention is not limited thereto.

The abbreviations used in the following examples are defined as follows.

| Abbreviation | Full Name |
|---|---|
| $BBr_3$ | Boron tribromide |
| BINAP | 2,2'-Bis(diphenylphosphino)-1,1'-binaphthyl |
| Brine | Brine is water, saturated or nearly saturated with salt (usually sodium chloride) |
| Celite | Trade name of diatomaceous earth |
| $CH_3CN$ | Acetonitrile |
| $CDCl_3$ | Deuterated chloroform |
| $CD_3OD$ | Fully deuterated methanol |
| $CH_2Cl_2$ | Dichloromethane |
| DAST | Diethylaminosulfur trifluoride |
| DIPEA | N,N-Diisopropylethylamine |
| DMA | Dimethylacetamide |
| DME | Dimethoxyethane |
| DMF | N,N-Dimethylformamide |
| DMSO | Dimethylsulfoxide |
| DMSO-$d_6$ | Fully deuterated dimethylsulfoxide |
| EDC | Ethyl-(N,N-dimethylamino)propylcarbodiimide |
| EtOAc | Ethyl acetate |
| EtOH | Ethyl alcohol |
| $Et_3N$ | Triethylamine |
| HCl | Hydrochloric acid |
| n-Hex | n-Hexane |
| $H_2O$ | Water |
| HOBT | 1-Hydroxybenzotriazole |
| i-PrOH | iso-Propyl alcohol |
| $K_2CO_3$ | Potassium carbonate |
| MeOH | Methyl alcohol |
| MsCl | Methanesulfonyl chloride |
| $Na_2CO_3$ | Sodium carbonate |
| $Na_2SO_4$ | Sodium sulfate |
| $NaHCO_3$ | Sodium bicarbonate |
| NaOH | Sodium hydroxide |
| $NaBH_4$ | Sodium borohydride |
| $NH_4Cl$ | Ammonium chloride |
| $NaBH_3CN$ | Sodium cyanoborohydride |
| NMP | n-methylpyrrolidone |
| $Pd_2(dba)_3$ | Tris(dibenzylideneacetone)dipalladium(0) |
| $Pd(PPh_3)_4$ | Tetrakis(triphenylphosphine)palladium |
| $PPh_3$ | Triphenylphosphine |
| Raney Ni | Raney nickel |
| $Tf_2O$ | Trifluoromethanesulfonic anhydride |
| THF | Tetrahydrofuran |
| Zn | Zinc |

Example 1: Synthesis of 2-chloro-N-(4-nitrophenethyl)quinolin-4-amine

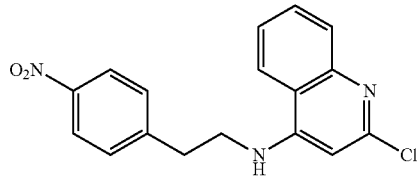 [SMILES: O=[N+]([O-])c1ccc(CCNc2cc(Cl)nc3ccccc23)cc1]

2,4-Dichloroquinoline (100.0 mg, 0.50 mmol), 2-(4-nitrophenyl)ethan-1-amine hydrochloride (101.0 mg, 0.50 mmol) and $Et_3N$ (350.0 µL, 2.50 mmol) were added to DMF (4.0 mL). The reaction mixture was reacted in a microwaver (100 W, 150° C.) for 30 minutes and cooled to room temperature. After addition of ice water, the reaction mixture was extracted with $CH_2Cl_2$. The organic layer was washed with brine, dried with $Na_2SO_4$ and filtered. The residue obtained under reduced pressure was purified by column chromatography (n-Hex:$CH_2Cl_2$=1:1) on amine silica. The fractions containing the product were collected and evaporated to obtain the white solid compound, 2-chloro-N-(4-nitrophenethyl)quinolin-4-amine (25.0 mg, 15%).

$^1$H NMR (300 MHz, CDCl$_3$) δ=8.27-8.14 (m, 2H), 7.96-7.85 (m, 1H), 7.66 (ddd, J=1.1, 6.9, 8.4 Hz, 1H), 7.57-7.49 (m, 1H), 7.47-7.35 (m, 3H), 6.43 (s, 1H), 5.14-5.03 (m, 1H), 3.75-3.63 (m, 2H), 3.19 (t, J=6.9 Hz, 2H)

LC/MS ESI (+): 328 (M+1)

Example 2: Synthesis of N-(4-(2-((2-chloroquinolin-4-yl)amino)ethyl)phenyl)-N-hydroxymethanesulfonamide

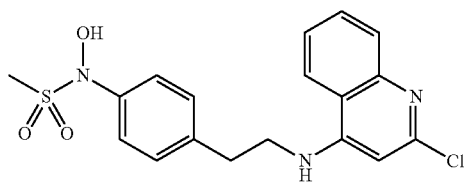 [SMILES: CS(=O)(=O)N(O)c1ccc(CCNc2cc(Cl)nc3ccccc23)cc1]

(a) Synthesis of 2-chloro-N-(4-(hydroxyamino)phenethyl)quinolin-4-amine

2-Chloro-N-(4-nitrophenethyl)quinolin-4-amine (100.0 mg, 0.30 mmol) was dissolved in a mixed solvent of CH$_3$CN/CH$_2$Cl$_2$ (4.0 mL, 3/1 v/v), and Zn (100.0 mg, 1.50 mmol) and ammonium formate (192.0 mg, 3.0 mmol) were added thereto at room temperature. The reaction mixture was stirred at 25° C. for 2 hours. After addition of water, the reaction mixture was extracted with CH$_2$Cl$_2$, washed with brine, dried with Na$_2$SO$_4$, filtered and evaporated under reduced pressure. The residue was purified by column chromatography (CH$_2$Cl$_2$:MeOH=20:1) on silica. The fractions containing the product were collected and evaporated to obtain the white solid compound, 2-chloro-N-(4-hydroxyamino)phenethyl)quinolin-4-amine (50.0 mg, 53%).

LC/MS ESI (+): 314 (M+1)

(b) Synthesis of N-(4-(2-((2-chloroquinolin-4-yl)amino)ethyl)phenyl)-N-hydroxymethanesulfonamide 2-Chloro-N-(4-(hydroxyamino)phenethyl)quinolin-4-amine (50.0 mg, 0.16 mmol) was dissolved in pyridine (1.6 mL), MsCl (25.0 µL, 0.32 mmol) was slowly added thereto at 0° C. After termination of the reaction, the reaction mixture was extracted with CH$_2$Cl$_2$. The organic layer was washed with brine, dried with Na$_2$SO$_4$, filtered and evaporated under reduced pressure. The residue was purified by column chromatography (CH$_2$Cl$_2$:MeOH=20:1) on silica. The fractions containing the product were collected and evaporated to obtain the white solid compound, N-(4-(2-((2-chloroquinolin-4-yl)amino)ethyl)phenyl)-N-hydroxymethanesulfonamide (10.0 mg, 16%).

$^1$H NMR (300 MHz, CD$_3$OD) δ=8.04-7.95 (m, 1H), 7.76-7.59 (m, 2H), 7.48-7.39 (m, 3H), 7.33-7.24 (m, 2H), 6.48 (s, 1H), 3.63 (t, J=7.2 Hz, 2H), 3.04 (t, J=7.2 Hz, 2H), 2.81 (s, 3H)

LC/MS ESI (+): 392 (M+1)

Example 3: Synthesis of 4-(2-((2-chloroquinolin-4-yl)amino)ethyl)benzenesulfonamide

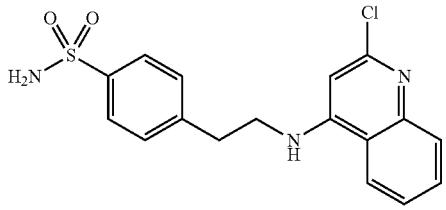 [SMILES: NS(=O)(=O)c1ccc(CCNc2cc(Cl)nc3ccccc23)cc1]

2,4-Dichloroquinoline (100.0 mg, 0.50 mmol), 4-(2-aminoethyl)benzenesulfonamide (100.0 mg, 0.50 mmol) and Et$_3$N (210.0 µL, 1.50 mmol) were added to DMF (2.5 mL). The reaction mixture was reacted in a microwaver (50 W, 100° C.) for 30 minutes and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (CH$_2$Cl$_2$:MeOH=20:1) on amine silica. The fractions containing the product were collected and evaporated to obtain the white solid compound, 4-(2-((2-chloroquinolin-4-yl)amino)ethyl)benzenesulfonamide (25.0 mg, 14%).

$^1$H NMR (300 MHz, CD$_3$OD) δ=8.04-7.95 (m, 1H), 7.86-7.79 (m, 2H), 7.76-7.61 (m, 2H), 7.49-7.40 (m, 3H), 6.52 (s, 1H), 3.66 (t, J=7.2 Hz, 2H), 3.12 (t, J=7.1 Hz, 2H)

LC/MS ESI (+): 362 (M+1)

Example 4: Synthesis of 4-(2-((2-chloroquinolin-4-yl)(phenethyl)amino)ethyl)benzenesulfonamide

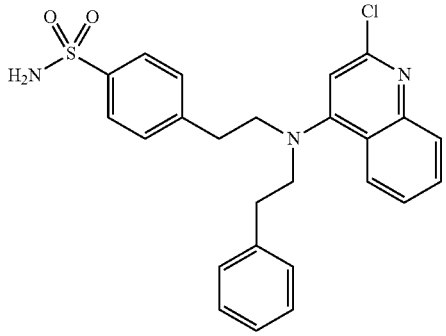 [SMILES: NS(=O)(=O)c1ccc(CCN(CCc2ccccc2)c2cc(Cl)nc3ccccc23)cc1]

(a) Synthesis of 4-(2-(phenethylamino)ethyl)benzenesulfonamide 4-(2-Aminoethyl)benzenesulfonamide (500.0 mg, 2.5 mmol) and 2-phenylacetaldehyde (300.0 mg, 2.5 mmol) were dissolved in MeOH (25.0 mL), and NaBH$_3$CN (470.0 mg, 7.5 mmol) was added thereto. The reaction mixture was stirred at 25° C. for 20 hours and evaporated under reduced pressure. The residue was extracted with EtOAc. The organic layer was washed with brine, dried with Na$_2$SO$_4$, filtered and evaporated under reduced pressure. The residue was purified by column chromatography (CH$_2$Cl$_2$:MeOH=20:1) on silica. The fractions containing the product were collected and evaporated to obtain the white solid compound, 4-(2-(phenethylamino)ethyl)benzenesulfonamide (270.0 mg, 36%).

LC/MS ESI (+): 305 (M+1)

(b) Synthesis of 4-(2-((2-chloroquinolin-4-yl)(phenethyl)amino)ethyl)benzenesulfonamide 2,4-dichloroquinoline (54.0 mg, 0.27 mmol), 4-(2-(phenethylamino)ethyl)benzenesulfonamide (83.0 mg, 0.27 mmol) and Et$_3$N (110.0 μL, 0.81 mmol) were added to DMF (1.5 mL). The reaction mixture was reacted in a microwaver (50 W, 100° C.) for 1 hour and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (CH$_2$Cl$_2$) on amine silica. The fractions containing the product were collected and evaporated to obtain the ivory solid compound, 4-(2-((2-chloroquinolin-4-yl)(phenethyl)amino)ethyl)benzenesulfonamide (2.5 mg, 2%).

$^1$H NMR (300 MHz, CDCl$_3$) δ=7.98 (dd, J=1.0, 8.2 Hz, 1H), 7.86-7.79 (m, 2H), 7.74-7.68 (m, 1H), 7.63-7.55 (m, 1H), 7.42-7.19 (m, 8H), 6.88-6.83 (m, 1H), 4.62 (s, 2H), 3.79-3.64 (m, 4H), 3.05-2.89 (m, 4H)

LC/MS ESI (+): 466 (M+1)

Example 5: Synthesis of 2-methyl-N-(4-nitrophenethyl)quinolin-4-amine

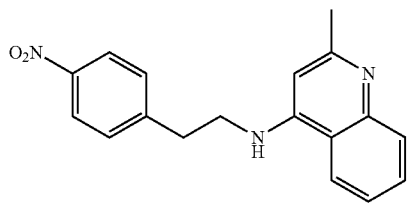 [SMILES: Cc1cc(NCCc2ccc([N+](=O)[O-])cc2)c2ccccc2n1]

4-Chloro-2-methylquinoline (200.0 mg, 1.13 mmol), 2-(4-nitrophenyl)ethan-1-amine hydrochloride (230.0 mg, 1.13 mmol) and Et$_3$N (470.0 μL, 3.39 mmol) were added to NMP (3.6 mL). The reaction mixture was reacted in a microwaver (50 W, 100° C.) for 1 hour and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (n-Hex:EtOAc=2:1) on amine silica. The fractions containing the product were collected and evaporated to obtain yellow liquid compound, 2-methyl-N-(4-nitrophenethyl)quinolin-4-amine (120.0 mg, 35%).

$^1$H NMR (300 MHz, CDCl$_3$) δ=8.26-8.17 (m, 2H), 7.97-7.89 (m, 1H), 7.61 (ddd, J=1.5, 6.9, 8.4 Hz, 1H), 7.54 (d, J=7.6 Hz, 1H), 7.47-7.32 (m, 3H), 6.41 (s, 1H), 4.89 (br s, 1H), 3.73-3.63 (m, 2H), 3.18 (t, J=7.1 Hz, 2H), 2.64 (s, 3H)

LC/MS ESI (+): 308 (M+1)

Example 6: Synthesis of N-(4-aminophenethyl)-2-chloroquinolin-4-amine

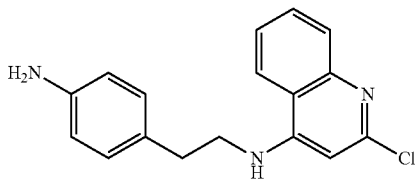 [SMILES: Nc1ccc(CCNc2cc(Cl)nc3ccccc23)cc1]

2-Chloro-N-(4-nitrophenethyl)quinolin-4-amine (30.0 mg, 0.09 mmol) was dissolved in MeOH (2.0 mL), and 5% palladium on activated carbon (3.0 mg, 10 w/w %) was added thereto. The reaction mixture was charged with H$_2$ gas and stirred at room temperature for 1 hour. The reaction mixture was filtered with celite and evaporated under reduced pressure. The residue was purified by column chromatography (CH$_2$Cl$_2$) on amine silica. The fractions containing the product were collected and evaporated to obtain the white solid compound, N-(4-aminophenethyl)-2-chloroquinolin-4-amine (121.7 mg, 81%).

$^1$H NMR (300 MHz, CDCl$_3$) δ=7.93-7.83 (m, 1H), 7.62 (ddd, J=1.5, 6.9, 8.4 Hz, 1H), 7.54-7.46 (m, 1H), 7.44-7.34 (m, 1H), 7.09-7.00 (m, 2H), 6.72-6.66 (m, 2H), 6.50-6.41 (m, 1H), 5.12 (br s, 1H), 3.66 (br s, 2H), 3.57-3.47 (m, 2H), 3.00-2.91 (m, 2H)

LC/MS ESI (+): 298 (M+1)

Example 7: Synthesis of N-(4-(2-((2-chloroquinolin-4-yl)amino)ethyl)phenyl)methanesulfonamide

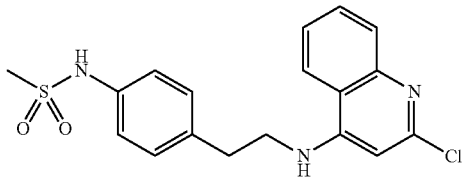 [SMILES: CS(=O)(=O)Nc1ccc(CCNc2cc(Cl)nc3ccccc23)cc1]

N-(4-Aminophenethyl)-2-chloroquinolin-4-amine (8.0 mg, 0.03 mmol) was dissolved in pyridine (0.3 mL), and MsCl (4.0 μL, 0.05 mmol) was slowly added thereto at 0° C. After termination of the reaction, the reaction mixture was extracted with CH$_2$Cl$_2$. The organic layer was washed with brine, dried with Na$_2$SO$_4$, filtered and distilled under reduced pressure. The residue was purified by column chromatography (n-Hex:EtOAc=1:1) on silica. The fractions containing the product were collected and evaporated to obtain the white solid compound, N-(4-(2-((2-chloroquinolin-4-yl)amino)ethyl)phenyl)methanesulfonamide (5.0 mg, 49%).

$^1$H NMR (300 MHz, CD$_3$OD) δ=8.05-7.98 (m, 1H), 7.75-7.61 (m, 2H), 7.48-7.40 (m, 1H), 7.29-7.22 (m, 2H), 7.21-7.14 (m, 2H), 6.45 (s, 1H), 3.65-3.59 (m, 2H), 3.05-2.97 (m, 2H), 2.90 (s, 3H)

LC/MS ESI (+): 376 (M+1)

Example 8: Synthesis of 2-chloro-8-ethyl-N-(4-nitrophenethyl)quinolin-4-amine

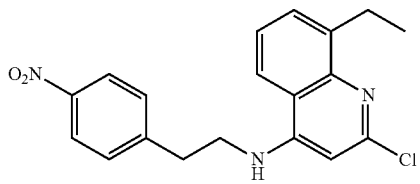 [SMILES: CCc1cccc2c(NCCc3ccc([N+](=O)[O-])cc3)cc(Cl)nc12]

With 2,4-dichloro-8-ethylquinoline (200.0 mg, 0.88 mmol) as a starting material, the same synthesis procedures as Example 5 were carried out to obtain the white solid compound, 2-chloro-8-ethyl-N-(4-nitrophenethyl)quinolin-4-amine (20.0 mg, 6%).

$^1$H NMR (300 MHz, CDCl$_3$) δ=8.22 (d, J=8.7 Hz, 2H), 7.53 (t, J=4.3 Hz, 1H), 7.43-7.35 (m, 4H), 6.48 (s, 1H), 5.02 (br s, 1H), 3.68-3.64 (m, 2H), 3.22-3.15 (m, 4H), 1.34 (t, J=7.4 Hz, 3H)

LC/MS ESI (+): 356 (M+1)

Example 9: Synthesis of 2-chloro-6-methoxy-N-(4-nitrophenethyl)quinolin-4-amine

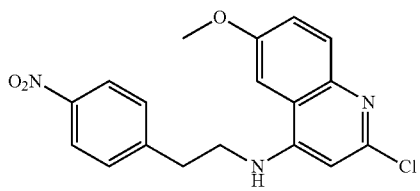 [SMILES: COc1ccc2nc(Cl)cc(NCCc3ccc([N+](=O)[O-])cc3)c2c1]

With 2,4-dichloro-6-methoxyquinoline (200.0 mg, 0.88 mmol) as a starting material, the same synthesis procedures as Example 5 were carried out to obtain the white solid compound, 2-chloro-6-methoxy-N-(4-nitrophenethyl)quinolin-4-amine (20.0 mg, 6%).

$^1$H NMR (300 MHz, CDCl$_3$) δ=8.22 (d, J=8.7 Hz, 2H), 7.85 (d, J=8.4 Hz, 1H), 7.43-7.30 (m, 3H), 6.76 (s, 1H), 6.47 (s, 1H), 4.88-4.84 (m, 1H), 3.88 (s, 3H), 3.71-3.64 (m, 2H), 3.19 (t, J=7.4 Hz, 2H)

LC/MS ESI (+): 358 (M+1)

Example 10: Synthesis of 2-chloro-8-methoxy-N-(4-nitrophenethyl)quinolin-4-amine

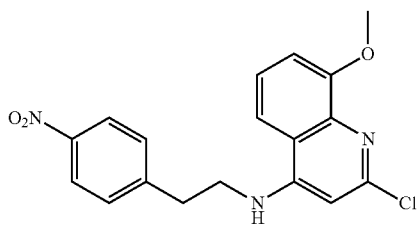 [SMILES: COc1cccc2c(NCCc3ccc([N+](=O)[O-])cc3)cc(Cl)nc12]

With 2,4-dichloro-8-methoxyquinoline (200.0 mg, 0.88 mmol) as a starting material, the same synthesis procedures as Example 5 were carried out to obtain the white solid compound, 2-chloro-8-methoxy-N-(4-nitrophenethyl)quinolin-4-amine (15.0 mg, 5%).

$^1$H NMR (300 MHz, CDCl$_3$) δ=8.21 (d, J=8.7 Hz, 2H), 7.43-7.32 (m, 3H), 7.08-7.02 (m, 2H), 6.52 (s, 1H), 5.04 (br s, 1H), 4.03 (s, 3H), 3.70-3.63 (m, 2H), 3.18 (t, J=6.8 Hz, 2H)

LC/MS ESI (+): 358 (M+1)

Example 11: Synthesis of N-(4-(2-((2-chloro-6-methoxyquinolin-4-yl)amino)ethyl)phenyl)methanesulfonamide

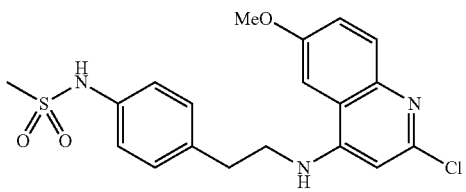 [SMILES: COc1ccc2nc(Cl)cc(NCCc3ccc(NS(C)(=O)=O)cc3)c2c1]

(a) Synthesis of N-(4-aminophenethyl)-2-chloro-6-methoxyquinolin-4-amine

2-Chloro-6-methoxy-N-(4-nitrophenethyl)quinolin-4-amine (40.0 mg, 0.11 mmol) was dissolved in MeOH (2.0 mL), and 5% palladium on activated carbon (4 mg, 10 w/w %) was added thereto. The reaction mixture was charged with H$_2$ gas and stirred at room temperature for 2 hours. The reaction mixture was filtered with celite and distilled under reduced pressure. The residue was purified by column chromatography (CH$_2$Cl$_2$) on amine silica. The fractions containing the product were collected and evaporated to obtain the white compound, N-(4-aminophenethyl)-2-chloro-6-methoxyquinolin-4-amine (12.2 mg, 32%).

LC/MS ESI (+): 328 (M+1)

(b) Synthesis of N-(4-(2-((2-chloro-6-methoxyquinolin-4-yl)amino)ethyl)phenyl)methanesulfonamide N-(4-aminophenethyl)-2-chloro-6-methoxyquinolin-4-amine (12.2 mg, 0.04 mmol) was dissolved in pyridine (3.0 mL), and MsCl (6.0 μL, 0.07 mmol) was slowly added thereto at 0° C. After termination of the reaction, the reaction mixture was extracted with CH$_2$Cl$_2$. The organic layer was washed with brine, dried with Na$_2$SO$_4$, filtered and distilled under reduced pressure. The residue was purified by column chromatography (CH$_2$Cl$_2$:MeOH=20:1) on silica. The fractions containing the product were collected and evaporated to obtain the white solid compound, N-(4-(2-((2-chloro-6-methoxyquinolin-4-yl)amino)ethyl)phenyl)methanesulfonamide (9.0 mg, 60%).

$^1$H NMR (300 MHz, DMSO-d$_6$) δ=9.61 (s, 1H), 7.63-7.56 (m, 2H), 7.43 (br s, 1H), 7.32-7.26 (m, 3H), 7.14 (d, J=8.4 Hz, 2H), 6.42 (s, 1H), 3.87 (s, 3H), 3.54-3.47 (m, 2H), 2.96-2.90 (m, 5H)

LC/MS ESI (+): 406 (M+1)

Example 12: Synthesis of 2-chloro-N-(4-nitrophenethyl)-7-(trifluoromethoxy)quinolin-4-amine

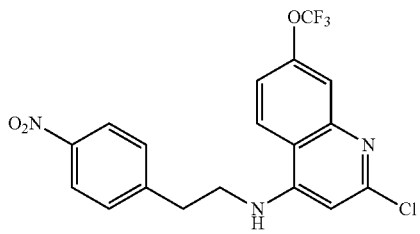 [SMILES: O=[N+]([O-])c1ccc(CCNc2cc(Cl)nc3cc(OC(F)(F)F)ccc23)cc1]

With 2,4-dichloro-7-(trifluoromethoxy)quinoline (200.0 mg, 0.71 mmol) as a starting material, the same synthesis procedures as Example 5 were carried out to obtain the white solid compound, 2-chloro-N-(4-nitrophenethyl)-7-(trifluoromethoxy)quinolin-4-amine (60.0 mg, 21%).

$^1$H NMR (300 MHz, DMSO-$d_6$)=8.33 (d, J=9.3 Hz, 1H), 8.17 (d, J=8.7 Hz, 2H), 7.80 (br s, 1H), 7.61-7.57 (m, 3H), 7.51-7.47 (m, 1H), 6.58 (s, 1H), 3.66-3.60 (m, 2H), 3.12 (t, J=6.9 Hz, 2H),

LC/MS ESI (+): 412 (M+1)

Example 13: Synthesis of 2-chloro-N-(4-nitrophenethyl)-5-(trifluoromethoxy)quinolin-4-amine

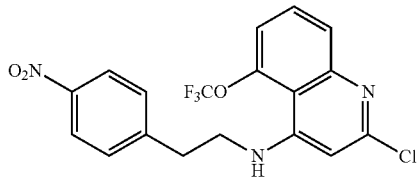 [SMILES: O=[N+]([O-])c1ccc(CCNc2cc(Cl)nc3cccc(OC(F)(F)F)c23)cc1]

With 2,4-dichloro-5-(trifluoromethoxy)quinoline (115.0 mg, 0.41 mmol) as a starting material, the same synthesis procedures as Example 5 were carried out to obtain the white solid compound, 2-chloro-N-(4-nitrophenethyl)-5-(trifluoromethoxy)quinolin-4-amine (49.0 mg, 29%).

$^1$H NMR (300 MHz, DMSO-$d_6$) δ=8.18 (d, J=8.7 Hz, 2H), 7.74-7.66 (m, 2H), 7.62 (d, J=8.8 Hz, 2H), 7.42-7.39 (m, 1H), 6.96 (br s, 1H), 6.68 (s, 1H), 3.70-3.63 (m, 2H), 3.14 (t, J=6.9 Hz, 2H).

LC/MS ESI (+): 412 (M+1)

Example 14: Synthesis of 2-chloro-6-fluoro-N-(4-nitrophenethyl)quinolin-4-amine

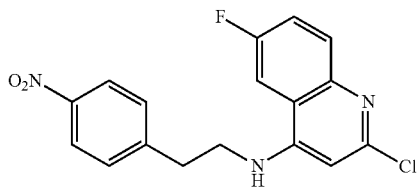 [SMILES: O=[N+]([O-])c1ccc(CCNc2cc(Cl)nc3ccc(F)cc23)cc1]

2,4-Dichloro-6-fluoroquinoline (200.0 mg, 0.93 mmol), 2-(4-nitrophenyl)ethan-1-amine hydrochloride (188.0 mg, 0.93 mmol) and Et$_3$N (390.0 μL, 2.79 mmol) were added to NMP (3.1 mL). The reaction mixture was reacted in a microwave (50 W, 100° C.) for 1 hour and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (n-Hex:EtOAc=1:1) on silica. The fractions containing the product were collected and evaporated to obtain the white solid compound, 2-chloro-6-fluoro-N-(4-nitrophenethyl)quinolin-4-amine (45.0 mg, 14%).

$^1$H NMR (300 MHz, CDCl$_3$) δ=8.27-8.17 (m, 2H), 7.96-7.86 (m, 1H), 7.49-7.36 (m, 3H), 7.17 (dd, J=2.7, 9.5 Hz, 1H), 6.49 (s, 1H), 4.91 (t, J=4.8 Hz, 1H), 3.73-3.63 (m, 2H), 3.19 (t, J=7.1 Hz, 2H)

LC/MS ESI (+): 346 (M+1)

Example 15: Synthesis of 2-chloro-8-methyl-N-(4-nitrophenethyl)quinolin-4-amine

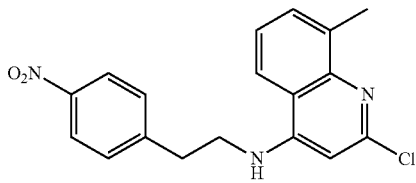 [SMILES: Cc1cccc2c(NCCc3ccc([N+](=O)[O-])cc3)cc(Cl)nc12]

2,4-Dichloro-8-methylquinoline (200.0 mg, 0.94 mmol), 2-(4-nitrophenyl)ethan-1-amine hydrochloride (188.0 mg, 0.94 mmol) and Et$_3$N (390.0 μL, 2.82 mmol) were added to NMP (3.1 mL). The reaction mixture was reacted in a microwave (50 W, 100° C.) for 1 hour and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (n-Hex:EtOAc=1:1) on silica. The fractions containing the product were collected and evaporated to obtain the white solid compound, 2-chloro-8-methyl-N-(4-nitrophenethyl)quinolin-4-amine (10.0 mg, 3%).

$^1$H NMR (300 MHz, CDCl$_3$) δ=8.26-8.15 (m, 2H), 7.56-7.48 (m, 1H), 7.45-7.28 (m, 4H), 6.48 (s, 1H), 5.05 (t, J=5.3 Hz, 1H), 3.72-3.60 (m, 2H), 3.18 (t, J=6.9 Hz, 2H), 2.72 (s, 3H)

LC/MS ESI (+): 342 (M+1)

Example 16: Synthesis of ethyl 2-chloro-4-((4-nitrophenethyl)amino)quinolin-6-carboxylate

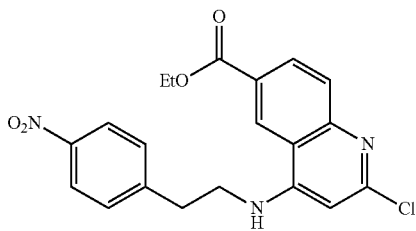

Ethyl 2,4-dichloroquinolin-6-carboxylate (200.0 mg, 0.74 mmol), 2-(4-nitrophenyl)ethan-1-amine hydrochloride (150.0 mg, 0.74 mmol) and Et$_3$N (310.0 μL, 2.22 mmol) were added to NMP (2.5 mL). The reaction mixture was reacted in a microwave (50 W, 100° C.) for 1 hour and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (n-Hex:EtOAc=1:1) on silica. The fractions containing the product were collected and evaporated to obtain the white solid compound, ethyl 2-chloro-4-((4-nitrophenethyl)amino)quinolin-6-carboxylate (30.0 mg, 10%).

$^1$H NMR (300 MHz, DMSO-d$_6$) δ=8.89 (d, J=1.5 Hz, 1H), 8.21-8.06 (m, 4H), 7.75 (d, J=8.8 Hz, 1H), 7.64-7.56 (m, 2H), 6.60 (s, 1H), 4.38 (q, J=7.0 Hz, 2H), 3.64 (q, J=6.6 Hz, 2H), 3.13 (t, J=7.2 Hz, 2H), 1.36 (t, J=7.2 Hz, 3H)

LC/MS ESI (+): 400 (M+1)

Example 17: Synthesis of N-(4-nitrophenethyl)quinolin-4-amine

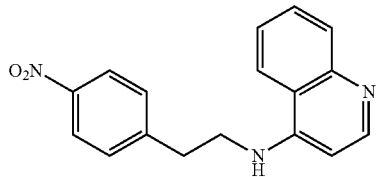 [SMILES: O=[N+]([O-])c1ccc(CCNc2ccnc3ccccc23)cc1]

4-Chloroquinoline (300.0 mg, 1.83 mmol), 2-(4-nitrophenyl)ethan-1-amine hydrochloride (371.0 mg, 1.83 mmol) and Et$_3$N (760.0 μL, 5.49 mmol) were added to NMP (6.0 mL). The reaction mixture was reacted in a microwave (50 W, 100° C.) for 1 hour and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (CH$_2$Cl$_2$) on silica. The fractions containing the product were collected and evaporated to obtain the white solid compound, N-(4-nitrophenethyl)quinolin-4-amine (5.0 mg, 1%).

$^1$H NMR (300 MHz, DMSO-d$_6$) δ=8.45-8.37 (m, 1H), 8.22-8.12 (m, 3H), 7.77 (dd, J=0.8, 8.4 Hz, 1H), 7.65-7.56 (m, 3H), 7.41 (ddd, J=1.1, 7.0, 8.3 Hz, 1H), 7.25 (t, J=5.5 Hz, 1H), 6.55 (d, J=5.3 Hz, 1H), 3.58 (q, J=6.9 Hz, 2H), 3.13 (t, J=7.2 Hz, 2H)

LC/MS ESI (+): 294 (M+1)

Example 18: Synthesis of 2-chloro-N-(4-nitrophenethyl)quinazolin-4-amine

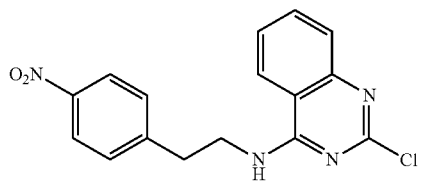

2,4-Dichloroquinazoline (100.0 mg, 0.50 mmol) and 2-(4-nitrophenyl)ethan-1-amine hydrochloride (102.0 mg, 0.50 mmol) were dissolved in THF (5.0 mL) and cooled to 0° C., and Et$_3$N (140.0 μL, 1.0 mmol) was added thereto. The reaction mixture was stirred at 25° C. for 5 hours and evaporated under reduced pressure. The residue was extracted with CH$_2$Cl$_2$. The organic layer was washed with brine, dried with Na$_2$SO$_4$, filtered and distilled under reduced pressure. The residue was purified by column chromatography (CH$_2$Cl$_2$) on amine silica. The fractions containing the product were collected and evaporated to obtain the white solid compound, 2-chloro-N-(4-nitrophenethyl)quinazolin-4-amine (50.0 mg, 30%).

$^1$H NMR (300 MHz, CDCl$_3$) δ=8.20 (d, J=8.8 Hz, 2H), 7.84-7.71 (m 2H), 7.60-7.54 (m, 1H), 7.51-7.40 (m, 3H), 6.05-5.93 (m, 1H), 4.00 (q, J=6.9 Hz, 2H), 3.19 (t, J=7.1 Hz, 2H)

LC/MS ESI (+): 329 (M+1)

Example 19: Synthesis of 2-chloro-N-(4-nitrophenethyl)-4-((4-nitrophenethyl)amino)quinolin-6-sulfonamide

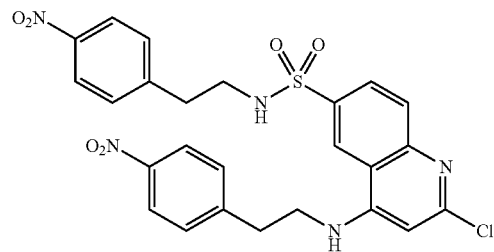 [SMILES: O=[N+]([O-])c1ccc(CCNc2cc(Cl)nc3ccc(S(=O)(=O)NCCc4ccc([N+](=O)[O-])cc4)cc23)cc1]

2,4-Dichloroquinolin-6-sulfonamide (200.0 mg, 0.72 mmol), 2-(4-nitrophenyl)ethan-1-amine hydrochloride (146.0 mg, 0.72 mmol) and Et$_3$N (302.0 μL, 2.17 mmol) were added to NMP (4.0 mL). The reaction mixture was reacted in a microwave (50 W, 100° C.) for 1 hour and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (n-Hex:CH$_2$Cl$_2$=1:2) on silica. The fractions containing the product were collected and evaporated to obtain the white solid compound, 2-chloro-N-(4-nitrophenethyl)-4-((4-nitrophenethyl)amino)quinolin-6-sulfonamide (4.0 mg, 1%).

$^1$H NMR (300 MHz, DMSO-d$_6$)=8.19-8.11 (m, 3H), 7.98 (d, J=8.7 Hz, 2H), 7.81-7.72 (m, 3H), 7.61-7.56 (m, 3H), 7.37 (d, J=8.7 Hz, 2H), 7.30 (s, 1H), 3.73-3.66 (m, 2H), 3.12-3.04 (m, 4H), 2.79 (t, J=6.7 Hz, 2H).

LC/MS ESI (+): 556 (M+1)

Example 20: Synthesis of 2-chloro-N-(4-nitrosophenethyl)quinolin-4-amine

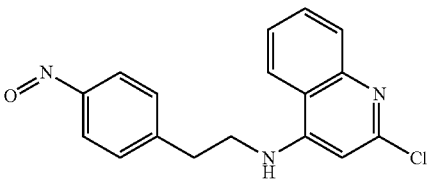 [SMILES: O=Nc1ccc(CCNc2cc(Cl)nc3ccccc23)cc1]

2-Chloro-N-(4-nitrophenethyl)quinolin-4-amine (135.0 mg, 0.41 mmol) was dissolved in MeOH (4.0 mL), and 5% palladium on activated carbon (13 mg, 10 w/w %) was added thereto. The reaction mixture was charged with H₂ gas and stirred at room temperature for 3 hours. The reaction mixture was filtered with celite and distilled under reduced pressure. The residue was purified by column chromatography (CH₂Cl₂) on amine silica. The fractions containing the product were collected and evaporated to obtain the white solid compound, 2-chloro-N-(4-nitrosophenethyl)quinolin-4-amine (2.3 mg, 2%).

¹H NMR (300 MHz, DMSO-d₆) δ=8.20-8.14 (m, 1H), 7.93-7.86 (m, 2H), 7.73-7.58 (m, 5H), 7.42 (d, J=0.8 Hz, 1H), 6.52 (s, 1H), 3.71-3.56 (m, 2H), 3.17-3.08 (m, 2H)

LC/MS ESI (+): 312 (M+1)

Example 21: Synthesis of N-(4-(2-((6-fluoroquinolin-4-yl)amino)ethyl)phenyl)methanesulfonamide

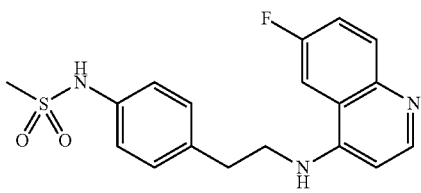 [SMILES: CS(=O)(=O)Nc1ccc(CCNc2ccnc3ccc(F)cc23)cc1]

(a) Synthesis of N-(4-aminophenethyl)-6-fluoroquinolin-4-amine

2-Chloro-6-fluoro-N-(4-nitrophenethyl)quinolin-4-amine (50.0 mg, 0.14 mmol) was dissolved in MeOH (2.0 mL), and 5% palladium on activated carbon (5 mg, 10 w/w %) was added thereto. The reaction mixture was charged with H₂ gas and stirred at room temperature for 1 hour. The reaction mixture was filtered with celite and distilled under reduced pressure. The residue was purified by column chromatography (CH₂Cl₂) on amine silica. The fractions containing the product were collected and evaporated to obtain the white solid compound, N-(4-aminophenethyl)-6-fluoroquinolin-4-amine (30.0 mg, 76%).

LC/MS ESI (+): 282 (M+1)

(b) Synthesis of N-(4-(2-((6-fluoroquinolin-4-yl)amino)ethyl)phenyl)methanesulfonamide N-(4-aminophenethyl)-6-fluoroquinolin-4-amine (30.0 mg, 0.11 mmol) was dissolved in pyridine (1.1 mL), and MsCl (17.0 μL, 0.21 mmol) was slowly added thereto at 26° C. After termination of the reaction, the reaction mixture was extracted with CH₂Cl₂. The organic layer was washed with brine, dried with Na₂SO₄, filtered and evaporated under reduced pressure. The residue was purified by column chromatography (CH₂Cl₂:MeOH=20:1) on silica. The fractions containing the product were collected and evaporated to obtain the white solid compound, N-(4-(2-((6-fluoroquinolin-4-yl)amino)ethyl)phenyl)methanesulfonamide (12.0 mg, 31%).

¹H NMR (300 MHz, DMSO-d₆) δ=9.82-9.70 (m, 1H), 8.54 (d, J=5.7 Hz, 1H), 8.32 (d, J=11.1 Hz, 1H), 8.03 (dd, J=5.7, 9.2 Hz, 2H), 7.82-7.69 (m, 1H), 7.45-7.35 (m, 2H), 7.26 (d, J=8.4 Hz, 2H), 6.76 (d, J=5.7 Hz, 1H), 3.74-3.64 (m, 2H), 3.14-3.01 (m, 5H)

LC/MS ESI (+): 360 (M+1)

Example 22: Synthesis of N-(4-(2-((2-chloro-6-fluoroquinolin-4-yl)amino)ethyl)phenyl)methanesulfonamide

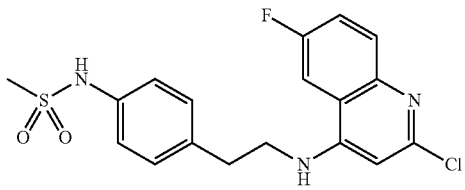 [SMILES: CS(=O)(=O)Nc1ccc(CCNc2cc(Cl)nc3ccc(F)cc23)cc1]

With 2-chloro-6-fluoro-N-(4-nitrophenethyl)quinolin-4-amine (50.0 mg, 0.14 mmol) as a starting material, the same synthesis procedures as Example 21 were carried out to obtain the white solid compound, N-(4-2-((2-chloro-6-fluoroquinolin-4-yl)amino)ethyl)phenyl)methanesulfonamide (15.0 mg, 27%: 2 steps).

¹H NMR (300 MHz, DMSO-d₆) δ=9.67-9.56 (m, 1H), 8.07 (dd, J=2.5, 10.9 Hz, 1H), 7.76 (dd, J=5.7, 9.2 Hz, 1H), 7.62-7.44 (m, 2H), 7.33-7.22 (m, 2H), 7.14 (d, J=8.0 Hz, 2H), 6.48 (s, 1H), 3.51 (q, J=6.2 Hz, 2H), 2.99-2.88 (m, 5H)

LC/MS ESI (+): 394 (M+1)

Example 23: Synthesis of N-(4-(2-((2-chloroquinazolin-4-yl)amino)ethyl)phenyl)methanesulfonamide

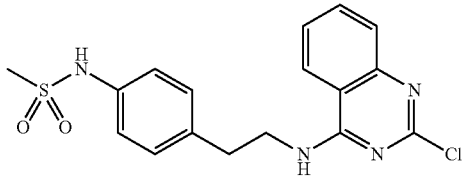 [SMILES: CS(=O)(=O)Nc1ccc(CCNc2nc(Cl)nc3ccccc23)cc1]

With 2-chloro-N-(4-nitrophenethyl)quinazolin-4-amine (50.0 mg, 0.14 mmol) as a starting material, the same synthesis procedures as Example 21 were carried out to obtain the white solid compound, N-(4-(2-((2-chloroquinazolin-4-yl)amino)ethyl)phenyl)methanesulfonamide (10.0 mg, 17%: 2 steps).

¹H NMR (300 MHz, DMSO-d₆) δ=9.66-9.56 (m, 1H), 8.83 (t, J=5.5 Hz, 1H), 8.22 (d, J=8.0 Hz, 1H), 7.85-7.75 (m, 1H), 7.64-7.58 (m, 1H), 7.53 (dt, J=1.1, 7.6 Hz, 1H), 7.28-7.20 (m, 2H), 7.17-7.10 (m, 2H), 3.78-3.65 (m, 2H), 2.98-2.87 (m, 5H)

LC/MS ESI (+): 377 (M+1)

Example 24: Synthesis of N-(4-(2-((2-chloro-7-(trifluoromethoxy)quinolin-4-yl)amino)ethyl)phenyl)methanesulfonamide

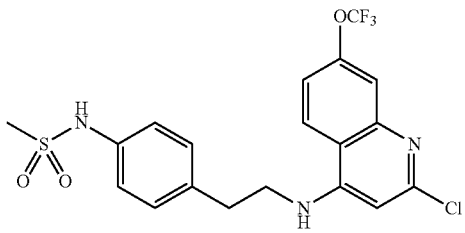 [SMILES: CS(=O)(=O)Nc1ccc(CCNc2cc(Cl)nc3cc(OC(F)(F)F)ccc23)cc1]

(a) Synthesis of N-(4-aminophenethyl)-2-chloro-7-(trifluoromethoxy)quinolin-4-amine 2-Chloro-N-(4-nitrophenethyl)-7-(trifluoromethoxy)quinolin-4-amine (52.0 mg, 0.13 mmol) was dissolved in MeOH (4.0 mL), and 5% palladium on activated carbon (8 mg, 15 w/w %) was added thereto. The reaction mixture was charged with $H_2$ gas and stirred at room temperature for 2 hours. The reaction mixture was filtered with celite and distilled under reduced pressure. The residue was purified by column chromatography ($CH_2Cl_2$:MeOH=20:1) on amine silica. The fractions containing the product were collected and evaporated to obtain the white solid compound, N-(4-aminophenethyl)-2-chloro-7-(trifluoromethoxy)quinolin-4-amine (9.0 mg, 18%).

LC/MS ESI (+): 382 (M+1)

(b) Synthesis of N-(4-(2-((2-chloro-7-(trifluoromethoxy)quinolin-4-yl)amino)ethyl)phenyl)methanesulfonamide N-(4-aminophenethyl)-2-chloro-7-(trifluoromethoxy)quinolin-4-amine (9.0 mg, 0.11 mmol) was dissolved in pyridine (1.5 mL), and MsCl (4.0 µL, 0.05 mmol) was slowly added thereto at 26° C. After termination of the reaction, the reaction mixture was extracted with $CH_2Cl_2$. The organic layer was washed with brine, dried with $Na_2SO_4$, filtered and evaporated under reduced pressure. The residue was purified by column chromatography (EtOAc) on amine silica. The fractions containing the product were collected and evaporated to obtain the white solid compound, N-(4-(2-((2-chloro-7-(trifluoromethoxy)quinolin-4-yl)amino)ethyl)phenyl)methanesulfon amide (7.9 mg, 73%).

$^1$H NMR (300 MHz, DMSO-$d_6$) δ=8.06 (d, J=9.3 Hz, 1H), 7.64 (s, 1H), 7.27-7.18 (m, 6H), 6.81 (br s, 1H), 6.38 (s, 1H), 3.57-3.50 (m, 2H), 3.03 (t, J=7.3 Hz, 2H), 2.93 (s, 3H)

LC/MS ESI (+): 460 (M+1)

Example 25: Synthesis of N-(4-(2-((7-(trifluoromethoxy)quinolin-4-yl)amino)ethyl)phenyl)methanesulfonamide

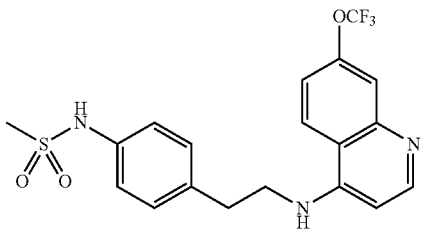 [SMILES: CS(=O)(=O)Nc1ccc(CCNc2ccnc3cc(OC(F)(F)F)ccc23)cc1]

(a) Synthesis of N-(4-aminophenethyl)-7-(trifluoromethoxy)quinolin-4-amine

2-Chloro-N-(4-nitrophenethyl)-7-(trifluoromethoxy)quinolin-4-amine (52.0 mg, 0.13 mmol) was dissolved in MeOH (4.0 mL), and 5% palladium on activated carbon (8 mg, 15 w/w %) was added thereto. The reaction mixture was charged with $H_2$ gas and stirred at room temperature for 2 hours. The reaction mixture was filtered with celite and distilled under reduced pressure. The residue was purified by column chromatography ($CH_2Cl_2$:MeOH=20:1) on amine silica. The fractions containing the product were collected and evaporated to obtain the white solid compound, N-(4-aminophenethyl)-7-(trifluoromethoxy)quinolin-4-amine (28.9 mg, 66%).

LC/MS ESI (+): 348 (M+1)

(b) Synthesis of N-(4-(2-((7-trifluoromethoxy)quinolin-4-yl)amino)ethyl)phenyl)methanesulfonamide N-(4-aminophenethyl)-7-(trifluoromethoxy)quinolin-4-amine (28.9 mg, 0.08 mmol) was dissolved in pyridine (3.0 mL), and MsCl (13.0 µL, 0.16 mmol) was slowly added thereto at 24° C. After termination of the reaction, the reaction mixture was extracted with $CH_2Cl_2$. The organic layer was washed with brine, dried with $Na_2SO_4$, filtered and evaporated under reduced pressure. The residue was purified by column chromatography ($CH_2Cl_2$:MeOH=20:1) on amine silica. The fractions containing the product were collected and evaporated to obtain the white solid compound, N-(4-(2-((7-(trifluoromethoxy)quinolin-4-yl)amino)ethyl)phenyl)methanesulfonamide (9.3 mg, 26%).

$^1$H NMR (300 MHz, DMSO-$d_6$) δ=9.62 (s, 1H), 8.43 (d, J=5.4 Hz, 1H), 8.35 (d, J=9.3 Hz, 1H), 7.64 (s, 1H), 7.50-7.40 (m, 2H), 7.27 (d, J=8.3 Hz, 2H), 7.13 (d, J=8.3 Hz, 2H), 6.57 (d, J=5.5 Hz, 1H), 3.66-3.46 (m, 2H), 2.95-2.90 (m, 5H),

LC/MS ESI (+): 426 (M+1)

Example 26: Synthesis of N-(4-(2-((2-chloro-5-(trifluoromethoxy)quinolin-4-yl)amino)ethyl)phenyl)methanesulfonamide

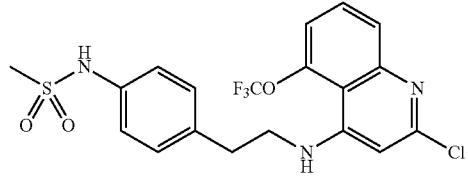 [SMILES: CS(=O)(=O)Nc1ccc(CCNc2cc(Cl)nc3cccc(OC(F)(F)F)c23)cc1]

With 2-chloro-N-(4-nitrophenethyl)-5-(trifluoromethoxy)quinolin-4-amine (49.0 mg, 0.12 mmol) as a starting material, the same synthesis procedures as Example 24 were carried out to obtain the white solid compound, N-(4-(2-((2-chloro-5-(trifluoromethoxy)quinolin-4-yl)amino)ethyl)phenyl)methanesulfon amide (17.3 mg, 32%: 2 steps).

$^1$H NMR (300 MHz, CDCl$_3$) δ=7.80 (d, J=8.4 Hz, 1H), 7.55 (t, J=8.4 Hz, 1H), 7.29-7.19 (m, 5H), 6.58 (br s, 1H), 6.42 (s, 1H), 6.33 (s, 1H), 3.57-3.50 (m, 2H), 3.07-3.00 (m, 5H)

LC/MS ESI (+): 460 (M+1)

Example 27: Synthesis of N-(4-(2-((5-(trifluoromethoxy)quinolin-4-yl)amino)ethyl)phenyl)methanesulfonamide

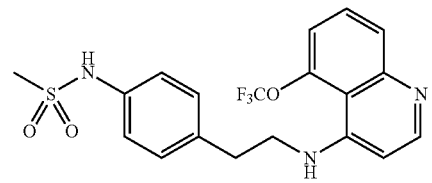 [SMILES: CS(=O)(=O)Nc1ccc(CCNc2ccnc3cccc(OC(F)(F)F)c23)cc1]

With 2-chloro-N-(4-nitrophenethyl)-5-(trifluoromethoxy) quinolin-4-amine (49.0 mg, 0.12 mmol) as a starting material, the same synthesis procedures as Example 25 were carried out to obtain the white solid compound, N-(4-(2-((5-(trifluoromethoxy)quinolin-4-yl)amino)ethyl)phenyl) methanesulfonamide (11.7 mg, 23%: 2 steps).

$^1$H NMR (300 MHz, DMSO-d$_6$) δ=9.63 (s, 1H), 8.45 (d, J=5.4 Hz, 1H), 7.80 (d, J=7.3 Hz, 1H), 7.63 (t, J=8.4 Hz, 1H), 7.37-7.27 (m, 3H), 7.16 (d, J=8.4 Hz, 2H), 6.66 (d, J=5.6 Hz, 1H), 6.60 (br s, 1H), 3.55-3.48 (m, 2H), 2.97-2.93 (m, 5H)

LC/MS ESI (+): 426 (M+1)

Example 28: Synthesis of 2-chloro-6-morpholino-N-(4-nitrophenethyl)quinolin-4-amine 2,2,2-trifluoroacetate

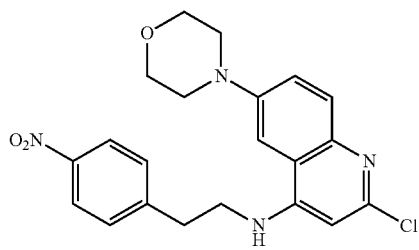 [SMILES: O=[N+]([O-])c1ccc(CCNc2cc(Cl)nc3ccc(N4CCOCC4)cc23)cc1]

With 4-(2,4-dichloroquinolin-6-yl)morpholine (70.0 mg, 0.25 mmol) as a starting material, the same synthesis procedures as Example 5 were carried out to obtain the white solid compound, 2-chloro-6-morpholino-N-(4-nitrophenethyl)quinolin-4-amine 2,2,2-trifluoroacetate (4.0 mg, 3%).

$^1$H NMR (300 MHz, DMSO-d$_6$) δ=11.70 (br s, 1H), 8.17 (d, J=8.6 Hz, 2H), 7.64-7.49 (m, 5H), 7.35 (s, 1H), 6.48 (s, 1H), 3.80-3.77 (m, 4H), 3.65-3.57 (m, 2H), 3.26-3.21 (m, 4H), 3.11 (t, J=7.5 Hz, 2H)

LC/MS ESI (+): 413 (M+1)

Example 29: Synthesis of 2-chloro-5-fluoro-N-(4-nitrophenethyl)quinolin-4-amine

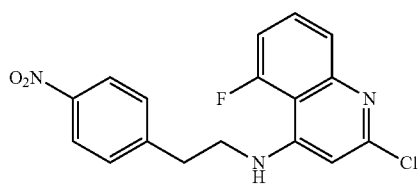 [SMILES: O=[N+]([O-])c1ccc(CCNc2cc(Cl)nc3cccc(F)c23)cc1]

2,4-Dichloro-5-fluoroquinoline (160.0 mg, 0.74 mmol), 2-(4-nitrophenyl)ethan-1-amine hydrochloride (151.0 mg, 0.74 mmol) and Et$_3$N (310.0 μL, 2.22 mmol) were added to DMA (2.0 mL). The reaction mixture was reacted in a microwaver (50 W, 100° C.) for 1 hour and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (n-Hex:EtOAc=1:1) on silica. The fractions containing the product were collected and evaporated to obtain the white solid compound, 2-chloro-5-fluoro-N-(4-nitrophenethyl)quinolin-4-amine (130.0 mg, 50%).

$^1$H NMR (300 MHz, DMSO-d$_6$) δ=8.23-8.12 (m, 2H), 7.68-7.48 (m, 4H), 7.30-7.08 (m, 2H), 6.58 (s, 1H), 3.69-3.56 (m, 2H), 3.11 (t, J=6.9 Hz, 2H)

LC/MS ESI (+): 346 (M+1)

Example 30: Synthesis of 2-chloro-7-fluoro-N-(4-nitrophenethyl)quinolin-4-amine

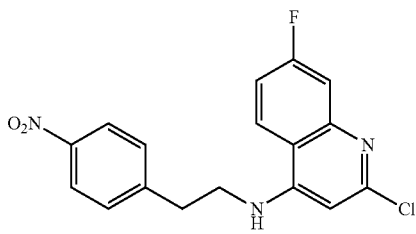 [SMILES: O=[N+]([O-])c1ccc(CCNc2cc(Cl)nc3cc(F)ccc23)cc1]

2,4-Dichloro-7-fluoroquinoline (300.0 mg, 1.40 mmol), 2-(4-nitrophenyl)ethan-1-amine hydrochloride (283.0 mg, 1.40 mmol) and Et$_3$N (585.0 μL, 4.20 mmol) were added to DMA (3.0 mL). The reaction mixture was reacted in a microwaver (50 W, 100° C.) for 1 hour and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (CH$_2$Cl$_2$) on silica. The fractions containing the product were collected and evaporated to obtain the white solid compound, 2-chloro-7-fluoro-N-(4-nitrophenethyl)quinolin-4-amine (160.0 mg, 33%).

$^1$H NMR (300 MHz, DMSO-d$_6$) δ=8.32-8.22 (m, 1H), 8.21-8.12 (m, 2H), 7.71 (t, J=5.5 Hz, 1H), 7.64-7.54 (m, 2H), 7.48-7.33 (m, 2H), 6.52 (s, 1H), 3.69-3.54 (m, 2H), 3.11 (t, J=7.1 Hz, 2H)

LC/MS ESI (+): 346 (M+1)

Example 31: Synthesis of 2-chloro-8-fluoro-N-(4-nitrophenethyl)quinolin-4-amine

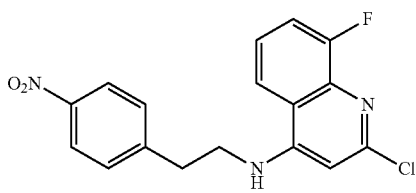 [SMILES: O=[N+]([O-])c1ccc(CCNc2cc(Cl)nc3c(F)cccc23)cc1]

2,4-Dichloro-8-fluoroquinoline (130.0 mg, 0.60 mmol), 2-(4-nitrophenyl)ethan-1-amine hydrochloride (123.0 mg, 0.60 mmol) and Et$_3$N (250.0 μL, 1.80 mmol) were added to DMA (1.5 mL). The reaction mixture was reacted in a microwaver (50 W, 100° C.) for 1 hour and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (CH$_2$Cl$_2$:MeOH=20:1) on silica. The fractions containing the product were collected and evaporated to obtain the white solid compound, 2-chloro-8-fluoro-N-(4-nitrophenethyl)quinolin-4-amine (70.0 mg, 33%).

¹H NMR (300 MHz, DMSO-d₆) δ=8.21-8.13 (m, 2H), 8.03-7.95 (m, 1H), 7.73 (t, J=5.5 Hz, 1H), 7.65-7.56 (m, 2H), 7.56-7.37 (m, 2H), 6.64-6.56 (m, 1H), 3.70-3.56 (m, 2H), 3.12 (t, J=7.1 Hz, 2H)
LC/MS ESI (+): 346 (M+1)

Example 32: Synthesis of 26-dichloro-N-(4-nitrophenethyl)quinolin-4-amine

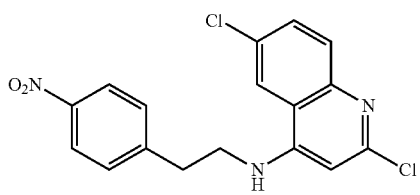

2,4,6-Trichloroquinoline (300.0 mg, 1.29 mmol), 2-(4-nitrophenyl)ethan-1-amine hydrochloride (261.0 mg, 1.29 mmol) and Et₃N (540.0 μL, 3.87 mmol) were added to DMA (3.0 mL). The reaction mixture was reacted in a microwaver (50 W, 100° C.) for 1 hour and cooled to room temperature. After addition of ice water, the reaction mixture was extracted with CH₂Cl₂. The organic layer was washed with brine, dried with Na₂SO₄ and filtered. The residue obtained under reduced pressure was purified by column chromatography (CH₂Cl₂) on silica. The fractions containing the product were collected and evaporated to obtain the white solid compound, 2,6-dichloro-N-(4-nitrophenethyl)quinolin-4-amine (180.0 mg, 38%).
¹H NMR (300 MHz, DMSO-d₆) δ=8.35 (d, J=1.5 Hz, 1H), 8.17 (d, J=8.8 Hz, 2H), 7.77-7.64 (m, 3H), 7.60 (d, J=8.8 Hz, 2H), 6.60-6.49 (m, 1H), 3.61 (q, J=6.5 Hz, 2H), 3.12 (t, J=7.1 Hz, 2H)
LC/MS ESI (+): 362 (M+1)

Example 33: Synthesis of 2-chloro-N-(4-nitrophenethyl)-6-phenoxyquinolin-4-amine

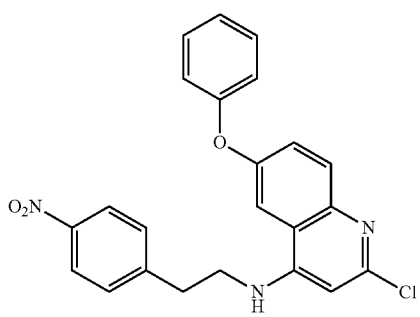 [SMILES: O=[N+]([O-])c1ccc(CCNc2cc(Cl)nc3ccc(Oc4ccccc4)cc23)cc1]

2,4-Dichloro-6-phenoxyquinoline (300.0 mg, 1.04 mmol), 2-(4-nitrophenyl)ethan-1-amine hydrochloride (210.0 mg, 1.04 mmol) and Et₃N (435.0 μL, 3.12 mmol) were added to DMA (3.0 mL). The reaction mixture was reacted in a microwaver (50 W, 100° C.) for 1 hour and cooled to room temperature. After addition of ice water, the reaction mixture was extracted with CH₂Cl₂. The organic layer was washed with brine, dried with Na₂SO₄ and filtered. The residue obtained under reduced pressure was purified by column chromatography (CH₂Cl₂:MeOH=20:1) on silica. The fractions containing the product were collected and evaporated to obtain the white solid compound, 2-chloro-N-(4-nitrophenethyl)-6-phenoxyquinolin-4-amine (60.0 mg, 14%).
¹H NMR (300 MHz, DMSO-d₆) δ=8.20-8.11 (m, 2H), 7.97-7.89 (m, 1H), 7.75 (d, J=9.2 Hz, 1H), 7.57 (d, J=8.8 Hz, 2H), 7.47 (t, J=5.3 Hz, 1H), 7.43-7.34 (m, 3H), 7.19-7.09 (m, 1H), 7.04-6.97 (m, 2H), 6.51 (s, 1H), 3.63-3.52 (m, 2H), 3.14-3.04 (m, 2H)
LC/MS ESI (+): 420 (M+1)

Example 34: Synthesis of (2-chloro-4-((4-nitrophenethyl)amino)quinolin-6-yl)(phenyl)methanone

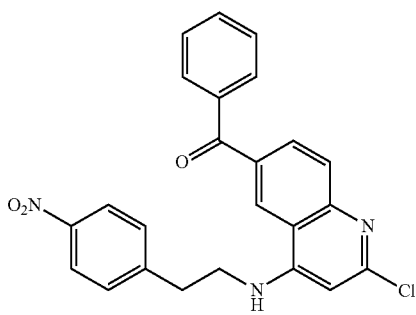 [SMILES: O=C(c1ccccc1)c1ccc2nc(Cl)cc(NCCc3ccc([N+](=O)[O-])cc3)c2c1]

(2,4-Dichloroquinolin-6-yl)(phenyl)methanone (210.0 mg, 0.70 mmol), 2-(4-nitrophenyl)ethan-1-amine hydrochloride (141.0 mg, 0.70 mmol) and Et₃N (293.0 μL, 2.10 mmol) were added to DMA (2.5 mL). The reaction mixture was reacted in a microwaver (50 W, 100° C.) for 1 hour and cooled to room temperature. After addition of ice water, the reaction mixture was extracted with CH₂Cl₂. The organic layer was washed with brine, dried with Na₂SO₄ and filtered. The residue obtained under reduced pressure was purified by column chromatography (n-Hex:EtOAc=1:1) on silica. The fractions containing the product were collected and evaporated to obtain the yellow solid compound, (2-chloro-4-((4-nitrophenethyl)amino)quinolin-6-yl)(phenyl)methanone (30.0 mg, 10%).
¹H NMR (300 MHz, DMSO-d₆) δ=8.70-8.58 (m, 1H), 8.21-8.11 (m, 2H), 8.00 (s, 1H), 7.96-7.87 (m, 1H), 7.83-7.75 (m, 3H), 7.74-7.66 (m, 1H), 7.62-7.50 (m, 4H), 6.63 (s, 1H), 3.62 (d, J=5.7 Hz, 2H), 3.09 (t, J=7.1 Hz, 2H)
LC/MS ESI (+): 432 (M+1)

Example 35: Synthesis of 2-chloro-4-((4-nitrophenethyl)amino)quinolin-6-ol

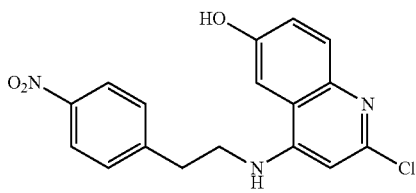 [SMILES: O=[N+]([O-])c1ccc(CCNc2cc(Cl)nc3ccc(O)cc23)cc1]

(a) Synthesis of 2-chloro-6-methoxy-N-(4-nitrophenethyl)quinolin-4-amine 2,4-Dichloro-6-methoxyquinoline (500.0 mg, 2.19 mmol), 2-(4-nitrophenyl)ethan-1-amine hydrochloride (444.0 mg, 2.19 mmol) and Et₃N (916.0 μL, 6.57 mmol) were added to DMA (4.0 mL). The reaction mixture was reacted in a microwave (50 W, 100° C.) for 1 hour and cooled to room temperature. After addition of ice water, the reaction mixture was extracted with CH₂Cl₂. The organic layer was washed with brine, dried with Na₂SO₄ and filtered. The residue obtained under reduced pressure was purified by column chromatography (CH₂Cl₂) on silica. The fractions containing the product were collected and evaporated to obtain the white solid compound, 2-chloro-6-methoxy-N-(4-nitrophenethyl)quinolin-4-amine (160.0 mg, 20%).

LC/MS ESI (+): 358 (M+1)

(b) Synthesis of 2-chloro-4-((4-nitrophenethyl)amino)quinolin-6-ol

2-Chloro-6-methoxy-N-(4-nitrophenethyl)quinolin-4-amine (95.0 mg, 0.27 mmol) was dissolved in CH₂Cl₂ (2.7 mL), and CH₂Cl₂ in which 1M BBr₃ is dissolved (0.8 mL, 0.80 mmol) was slowly added thereto at 23° C. The reaction mixture was stirred at 23° C. for 3 hours and extracted with CH₂Cl₂. The organic layer was washed with brine, dried with Na₂SO₄, filtered and distilled under reduced pressure. The residue was purified by column chromatography (CH₂Cl₂:MeOH=20:1) on silica. The fractions containing the product were collected and evaporated to obtain the ivory solid compound, 2-chloro-4-((4-nitrophenethyl)amino)quinolin-6-ol (30.0 mg, 32%).

¹H NMR (300 MHz, DMSO-d₆) δ=9.96-9.69 (m, 1H), 8.23-8.09 (m, 2H), 7.57 (dd, J=8.8, 11.4 Hz, 3H), 7.43-7.32 (m, 1H), 7.22 (dd, J=2.7, 9.2 Hz, 2H), 6.37 (s, 1H), 3.64-3.50 (m, 2H), 3.11 (t, J=7.1 Hz, 2H)

LC/MS ESI (+): 344 (M+1)

Example 36: Synthesis of N-(4-nitrophenethyl)quinazolin-4-amine

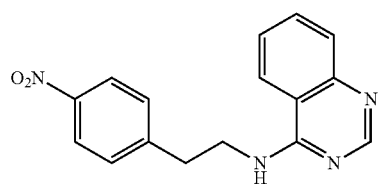 [SMILES: O=[N+]([O-])c1ccc(CCNc2ncnc3ccccc23)cc1]

4-Chloroquinazoline (100.0 mg, 0.61 mmol) and 2-(4-nitrophenyl)ethan-1-amine hydrochloride (246.0 mg, 1.22 mmol) were dissolved in EtOH (3.0 mL) and cooled to 0° C., and Et₃N (425.0 μL, 3.05 mmol) was added thereto. The reaction mixture was stirred at 80° C. for 5 hours and distilled under reduced pressure. The residue was extracted with EtOAc. The organic layer was washed with brine, dried with Na₂SO₄, filtered and distilled under reduced pressure. The residue was purified by column chromatography (CH₂Cl₂:MeOH=20:1) on silica. The fractions containing the product were collected and evaporated to obtain the white solid compound, N-(4-nitrophenethyl)quinazolin-4-amine (40.0 mg, 22%).

¹H NMR (300 MHz, DMSO-d₆) δ=8.52-8.45 (m, 1H), 8.39 (t, J=5.3 Hz, 1H), 8.22-8.13 (m, 3H), 7.80-7.72 (m, 1H), 7.71-7.65 (m, 1H), 7.61-7.45 (m, 3H), 3.82 (q, J=6.7 Hz, 2H), 3.13 (t, J=7.1 Hz, 2H)

LC/MS ESI (+): 295 (M+1)

Example 37: Synthesis of ethyl 2-((2-chloro-4-((4-nitrophenethyl)amino)quinolin-6-yl)oxy)acetate

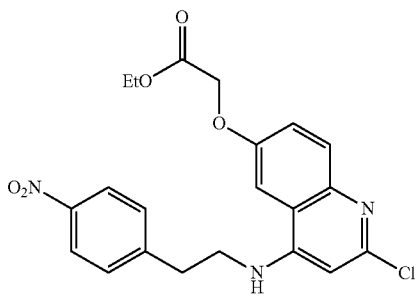 [SMILES: CCOC(=O)COc1ccc2nc(Cl)cc(NCCc3ccc([N+](=O)[O-])cc3)c2c1]

2-Chloro-4-((4-nitrophenethyl)amino)quinolin-6-ol (25.0 mg, 0.07 mmol) and ethyl 2-bromoacetate (24.0 μL, 0.22 mmol) were dissolved in acetone (2.0 mL), and K₂CO₃ (30.0 mg, 0.22 mmol) was added thereto at 22° C. The reaction mixture was stirred at 75° C. for 3 hours and distilled under reduced pressure. The reaction was terminated by the addition of water, and the reaction mixture was extracted with CH₂Cl₂. The organic layer was washed with brine, dried with Na₂SO₄, filtered and distilled under reduced pressure. The residue was purified by column chromatography (CH₂Cl₂:MeOH=20:1) on silica. The fractions containing the product were collected and evaporated to obtain the yellow solid compound, ethyl 2-((2-chloro-4-((4-nitrophenethyl)amino)quinolin-6-yl)oxy)acetate (30.0 mg, 95%).

¹H NMR (300 MHz, DMSO-d₆) δ=8.17 (d, J=8.8 Hz, 2H), 7.69-7.54 (m, 4H), 7.47-7.31 (m, 2H), 6.51-6.45 (m, 1H), 4.87 (s, 2H), 4.17 (q, J=7.0 Hz, 2H), 3.61 (q, J=6.7 Hz, 2H), 3.11 (t, J=7.1 Hz, 2H), 1.21 (t, J=7.1 Hz, 3H)

LC/MS ESI (+): 430 (M+1)

Example 38: Synthesis of N-(4-(2-(quinazolin-4-ylamino)ethyl)phenyl)methanesulfonamide

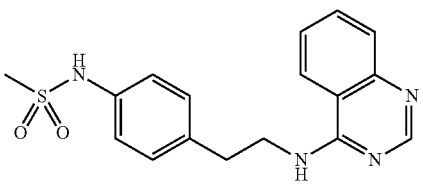 [SMILES: CS(=O)(=O)Nc1ccc(CCNc2ncnc3ccccc23)cc1]

With N-(4-nitrophenethyl)quinazolin-4-amine (40.0 mg, 0.14 mmol) as a starting material, the same synthesis procedures as Example 21 were carried out to obtain the white solid compound, N-(4-(2-(quinazolin-4-ylamino)ethyl)phenyl)methanesulfonamide (30.0 mg, 64%: 2 steps).

¹H NMR (300 MHz, DMSO-d₆) δ=9.74-9.47 (m, 1H), 8.51-8.44 (m, 1H), 8.37 (t, J=5.9 Hz, 1H), 8.20 (d, J=7.6 Hz, 1H), 7.82-7.60 (m, 2H), 7.55-7.44 (m, 1H), 7.29-7.18 (m, 2H), 7.16-7.08 (m, 2H), 3.79-3.66 (m, 2H), 2.98-2.88 (m, 5H)

LC/MS ESI (+): 343 (M+1)

Example 39: Synthesis of 2-((2-chloro-4-((4-nitrophenethyl)amino)quinolin-6-yl)oxy)acetamide

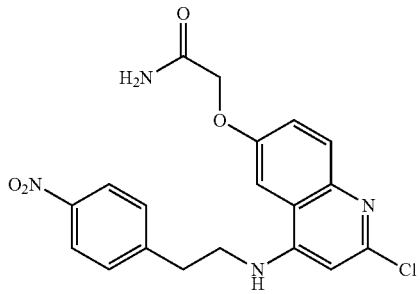 [SMILES: NC(=O)COc1ccc2nc(Cl)cc(NCCc3ccc([N+](=O)[O-])cc3)c2c1]

2-Chloro-4-((4-nitrophenethyl)amino)quinolin-6-ol (15.0 mg, 0.04 mmol) and 2-bromoacetamide (18.0 mg, 0.22 mmol) were dissolved in acetone (2.0 mL), and $K_2CO_3$ (18.0 mg, 0.13 mmol) was added thereto at room temperature. The reaction mixture was stirred at 80° C. for 3 hours and distilled under reduced pressure. The residue was extracted with $CH_2Cl_2$. The organic layer was washed with brine, dried with $Na_2SO_4$, filtered and distilled under reduced pressure. The residue was purified by column chromatography ($CH_2Cl_2$:MeOH=20:1) on silica. The fractions containing the product were collected and evaporated to obtain the yellow solid compound, 2-((2-chloro-4-((4-nitrophenethyl)amino)quinolin-6-yl)oxy)acetamide (5.0 mg, 28%).

$^1$H NMR (300 MHz, DMSO-$d_6$) δ=8.18 (d, J=8.4 Hz, 2H), 7.71-7.31 (m, 7H), 6.52-6.41 (m, 1H), 4.52 (s, 2H), 3.66-3.54 (m, 2H), 3.20-3.05 (m, 3H)

LC/MS ESI (+): 401 (M+1)

Example 40: Synthesis of 2-chloro-4-((4-nitrophenethyl)amino)quinolin-6-carboxylic acid

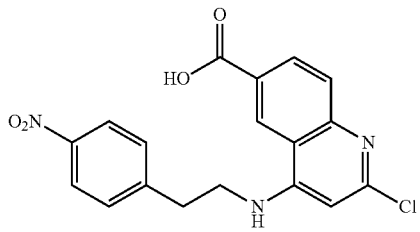 [SMILES: O=C(O)c1ccc2nc(Cl)cc(NCCc3ccc([N+](=O)[O-])cc3)c2c1]

Ethyl 2-chloro-4-((4-nitrophenethyl)amino)quinolin-6-carboxylate (27.5 mg, 0.07 mmol) was dissolved in EtOH (6.0 mL), and 1N NaOH aqueous solution (83.0 µL) was added thereto. The reaction mixture was stirred at 24° C. for 48 hours. The aqueous solution layer was acidified (pH=3) by 1N HCl aqueous solution and extracted with EtOAc. The organic layer was washed with brine, dried with $Na_2SO_4$, filtered and distilled under reduced pressure to obtain the white solid compound, 2-chloro-4-((4-nitrophenethyl)amino)quinolin-6-carboxylic acid (25.0 mg, 97%).

$^1$H NMR (300 MHz, DMSO-$d_6$) δ=13.13 (s, 1H), 8.90 (s, 1H), 8.19-8.09 (m, 4H), 7.73 (d, J=8.8 Hz, 1H), 7.60 (d, J=8.7 Hz, 2H), 6.58 (s, 1H), 3.66-3.60 (m, 2H), 3.13 (t, J=6.9 Hz, 2H)

LC/MS ESI (+): 372 (M+1)

Example 41: Synthesis of 2-chloro-4-((4-nitrophenethyl)amino)quinolin-6-carboxamide

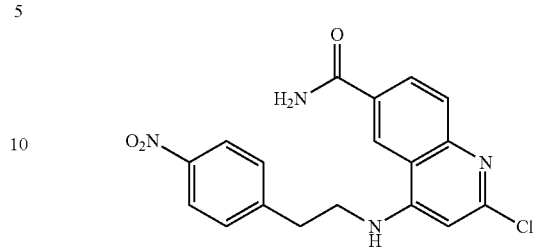

2-Chloro-4-((4-nitrophenethyl)amino)quinolin-6-carboxylic acid (16.0 mg, 0.04 mmol), $NH_4Cl$ (9.2 mg, 0.17 mmol), EDC (33.0 mg, 0.17 mmol) and HOBT (23.0 mg, 0.17 mmol) were dissolved in DMF (1.0 mL), and DIPEA (75.0 µL, 0.43 mmol) was added thereto. The reaction mixture was stirred at room temperature for 15 hours. The reaction was terminated by the addition of water, and the reaction mixture was extracted with EtOAc. The organic layer was washed with brine, dried with $Na_2SO_4$, filtered and distilled under reduced pressure. The residue was purified by column chromatography ($CH_2Cl_2$:MeOH=10:1) on silica. The fractions containing the product were collected and evaporated to obtain the white solid compound, 2-chloro-4-((4-nitrophenethyl)amino)quinolin-6-carboxamide (3.6 mg, 23%).

$^1$H NMR (300 MHz, DMSO-$d_6$) δ=8.75 (s, 1H), 8.17 (d, J=8.7 Hz, 2H), 8.07 (d, J=8.7 Hz, 1H), 7.98 (s, 1H), 7.83 (s, 1H), 7.71 (d, J=8.7 Hz, 1H), 7.62-7.56 (m, 3H), 6.56 (s, 1H), 3.67-3.60 (m, 2H), 3.14 (t, J=7.2 Hz, 2H)

LC/MS ESI (+): 371 (M+1)

Example 42: Synthesis of (2-chloro-4-((4-nitrophenethyl)amino)quinolin-6-yl)(morpholino)methanone

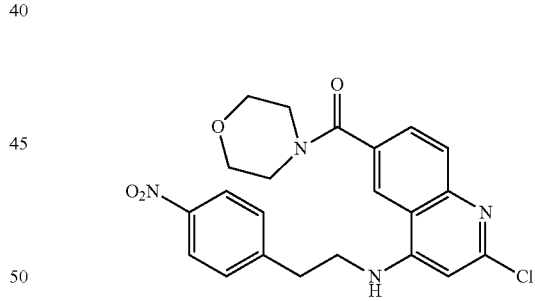

2-Chloro-4-((4-nitrophenethyl)amino)quinolin-6-carboxylic acid (40.0 mg, 0.11 mmol), morpholine (11.0 µL, 0.13 mmol), EDC (31.0 mg, 0.15 mmol) and HOBT (21.0 mg, 0.15 mmol) were dissolved in DMF (2.0 mL), and DIPEA (56.0 µL, 0.32 mmol) was added thereto. The reaction mixture was stirred at room temperature for 15 hours. The reaction was terminated by the addition of water, and the reaction mixture was extracted with EtOAc. The organic layer was washed with brine, dried with $Na_2SO_4$, filtered and distilled under reduced pressure. The residue was purified by column chromatography ($CH_2Cl_2$:MeOH=20:1) on silica. The fractions containing the product were collected and evaporated to obtain the white solid compound, (2-chloro-4-((4-nitrophenethyl)amino)quinolin-6-yl)(morpholino)methanone (20.0 mg, 42%).

¹H NMR (300 MHz, DMSO-d$_6$) δ=8.27 (s, 1H), 8.16 (d, J=8.7 Hz, 2H), 7.70-7.57 (m, 5H), 6.57 (s, 1H), 3.75-3.52 (m, 1H), 3.12 (t, J=6.7 Hz, 2H)

LC/MS ESI (+): 441 (M+1)

Example 43: Synthesis of 2-((2-chloro-4-((4-nitrophenethyl)amino)quinolin-6-yl)oxy)acetic acid

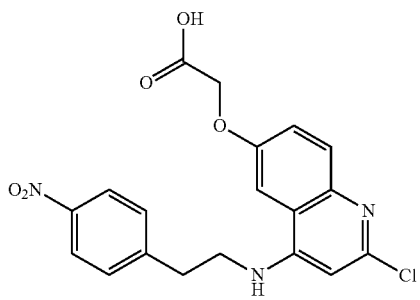 [SMILES: O=C(O)COc1ccc2nc(Cl)cc(NCCc3ccc([N+](=O)[O-])cc3)c2c1]

Ethyl 2-((2-chloro-4-((4-nitrophenethyl)amino)quinolin-6-yl)oxy)acetate (30.0 mg, 0.07 mmol) was dissolved in EtOH (5.0 mL), and 1N NaOH solution (0.21 ml, 0.21 mmol) was added thereto at 23° C. The reaction mixture was stirred at 23° C. for 3 hours and distilled under reduced pressure. The residue was extracted with CH$_2$Cl$_2$. The organic layer was washed with brine, dried with Na$_2$SO$_4$, filtered and distilled under reduced pressure. The residue was purified by column chromatography (CH$_2$Cl$_2$:MeOH=20:1) on silica. The fractions containing the product were collected and evaporated to obtain the white solid compound, 2-((2-chloro-4-((4-nitrophenethyl)amino)quinolin-6-yl)oxy)acetic acid (15.0 mg, 53%).

¹H NMR (300 MHz, DMSO-d$_6$) δ=13.39-13.07 (m, 1H), 8.18 (d, J=8.8 Hz, 2H), 7.70-7.55 (m, 4H), 7.51-7.27 (m, 2H), 6.51-6.40 (m, 1H), 4.86-4.70 (m, 2H), 3.68-3.53 (m, 2H), 3.20-3.03 (m, 2H)

LC/MS ESI (+): 402 (M+1)

Example 44: Synthesis of 2-chloro-4-((4-nitrophenethyl)amino)quinolin-6-carbohydrazide

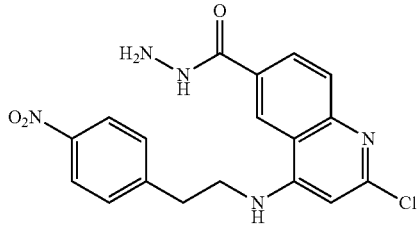 [SMILES: NNC(=O)c1ccc2nc(Cl)cc(NCCc3ccc([N+](=O)[O-])cc3)c2c1]

2-Chloro-4-((4-nitrophenethyl)amino)quinolin-6-carboxylic acid (40.0 mg, 0.11 mmol), anhydrous hydrazine (4.0 μL, 0.13 mmol), EDC (31.0 mg, 0.15 mmol) and HOBT (21.0 mg, 0.15 mmol) were dissolved in DMF (2.0 mL), and DIPEA (56.0 μL, 0.32 mmol) was added thereto. The reaction mixture was stirred at room temperature for 15 hours. The reaction was terminated by the addition of water, and the reaction mixture was extracted with EtOAc. The organic layer was washed with brine, dried with Na$_2$SO$_4$, filtered and distilled under reduced pressure. The residue was purified by column chromatography (CH$_2$Cl$_2$:MeOH=10:1) on silica. The fractions containing the product were collected and evaporated to obtain the white solid compound, 2-chloro-4-((4-nitrophenethyl)amino)quinolin-6-carbohydrazide (41.0 mg, 98%).

¹H NMR (300 MHz, DMSO-d$_6$) δ=9.77 (s, 1H), 8.70 (s, 1H), 8.17 (d, J=8.7 Hz, 2H), 8.01 (d, J=8.7 Hz, 1H), 7.94 (s, 1H), 7.70 (d, J=8.7 Hz, 1H), 7.60 (d, J=8.7 Hz, 2H), 6.56 (s, 1H), 4.57 (br s, 2H), 3.67-3.60 (m, 2H), 3.13 (t, J=7.2 Hz, 2H)

LC/MS ESI (+): 386 (M+1)

Example 45: Synthesis of N-(4-(2-((2-chloro-8-fluoroquinolin-4-yl)amino)ethyl)phenyl)methanesulfonamide

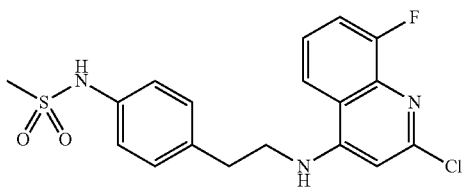 [SMILES: CS(=O)(=O)Nc1ccc(CCNc2cc(Cl)nc3c(F)cccc23)cc1]

With 2-chloro-8-fluoro-N-(4-nitrophenethyl)quinolin-4-amine (40.0 mg, 0.14 mmol) as a starting material, the same synthesis procedures as Example 21 were carried out to obtain the white solid compound, N-(4-(2-((2-chloro-8-fluoroquinolin-4-yl)amino)ethyl)phenyl)methanesulfonamide (8.0 mg, 18%: 2 steps).

¹H NMR (300 MHz, DMSO-d$_6$) δ=9.74-9.49 (m, 1H), 7.68 (d, J=8.4 Hz, 1H), 7.57-7.49 (m, 1H), 7.43 (ddd, J=1.5, 7.8, 11.3 Hz, 1H), 7.28-7.17 (m, 3H), 7.17-7.09 (m 2H), 7.05 (s, 1H), 3.59 (q, J=6.6 Hz, 2H), 2.97-2.81 (m, 5H)

LC/MS ESI (+): 394 (M+1)

Example 46: Synthesis of N-(4-(2-((8-fluoroquinolin-4-yl)amino)ethyl)phenyl)methanesulfonamide

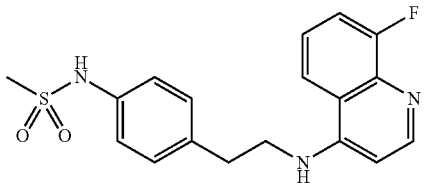 [SMILES: CS(=O)(=O)Nc1ccc(CCNc2ccnc3c(F)cccc23)cc1]

(a) Synthesis of N-(4-aminophenethyl)-8-fluoroquinolin-4-amine

2-Chloro-8-fluoro-N-(4-nitrophenethyl)quinolin-4-amine (40.0 mg, 0.12 mmol) was dissolved in MeOH (2.0 mL), and 5% palladium on activated carbon (5 mg, 12 w/w %) were added thereto. The reaction mixture was charged with H$_2$ gas and stirred at room temperature for 1 hour. The reaction mixture was filtered with celite and distilled under reduced pressure. The residue was purified by column chromatography (n-Hex:EtOAc=1:1) on amine silica. The fractions containing the product were collected and evaporated to obtain the white solid compound, N-(4-aminophenethyl)-8-fluoroquinolin-4-amine (20.0 mg, 59%).

LC/MS ESI (+): 282 (M+1)

(b) Synthesis of N-(4-(2-((8-fluoroquinolin-4-yl)amino)ethyl)phenyl)methanesulfonamide N-(4-aminophenethyl)-8-fluoroquinolin-4-amine (17.0 mg, 0.06 mmol) was dissolved in pyridine (1.0 mL), and MsCl (10.0 μL, 0.12 mmol) was slowly added thereto at 25° C. After termination of the reaction, the reaction mixture was extracted with CH$_2$Cl$_2$. The organic layer was washed with brine, dried with Na$_2$SO$_4$, filtered and distilled under reduced pressure. The residue was purified by column chromatography (CH$_2$Cl$_2$:MeOH=20:1) on amine silica. The fractions containing the product were collected and evaporated to obtain the white solid compound, N-(4-(2-((8-fluoroquinolin-4-yl)amino)ethyl)phenyl)methanesulfonamide (15.0 mg, 69%).

$^1$H NMR (300 MHz, DMSO-d$_6$) δ=9.62 (br s, 1H), 7.89 (d, J=9.2 Hz, 1H), 7.47-7.41 (m, 1H), 7.39-7.23 (m, 4H), 7.18-7.04 (m, 3H), 6.86-6.77 (m, 1H), 3.59 (q, J=6.7 Hz, 2H), 2.97-2.83 (m, 5H)

LC/MS ESI (+): 360 (M+1)

Example 47: Synthesis of 2-chloro-N-(4-nitrophenethyl)-9H-purin-6-amine

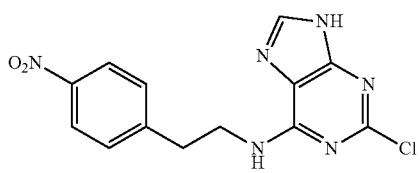 [SMILES: O=[N+]([O-])c1ccc(CCNc2nc(Cl)nc3[nH]cnc23)cc1]

2,6-Dichloro-9H-purine (100.0 mg, 0.53 mmol) and 2-(4-nitrophenyl)ethan-1-amine hydrochloride (107.0 mg, 0.53 mmol) were dissolved in THF (3.0 mL) and DMSO (2 ml), and Et$_3$N (148.0 μL, 1.06 mmol) was added thereto at 22° C. The reaction mixture was stirred at 22° C. for 3 hours and distilled under reduced pressure. After addition of CH$_2$Cl$_2$ and water, the residue was stirred. The obtained solid was filtered and dried to obtain the white solid compound, 2-chloro-N-(4-nitrophenethyl)-9H-purin-6-amine (42.0 mg, 25%).

$^1$H NMR (300 MHz, DMSO-d$_6$) δ=8.45-8.28 (m, 1H), 8.20-8.09 (m, 4H), 7.55 (d, J=8.0 Hz, 2H), 3.70 (br s, 2H), 3.07 (t, J=6.9 Hz, 2H)

LC/MS ESI (+): 319 (M+1)

Example 48: Synthesis of N-(4-nitrophenethyl)-2-(trifluoromethyl)quinazolin-4-amine

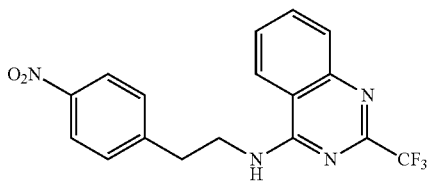 [SMILES: O=[N+]([O-])c1ccc(CCNc2nc(C(F)(F)F)nc3ccccc23)cc1]

4-chloro-2-(trifluoromethyl)quinazoline (100.0 mg, 0.43 mmol) and 2-(4-nitrophenyl)ethan-1-amine hydrochloride (87.0 mg, 0.43 mmol) were dissolved in iPrOH (4.0 mL) and cooled to 0° C., and Et$_3$N (180.0 μL, 1.29 mmol) was added thereto. The reaction mixture was stirred at 23° C. for 5 hours and distilled under reduced pressure. The residue was extracted with CH$_2$Cl$_2$. The organic layer was washed with brine, dried with Na$_2$SO$_4$, filtered and distilled under reduced pressure. The residue was purified by column chromatography (CH$_2$Cl$_2$) on silica. The fractions containing the product were collected and evaporated to obtain the white solid compound, N-(4-nitrophenethyl)-2-(trifluoromethyl)quinazolin-4-amine (50.0 mg, 32%).

$^1$H NMR (300 MHz, DMSO-d$_6$) δ=8.96 (br s, 1H), 8.34-8.26 (m, 1H), 8.19-8.10 (m, 2H), 7.93-7.80 (m, 2H), 7.68 (ddd, J=1.3, 6.8, 8.3 Hz, 1H), 7.54 (d, J=8.4 Hz, 2H), 3.85 (t, J=6.7 Hz, 2H), 3.14 (t, J=6.9 Hz, 2H)

LC/MS ESI (+): 363 (M+1)

Example 49: Synthesis of N-(4-nitrophenethyl)-2-(trifluoromethyl)quinolin-4-amine

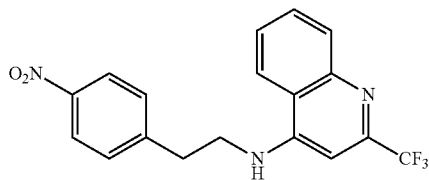 [SMILES: O=[N+]([O-])c1ccc(CCNc2cc(C(F)(F)F)nc3ccccc23)cc1]

4-Chloro-2-(trifluoromethyl)quinoline (100.0 mg, 0.43 mmol), 2-(4-nitrophenyl)ethan-1-amine hydrochloride (87.0 mg, 0.43 mmol) and Et$_3$N (180.0 μL, 1.29 mmol) were added to NMP (1.0 mL). The reaction mixture was reacted in a microwaver (50 W, 100° C.) for 1 hour and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (CH$_2$Cl$_2$:MeOH=20:1) on silica. The fractions containing the product were collected and evaporated to obtain the white solid compound, N-(4-nitrophenethyl)-2-(trifluoromethyl)quinolin-4-amine (35.0 mg, 23%).

$^1$H NMR (300 MHz, DMSO-d$_6$) δ=8.28 (d, J=8.4 Hz, 1H), 8.15 (d, J=8.4 Hz, 2H), 7.89 (d, J=8.4 Hz, 1H), 7.84-7.69 (m, 2H), 7.64-7.52 (m, 3H), 6.79-6.69 (m, 1H), 3.76-3.65 (m, 2H), 3.15 (t, J=6.9 Hz, 2H)

LC/MS ESI (+): 362 (M+1)

Example 50: Synthesis of 2-fluoro-N-(4-nitrophenethyl)-9H-purin-6-amine

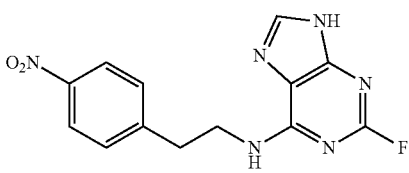 [SMILES: O=[N+]([O-])c1ccc(CCNc2nc(F)nc3[nH]cnc23)cc1]

6-Chloro-2-fluoro-9H-purine (100.0 mg, 0.58 mmol) and 2-(4-nitrophenyl)ethan-1-amine hydrochloride (117.0 mg, 0.58 mmol) were dissolved in iPrOH (4.0 mL), and Et$_3$N (240.0 μL, 1.74 mmol) was added thereto at room temperature. The reaction mixture was stirred at 60° C. for 15 hours and distilled under reduced pressure. The residue was extracted with CH$_2$Cl$_2$. The organic layer was washed with brine, dried with Na$_2$SO$_4$, filtered and distilled under reduced pressure. The residue was purified by column chromatography (CH$_2$Cl$_2$) on silica. The fractions containing the product were collected and evaporated to obtain the white solid compound, 2-fluoro-N-(4-nitrophenethyl)-9H-purin-6-amine (10.0 mg, 6%).

$^1$H NMR (300 MHz, DMSO-d$_6$) δ=13.30-12.60 (m, 1H), 8.32 (br s, 1H), 8.22-8.03 (m, 3H), 7.53 (s, 2H), 3.71 (d, J=6.5 Hz, 2H), 3.07 (t, J=7.1 Hz, 2H)

LC/MS ESI (+): 303 (M+1)

Example 51: Synthesis of N$^2$-methyl-N$^4$-(4-nitrophenethyl)quinolin-2,4-diamine 2,2,2-trifluoroacetate

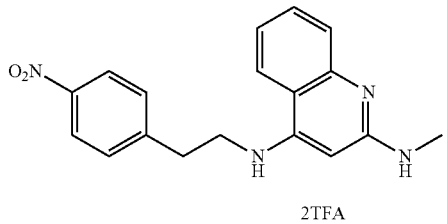 [SMILES: CNc1cc(NCCc2ccc([N+](=O)[O-])cc2)c2ccccc2n1]

2-Chloro-N-(4-nitrophenethyl)quinolin-4-amine (11.0 mg, 0.03 mmol) and 2M methylamine (0.3 ml, 0.6 mmol) were added to anhydrous 1,4-dioxane (1.0 mL). The reaction mixture was reacted in a microwaver (100 W, 180° C.) for 2 hours and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (CH$_2$Cl$_2$:MeOH=20:1) on silica. The fractions containing the product were collected and evaporated to obtain the white solid compound, N$^2$-methyl-N$^4$-(4-nitrophenethyl)quinolin-2,4-diamine 2,2,2-trifluoroacetate (10.8 mg, 74%).

$^1$H NMR (300 MHz, DMSO-d$_6$) δ=11.74 (s, 1H), 8.20-8.11 (m, 3H), 7.70-7.58 (m, 4H), 7.42-7.31 (m, 1H), 6.55 (s, 1H), 5.83 (s, 1H), 3.64-3.58 (m, 2H), 3.12 (t, J=6.6 Hz, 2H), 3.00 (s, 3H)

LC/MS ESI (+): 323 (M+1)

Example 52: Synthesis of N-(4-(2-((2-(trifluoromethyl)quinolin-4-yl)amino)ethyl)phenyl)methanesulfonamide

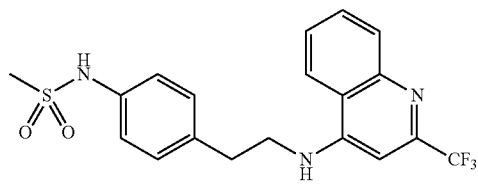 [SMILES: CS(=O)(=O)Nc1ccc(CCNc2cc(C(F)(F)F)nc3ccccc23)cc1]

(a) Synthesis of N-(4-aminophenethyl)-2-(trifluoromethyl)quinolin-4-amine

N-(4-nitrophenethyl)-2-(trifluoromethyl)quinolin-4-amine (34.0 mg, 0.09 mmol) was dissolved in MeOH (1.5 mL), and Raney Ni (34 mg, 100 w/w %) was added thereto. The reaction mixture was charged with H$_2$ gas and stirred at room temperature for 4 hours. The reaction mixture was filtered with celite and distilled under reduced pressure. The residue was purified by column chromatography (MeOH:CH$_2$Cl$_2$=1:30) on amine silica. The fractions containing the product were collected and evaporated to obtain the white solid compound, N-(4-aminophenethyl)-2-(trifluoromethyl)quinolin-4-amine (30.0 mg, 97%).

LC/MS ESI (+): 332 (M+1)

(b) Synthesis of N-(4-(2-((2-(trifluoromethyl)quinolin-4-yl)amino)ethyl)phenyl)methanesulfonamide N-(4-aminophenethyl)-2-(trifluoromethyl)quinolin-4-amine (30.0 mg, 0.09 mmol) was dissolved in pyridine (4.0 mL), and MsCl (14.0 µL, 0.18 mmol) was slowly added thereto at 21° C. After 3 hours, the reaction was terminated, and the reaction mixture was extracted with CH$_2$Cl$_2$. The organic layer was washed with brine, dried with Na$_2$SO$_4$, filtered and distilled under reduced pressure. The residue was purified by column chromatography (n-Hex:EtOAc=2:1) on silica. The fractions containing the product were collected and evaporated to obtain the white solid compound, N-(4-(2-((2-(trifluoromethyl)quinolin-4-yl)amino)ethyl)phenyl)methanesulfonamide (30.0 mg, 81%).

$^1$H NMR (300 MHz, DMSO-d$_6$) δ=9.63 (s, 1H), 8.25 (d, J=8.3 Hz, 1H), 7.89 (d, J=7.8 Hz, 1H), 7.81-7.71 (m, 2H), 7.57 (t, J=7.1 Hz, 1H), 7.27 (d, J=8.4 Hz, 2H), 7.13 (d, J=8.4 Hz, 2H), 6.75 (s, 1H), 3.62-3.56 (m, 2H), 2.98-2.92 (m, 5H)

LC/MS ESI (+): 410 (M+1)

Example 53: Synthesis of N-(4-(2-((2-(trifluoromethyl)quinazolin-4-yl)amino)ethyl)phenyl)methanesulfonamide

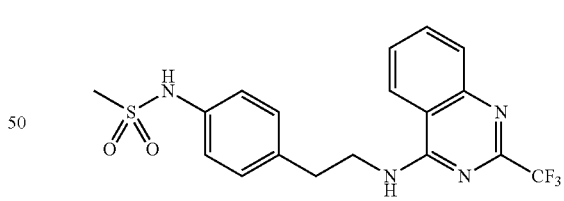

With N-(4-nitrophenethyl)-2-(trifluoromethyl)quinazolin-4-amine (60.0 mg, 0.16 mmol) as a starting material, the same synthesis procedures as Example 52 were carried out to obtain the white solid compound, N-(4-(2-((2-(trifluoromethyl)quinazolin-4-yl)amino)ethyl)phenyl)methanesulfonamide (50.0 mg, 68%: 2 steps).

$^1$H NMR (300 MHz, DMSO-d$_6$) δ=9.62 (s, 1H), 8.94 (s, 1H), 8.32 (d, J=8.2 Hz, 1H), 7.91-7.82 (m, 2H), 7.67 (t, J=8.1 Hz, 1H), 7.23 (d, J=8.4 Hz, 2H), 7.12 (d, J=8.4 Hz, 2H), 3.79-3.72 (m, 2H), 2.97-2.92 (m, 5H)

LC/MS ESI (+): 411 (M+1)

Example 54: Synthesis of 6-(2,4-dichlorophenyl)-N-(4-nitrophenethyl)quinazolin-4-amine

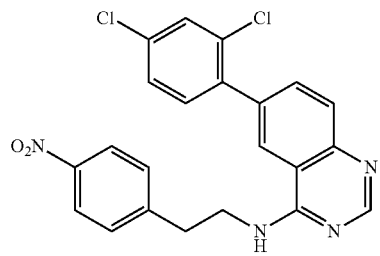 [SMILES: O=[N+]([O-])c1ccc(CCNc2ncnc3ccc(-c4ccc(Cl)cc4Cl)cc23)cc1]

(a) Synthesis of 6-bromo-N-(4-nitrophenethyl)quinazolin-4-amine

6-Bromo-4-chloroquinazoline (200.0 mg, 0.82 mmol) and 2-(4-nitrophenethyl)ethan-1-amine hydrochloride (182.0 mg, 0.90 mmol) were dissolved in iPrOH (4.0 mL), and Et$_3$N (170.0 μL, 1.23 mmol) was added thereto at room temperature. The reaction mixture was stirred at 20° C. for 15 hours and distilled under reduced pressure. The residue was extracted with CH$_2$Cl$_2$. The organic layer was washed with brine, dried with Na$_2$SO$_4$, filtered and distilled under reduced pressure. After addition of CH$_2$Cl$_2$ and water, the residue was stirred. The obtained solid was filtered and dried to obtain the ivory solid compound, 6-bromo-N-(4-nitrophenethyl)quinazolin-4-amine (210.0 mg, 69%).

LC/MS ESI (+): 373 (M+1)

(b) Synthesis of 6-(2,4-dichlorophenyl)-N-(4-nitrophenethyl)quinazolin-4-amine (2,4-Dichlorophenyl)boronic acid (31.0 mg, 0.16 mmol) and 6-bromo-N-(4-nitrophenethyl)quinazolin-4-amine (50.0 mg, 0.13 mmol) were dissolved in a mixed solvent of DME/H$_2$O (0.92 mL, 4/1 v/v), and Pd(PPh$_3$)$_4$ (31.0 mg, 0.03 mmol) and Na$_2$CO$_3$ (43.0 mg, 0.40 mmol) were added thereto. The reaction mixture was stirred at 80° C. for 3 hours, cooled to room temperature and extracted with EtOAc. The organic layer was washed with brine, dried with Na$_2$SO$_4$, filtered and distilled under reduced pressure. The residue was purified by column chromatography (n-Hex:EtOAc=1:1) on silica. The fractions containing the product were collected and evaporated to obtain the yellow solid compound, 6-(2,4-dichlorophenyl)-N-(4-nitrophenethyl)quinazolin-4-amine (15.0 mg, 26%).

$^1$H NMR (300 MHz, CDCl$_3$) δ=8.74 (s, 1H), 8.23-8.13 (m, 2H), 7.98-7.88 (m, 1H), 7.84-7.75 (m, 1H), 7.61 (d, J=1.5 Hz, 1H), 7.54 (d, J=1.9 Hz, 1H), 7.43 (d, J=8.4 Hz, 2H), 7.38-7.28 (m, 2H), 5.88-5.74 (m, 1H), 3.99 (d, J=6.5 Hz, 2H), 3.19 (t, J=7.1 Hz, 2H)

LC/MS ESI (+): 439 (M+1)

Example 55: Synthesis of 2-chloro-6-(2,4-dichlorophenyl)-N-(4-nitrophenethyl)quinolin-4-amine

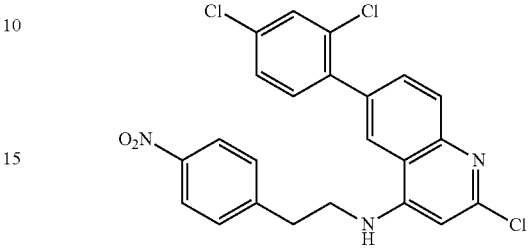

(a) Synthesis of 2,4-dichloro-6-(2,4-dichlorophenyl)quinoline

2',4'-Dichloro-[1,1'-biphenyl]-4-amine (1.5 g, 6.3 mmol) and malonic acid (1.0 g, 9.4 mmol) were dissolved in phosphorous oxychloride (15.0 mL). The reaction mixture was stirred at 100° C. for 5 hours and cooled to room temperature. After addition of ice water, the reaction mixture was neutralized by saturated NaHCO$_3$ solution. At this time, the white solid was formed and filtered. The residue was purified by column chromatography (n-Hex:CH$_2$Cl$_2$=1:4) on silica. The fractions containing the product were collected and evaporated to obtain the white solid compound, 2,4-dichloro-6-(2,4-dichlorophenyl)quinoline (483.0 mg, 22%).

LC/MS ESI (+): 342 (M+1)

(b) Synthesis of 2-chloro-6-(2,4-dichlorophenyl)-N-(4-nitrophenethyl)quinolin-4-amine 2,4-Dichloro-6-(2,4-dichlorophenyl)quinoline (300.0 mg, 0.87 mmol), 2-(4-nitrophenyl)ethan-1-amine hydrochloride (177.0 mg, 0.87 mmol) and Et$_3$N (364.0 μL, 2.61 mmol) were added to NMP (3.0 mL). The reaction mixture was reacted in a microwaver (50 W, 100° C.) for 1 hour and cooled to room temperature. After addition of ice water, the reaction mixture was extracted with CH$_2$Cl$_2$. The organic layer was washed with brine, dried with Na$_2$SO$_4$ and filtered. The residue obtained under reduced pressure was purified by column chromatography (n-Hex:EtOAc=1:1) on silica. The fractions containing the product were collected and evaporated to obtain the white solid compound, 2-chloro-6-(2,4-dichlorophenyl)-N-(4-nitrophenethyl)quinolin-4-amine (1.2 mg, 0.3%).

$^1$H NMR (300 MHz, CDCl$_3$) δ=8.74 (s, 1H), 8.22-8.13 (m, 2H), 7.96-7.89 (m, 1H), 7.83-7.75 (m, 1H), 7.61 (d, J=1.5 Hz, 1H), 7.54 (d, J=1.9 Hz, 1H), 7.43 (d, J=8.4 Hz, 2H), 7.38-7.29 (m, 2H), 5.86-5.74 (m, 1H), 3.99 (q, J=6.9 Hz, 2H), 3.19 (t, J=7.1 Hz, 2H)

LC/MS ESI (+): 472 (M+1)

Example 56: Synthesis of N-(4-(2-((6-(2,4-dichlorophenyl)quinazolin-4-yl)amino)ethyl)phenyl)methanesulfonamide

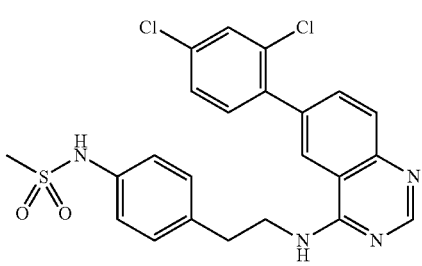 [SMILES: CS(=O)(=O)Nc1ccc(CCNc2ncnc3ccc(-c4ccc(Cl)cc4Cl)cc23)cc1]

With 6-(2,4-dichlorophenyl)-N-(4-nitrophenethyl)quinazolin-4-amine (35.0 mg, 0.08 mmol) as a starting material, the same synthesis procedures as Example 52 were carried out to obtain the white solid compound, N-(4-(2-((6-(2,4-dichlorophenyl)quinazolin-4-yl)amino)ethyl)phenyl)methanesulfonamide (10.0 mg, 23%: 2 steps).

$^1$H NMR (300 MHz, CDCl$_3$) δ=8.72 (s, 1H), 7.95-7.87 (m, 1H), 7.82-7.75 (m, 1H), 0.64-7.58 (m, 1H), 7.56-7.52 (m, 1H), 7.40-7.31 (m, 2H), 7.30-7.24 (m, 2H), 7.22-7.12 (m, 2H), 6.34-6.27 (m, 1H), 5.79-5.70 (m, 1H), 3.98-3.88 (m, 2H), 3.08-2.94 (m, 5H)

LC/MS ESI (+): 487 (M+1)

Example 57: Synthesis of N-(4-(2-((2-chloro-6-(2,4-dichlorophenyl)quinolin-4-yl)amino)ethyl)phenyl)methanesulfonamide

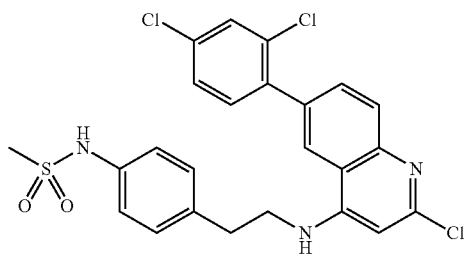 [SMILES: CS(=O)(=O)Nc1ccc(CCNc2cc(Cl)nc3ccc(-c4ccc(Cl)cc4Cl)cc23)cc1]

With 2-chloro-6-(2,4-dichlorophenyl)-N-(4-nitrophenethyl)quinolin-4-amine (200.0 mg, 0.42 mmol) as a starting material, the same synthesis procedures as Example 52 were carried out to obtain the white solid compound, N-(4-(2-((2-chloro-6-(2,4-dichlorophenyl)quinolin-4-yl)amino) ethyl)phenyl)methanesulfonamide (45.0 mg, 20%: 2 steps).

$^1$H NMR (300 MHz, CDCl$_3$) δ=7.99-7.88 (m, 1H), 7.68 (dd, J=1.7, 8.6 Hz, 1H), 7.55 (dd, J=1.9, 9.5 Hz, 2H), 7.41-7.15 (m, 6H), 6.52-6.46 (m, 1H), 6.41 (s, 1H), 5.18-5.09 (m, 1H), 3.66-3.53 (m, 2H), 3.10-2.97 (m, 5H)

LC/MS ESI (+): 520 (M+1)

Example 58: Synthesis of 2-chloro-N-(4-(methylsulfonamido)benzyl)quinolin-4-carboxamide

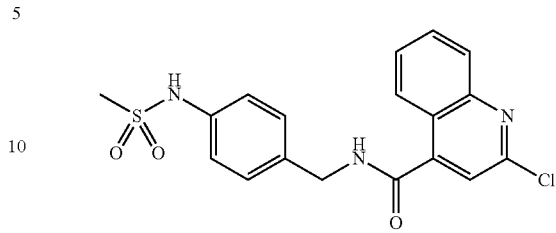

With 2-chloro-N-(4-nitrobenzyl)quinolin-4-carboxamide (90.0 mg, 0.26 mmol) as a starting material, the same synthesis procedures as Example 52 were carried out to obtain the white solid compound, 2-chloro-N-(4-(methylsulfonamido)benzyl)quinolin-4-carboxamide (10.0 mg, 34%: 2 steps).

$^1$H NMR (300 MHz, DMSO-d$_6$) δ=9.72 (s, 1H), 9.40 (s, 1H), 8.12 (d, J=8.0 Hz, 1H), 8.02 (d, J=8.4 Hz, 1H), 7.93-7.83 (m, 1H), 7.77-7.67 (m, 2H), 7.37 (d, J=8.4 Hz, 2H), 7.21 (d, J=8.4 Hz, 2H), 4.51 (d, J=5.7 Hz, 2H), 2.97 (s, 3H)

LC/MS ESI (+): 390 (M+1)

Example 59: Synthesis of N-(2,2-difluoro-2-(4-nitrophenyl)ethyl)quinazolin-4-amine

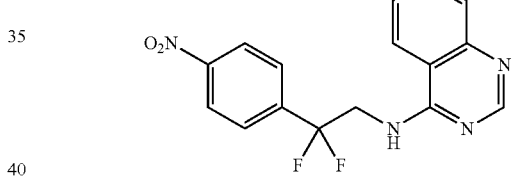

(a) Synthesis of 1-(2-azido-1,1-difluoroethyl)-4-nitrobenzene

2-Azido-1-(4-nitrophenyl)ethan-1-one (2.59 g, 12.6 mmol) was dissolved in CH$_2$Cl$_2$ (50.0 mL), and DAST (3.29 mL, 25.1 mmol) was slowly added thereto at −20° C. The reaction mixture was stirred at −20° C. for 5 days. After addition of saturated NaHCO$_3$ aqueous solution to terminate the reaction, the reaction mixture was extracted with CH$_2$Cl$_2$. The organic layer was washed with brine, dried with Na$_2$SO$_4$, filtered and distilled under reduced pressure. The residue was purified by column chromatography (n-Hex:CH$_2$Cl$_2$=2:1) on silica. The fractions containing the product were collected and evaporated to obtain the yellow oil compound 1-(2-azido-1,1-difluoroethyl)-4-nitrobenzene (1.60 g, 56%).

$^1$H NMR (300 MHz, CDCl$_3$) δ=8.33 (d, J=8.3 Hz, 2H), 7.72 (d, J=8.3 Hz, 2H), 3.77 (t, J=12.8 Hz, 2H)

(b) Synthesis of 2,2-difluoro-2-(4-nitrophenyl)ethan-1-amine 1-(2-Azido-1,1-difluoroethyl)-4-nitrobenzene (1.60 g, 7.0 mmol) was dissolved in THF (40.0 mL), and PPh$_3$ (2.58 g, 9.8 mmol) and H$_2$O (20 ml) were slowly added thereto at 25° C. The reaction mixture was stirred at 50° C. for 3 days. After addition of 1N HCl aqueous solution to terminate the reaction, the reaction mixture was extracted with EtOAc. The organic layer was washed with brine, dried with $Na_2SO_4$, filtered and distilled under reduced pressure. The residue was purified by column chromatography (MeOH:$CH_2Cl_2$=1:40) on silica. The fractions containing the product were collected and evaporated to obtain the orange solid compound, 2,2-difluoro-2-(4-nitrophenyl)ethan-1-amine (933.0 mg, 66%).

LC/MS ESI (+): 203 (M+1)

(c) Synthesis of N-(2,2-difluoro-2-(4-nitrophenyl)ethyl)quinazolin-4-amine

With 2,2-difluoro-2-(4-nitrophenyl)ethan-1-amine (61.0 mg, 0.30 mmol) and 4-chloroquinazoline (50.0 mg, 0.30 mmol) as starting materials, the same synthesis procedures as Example 5 were carried out to obtain the white solid compound, N-(2,2-difluoro-2-(4-nitrophenyl)ethyl)quinazolin-4-amine (3.1 mg, 3%).

$^1$H NMR (300 MHz, $CDCl_3$) δ=8.59 (s, 1H), 8.27 (d, J=8.8 Hz, 2H), 7.92-7.71 (m, 5H), 7.58-7.49 (m, 1H), 5.99 (t, J=5.5 Hz, 1H), 4.60-4.43 (m, 2H)

LC/MS ESI (+): 331 (M+1)

Example 60: Synthesis of 1,1,1-trifluoro-N-(4-(2-(quinazolin-4-ylamino)ethyl)phenyl)methanesulfonamide

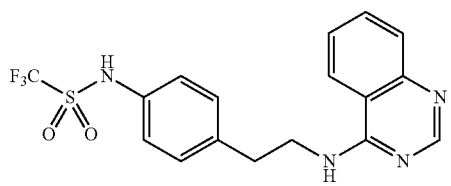 [SMILES: O=S(=O)(Nc1ccc(CCNc2ncnc3ccccc23)cc1)C(F)(F)F]

(a) Synthesis of N-(4-aminophenethyl)quinazolin-4-amine

N-(4-nitrophenethyl)quinazolin-4-amine (118.0 mg, 0.40 mmol) was dissolved in MeOH (4.0 mL), and Raney Ni (59 mg, 50 w/w %) was added thereto. The reaction mixture was charged with $H_2$ gas and stirred at room temperature for 3 hours. The reaction mixture was filtered with celite and distilled under reduced pressure. The residue was purified by column chromatography (MeOH:$CH_2Cl_2$=1:20) on silica. The fractions containing the product were collected and evaporated to obtain the white solid compound, N-(4-aminophenethyl)quinazolin-4-amine (30.0 mg, 28%).

LC/MS ESI (+): 265 (M+1)

(b) Synthesis of 1,1,1-trifluoro-N-(4-(2-(quinazolin-4-ylamino)ethyl)phenyl)methanesulfonamide N-(4-aminophenethyl)quinazolin-4-amine (30.0 mg, 0.11 mmol) was dissolved in $CH_2Cl_2$ (2.3 mL), and anhydrous trifluoromethanesulfonic acid (27.9 μL, 0.17 mmol) was slowly added thereto at 0° C. The reaction mixture was stirred at room temperature for 1 hour and extracted with $CH_2Cl_2$. The organic layer was washed with brine, dried with $Na_2SO_4$, filtered and distilled under reduced pressure. The residue was purified by column chromatography ($CH_3CN$:$H_2O$=30:70) on reverse-phase silica. The fractions containing the product were collected and evaporated to obtain the white solid compound, 1,1,1-trifluoro-N-(4-(2-(quinazolin-4-ylamino)ethyl)phenyl)methanesulfonamide (29.2 mg, 65%).

$^1$H NMR (300 MHz, DMSO-$d_6$) δ=10.09-9.89 (m, 1H), 8.87 (s, 1H), 8.44-8.32 (m, 1H), 8.07-7.96 (m, 1H), 7.81-7.71 (m, 2H), 7.33-7.23 (m, 2H), 7.15 (d, J=8.4 Hz, 2H), 3.98-3.86 (m, 2H), 3.06-2.94 (m, 3H)

LC/MS ESI (+): 397 (M+1)

Example 61: Synthesis of 6-fluoro-N-(4-nitrophenethyl)quinazolin-4-amine

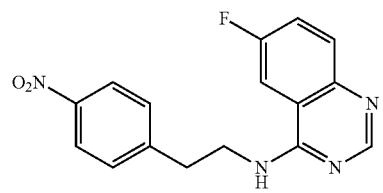 [SMILES: O=[N+]([O-])c1ccc(CCNc2ncnc3ccc(F)cc23)cc1]

4-Chloro-6-fluoroquinazoline (200.0 mg, 1.10 mmol) and 2-(4-nitrophenyl)ethan-1-amine hydrochloride (222.0 mg, 1.10 mmol) were dissolved in iPrOH (5.5 mL) and cooled to 0° C., and $Et_3N$ (457.0 μL, 3.30 mmol) was added thereto. The reaction mixture was stirred at 100° C. for 15 hours and distilled under reduced pressure. The residue was extracted with EtOAc. The organic layer was washed with brine, dried with $Na_2SO_4$, filtered and distilled under reduced pressure. The residue was purified by column chromatography ($CH_2Cl_2$:MeOH=30:1) on silica. The fractions containing the product were collected and evaporated to obtain the white solid compound, 6-fluoro-N-(4-nitrophenethyl)quinazolin-4-amine (270.0 mg, 78%).

$^1$H NMR (300 MHz, DMSO-$d_6$) δ=8.48 (s, 1H), 8.39-8.30 (m, 1H), 8.16 (d, J=8.4 Hz, 2H), 8.09-8.00 (m, 1H), 7.80-7.62 (m, 2H), 7.55 (d, J=8.4 Hz, 2H), 3.82 (q, J=6.9 Hz, 2H), 3.19-3.06 (m, 2H)

LC/MS ESI (+): 313 (M+1)

Example 62: Synthesis of N-(4-nitrophenethyl)isoquinolin-4-amine

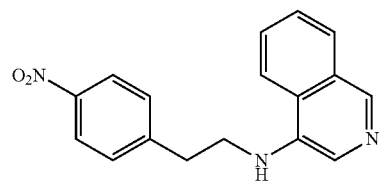 [SMILES: O=[N+]([O-])c1ccc(CCNc2cncc3ccccc23)cc1]

4-(4,4,5,5-Tetramethyl-1,3,2-dioxaborolan-2-yl)isoquinoline (30.0 mg, 0.12 mmol) and 2-(4-nitrophenyl)ethan-1-amine hydrochloride (48.0 mg, 0.24 mmol) were dissolved in MeOH (2.0 mL), and $Et_3N$ (33.0 μL, 0.24 mmol) was added thereto at room temperature. The reaction mixture was stirred at 20° C. for 30 minutes, and copper(I) oxide (42.0 mg, 0.12 mmol) was added thereto. The reaction mixture was stirred at 20° C. for 5 hours and distilled under reduced pressure. The residue was extracted with $CH_2Cl_2$. The organic layer was washed with brine, dried with Na₂SO₄, filtered and distilled under reduced pressure. The residue was purified by column chromatography (n-Hex: EtOAc=1:2) on amine silica. The fractions containing the product were collected and evaporated to obtain the yellow solid compound, N-(4-nitrophenethyl)isoquinolin-4-amine (10.0 mg, 28%).

¹H NMR (300 MHz, CDCl₃) δ=8.80-8.69 (m, 1H), 8.21 (d, J=8.4 Hz, 2H), 8.04-7.90 (m, 2H), 7.73-7.57 (m, 3H), 7.44 (d, J=8.4 Hz, 2H), 4.22 (br s, 1H), 3.70 (q, J=6.5 Hz, 2H), 3.31-3.14 (m, 2H)

LC/MS ESI (+): 294 (M+1)

Example 63: Synthesis of N-(4-(2-(isoquinolin-4-ylamino)ethyl)phenyl)methanesulfonamide

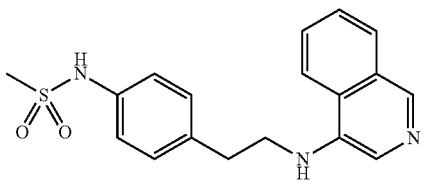 [SMILES: CS(=O)(=O)Nc1ccc(CCNc2cncc3ccccc23)cc1]

With N-(4-nitrophenethyl)isoquinolin-4-amine (20.0 mg, 0.07 mmol) as a starting material, the same synthesis procedures as Example 52 were carried out to obtain the ivory solid compound, N-(4-(2-(isoquinolin-4-ylamino)ethyl)phenyl)methanesulfonamide (5.0 mg, 21%: 2 steps).

¹H NMR (300 MHz, CDCl₃) δ=8.76-8.69 (m, 1H), 7.96-7.89 (m, 2H), 7.71-7.56 (m, 3H), 7.33-7.19 (m, 5H), 4.32-4.22 (m, 1H), 3.66-3.56 (m, 2H), 3.13-3.00 (m, 5H)

LC/MS ESI (+): 342 (M+1)

Example 64: Synthesis of N-(4-(2-((6-fluoroquinazolin-4-yl)amino)ethyl)phenyl)methanesulfonamide

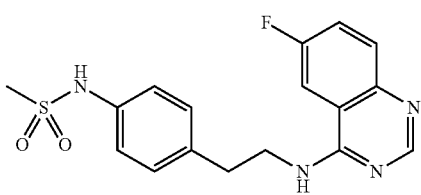

With 6-fluoro-N-(4-nitrophenethyl)quinazolin-4-amine (60.0 mg, 0.19 mmol) as a starting material, the same synthesis procedures as Example 52 were carried out to obtain the white solid compound, N-(4-(2-((6-fluoroquinazolin-4-yl)amino)ethyl)phenyl)methanesulfonamide (63.0 mg, 94%: 2 steps).

¹H NMR (300 MHz, DMSO-d₆)=9.62 (s, 1H), 8.53-8.44 (m, 1H), 8.33 (t, J=5.3 Hz, 1H), 8.12-8.00 (m, 1H), 7.81-7.61 (m, 2H), 7.28-7.18 (m, 2H), 7.18-7.08 (m, 2H), 3.80-3.65 (m, 2H), 2.93 (s, 5H)

LC/MS ESI (+): 361 (M+1)

Example 65: Synthesis of 2-(4-nitrophenyl)-N-(quinazolin-4-yl)acetamide

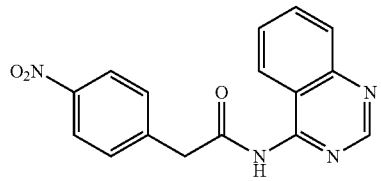 [SMILES: O=C(Cc1ccc([N+](=O)[O-])cc1)Nc1ncnc2ccccc12]

Quinazolin-4-amine (30.0 mg, 0.21 mmol) and 2-(4-nitrophenyl)acetyl chloride (41.0 mg, 0.21 mmol) were dissolved in toluene (2.1 mL) and stirred under reflux at 100° C. for 2 hours. The reaction mixture was cooled to room temperature and distilled under reduced pressure. The residue was extracted with EtOAc. The organic layer was washed with brine, dried with Na₂SO₄ and distilled under reduced pressure. The residue was purified by column chromatography (n-Hex:EtOAc=1:1) on silica. The fractions containing the product were collected and evaporated to obtain the white solid compound, 2-(4-nitrophenyl)-N-(quinazolin-4-yl)acetamide (3.0 mg, 5%).

¹H NMR (300 MHz, DMSO-d₆) δ=11.22-11.11 (m, 1H), 9.02 (s, 1H), 8.31-8.18 (m, 3H), 8.02-7.91 (m, 2H), 7.75-7.63 (m, 1H), 7.76-7.62 (m, 2H), 4.25 (s, 2H)

LC/MS ESI (+): 309 (M+1)

Example 66: Synthesis of N-(4-(2-(thieno[3,2-d]pyrimidin-4-ylamino)ethyl)phenyl)methanesulfonamide

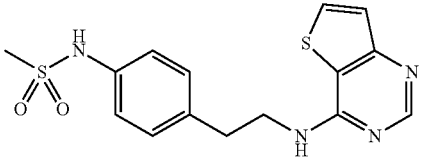 [SMILES: CS(=O)(=O)Nc1ccc(CCNc2ncnc3ccsc23)cc1]

With N-(4-nitrophenethyl)thieno[3,2-d]pyrimidin-4-amine (100.0 mg, 0.33 mmol) as a starting material, the same synthesis procedures as Example 52 were carried out to obtain the white solid compound, N-(4-(2-(thieno[3,2-d]pyrimidin-4-ylamino)ethyl)phenyl)methanesulfonamide (70.0 mg, 61%: 2 steps).

¹H NMR (300 MHz, DMSO-d₆)=9.60 (s, 1H), 8.49-8.40 (m, 1H), 8.12-8.03 (m, 1H), 7.99-7.88 (m, 1H), 7.36 (d, J=5.3 Hz, 1H), 7.25-7.17 (m, 2H), 7.16-7.07 (m, 2H), 3.75-3.62 (m, 2H), 2.99-2.84 (m, 5H)

LC/MS ESI (+): 349 (M+1)

Example 67: Synthesis of 2-chloro-N-(4-nitrophenethyl)pyrido[2,3-d]pyrimidin-4-amine

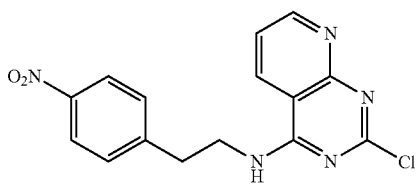

2,4-Dichloropyrido[2,3-d]pyrimidine (170.0 mg, 0.85 mmol) and 2-(4-nitrophenyl)ethan-1-amine hydrochloride (172.0 mg, 0.85 mmol) were dissolved in iPrOH (8.5 mL), and Et₃N (250.0 μL, 1.80 mmol) was added thereto at room temperature. The reaction mixture was stirred at 21° C. for 5 hours and distilled under reduced pressure. After addition of CH₂Cl₂ and water, the residue was stirred. The obtained solid was filtered and dried to obtain the white solid compound, 2-chloro-N-(4-nitrophenethyl)pyrido[2,3-d]pyrimidin-4-amine (250.0 mg, 89%).

¹H NMR (300 MHz, DMSO-d₆) δ=9.15 (t, J=5.3 Hz, 1H), 8.97 (d, J=2.7 Hz, 1H), 8.71-8.61 (m, 1H), 8.20-8.12 (m, 2H), 7.62-7.52 (m, 3H), 3.86-3.74 (m, 2H), 3.17-3.06 (m, 2H)

LC/MS ESI (+): 330 (M+1)

Example 68: Synthesis of N-(4-(2-(thieno[2,3-d]pyrimidin-4-ylamino)ethyl)phenyl)methanesulfonamide

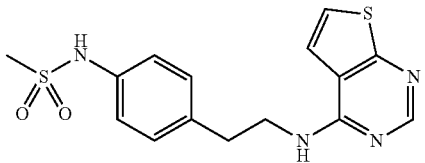 [SMILES: CS(=O)(=O)Nc1ccc(CCNc2ncnc3sccc23)cc1]

With N-(4-nitrophenethyl)thieno[2,3-d]pyrimidin-4-amine (110.0 mg, 0.41 mmol) as a starting material, the same synthesis procedures as Example 52 were carried out to obtain the white solid compound, N-(4-(2-(thieno[2,3-d]pyrimidin-4-ylamino)ethyl)phenyl)methanesulfonamide (80.0 mg, 53%: 2 steps).

¹H NMR (300 MHz, DMSO-d₆) δ=9.76-9.47 (m, 1H), 8.36 (s, 1H), 8.14-8.00 (m, 1H), 7.63-7.50 (m, 2H), 7.26-7.17 (m, 2H), 7.16-7.06 (m, 2H), 3.75-3.61 (m, 2H), 3.01-2.81 (m, 5H)

LC/MS ESI (+): 349 (M+1)

Example 69: Synthesis of N-(4-(2-(thiazolo[5,4-d]pyrimidin-7-ylamino)ethyl)phenyl)methanesulfonamide

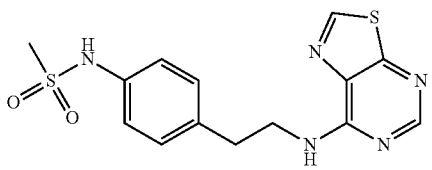 [SMILES: CS(=O)(=O)Nc1ccc(CCNc2ncnc3scnc23)cc1]

(a) Synthesis of N-(4-nitrophenethyl)thiazolo[5,4-d]pyrimidin-7-amine

7-Chlorothiazolo[5,4-d]pyrimidine (100.0 mg, 0.58 mmol), 2-(4-nitrophenyl)ethan-1-amine hydrochloride (118.0 mg, 0.58 mmol) and Et₃N (244.0 μL, 1.75 mmol) were added to i-PrOH (5.8 mL). The reaction mixture was stirred at room temperature for 22 hours. After addition of water, the reaction mixture was extracted with EtOAc, washed with brine, dried with Na₂SO₄, filtered and distilled under reduced pressure. The residue was purified by C18 reversed-phase silica gel column chromatography (CH₃CN:H₂O condition) and freeze-dried to obtain the yellow solid compound, N-(4-nitrophenethyl)thiazolo[5,4-d]pyrimidin-7-amine (124.0 mg, 71%).

¹H NMR (400 MHz, DMSO-d₆) δ=9.25 (s, 1H), 8.42 (s, 2H), 8.16 (d, J=8.7 Hz, 2H), 7.55 (d, J=8.6 Hz, 2H), 3.81 (q, J=6.8 Hz, 2H), 3.11 (t, J=7.1 Hz, 2H)

LC/MS ESI (+): 302 (M+1)

(b) Synthesis of N-(4-aminophenethyl)thiazolo[5,4-d]pyrimidin-7-amine

N-(4-nitrophenethyl)thiazolo[5,4-d]pyrimidin-7-amine (50.0 mg, 0.17 mmol) was dissolved in a mixed solvent of CH₃OH:H₂O (1.6 mL, 10/1 v/v), and Zn (108.0 mg, 1.66 mmol) and ammonium chloride (44.4 mg, 0.83 mmol) were added thereto at room temperature. The reaction mixture was stirred at room temperature for 2 hours and filtered with celite. After addition of water, the reaction mixture was extracted with EtOAc, washed with brine, dried with Na₂SO₄, filtered and distilled under reduced pressure. The residue was purified by C18 reversed-phase silica gel column chromatography (CH₃CN:H₂O condition) and freeze-dried to obtain the white solid compound, N-(4-aminophenethyl)thiazolo[5,4-d]pyrimidin-7-amine (36.5 mg, 80%).

¹H NMR (400 MHz, DMSO-d₆) δ=9.17 (s, 1H), 8.35 (s, 1H), 8.23 (br t, J=5.7 Hz, 1H), 6.86-6.80 (m, J=8.1 Hz, 2H), 6.44-6.39 (m, J=8.2 Hz, 2H), 4.82 (s, 2H), 3.61-3.51 (m, 2H), 2.71-2.61 (m, 2H)

LC/MS ESI (+): 272 (M+1)

(c) Synthesis of N-(4-(2-(thiazolo[5,4-d]pyrimidin-7-ylamino)ethyl)phenyl)methanesulfonamide N-(4-aminophenethyl)thiazolo[5,4-d]pyrimidin-7-amine (37.5 mg, 0.10 mmol) was dissolved in pyridine (1.0 mL), and MsCl (11.8 μL, 0.15 mmol) was slowly added thereto at 0° C. The reaction mixture was stirred at room temperature for 2 hours. After addition of water, the reaction mixture was extracted with EtOAc, washed with brine, dried with Na₂SO₄, filtered and distilled under reduced pressure. The residue was purified by C18 reversed-phase silica gel column chromatography (CH₃CN:H₂O condition) and freeze-dried to obtain the white solid compound, N-(4-(2-(thiazolo[5,4-d]pyrimidin-7-ylamino)ethyl)phenyl)methanesulfonamide (19.4 mg, 55%).

¹H NMR (400 MHz, DMSO-d₆) δ=9.61 (s, 1H), 9.24 (s, 1H), 8.42 (s, 1H), 8.34 (brs, 1H), 7.24-7.19 (m, J=8.3 Hz, 2H), 7.15-7.10 (m, J=8.3 Hz, 2H), 3.71 (q, J=6.9 Hz, 2H), 2.93 (s, 3H), 2.90 (br t, J=7.4 Hz, 2H)

LC/MS ESI (+): 350 (M+1)

Example 70: Synthesis of N-(4-(2-((7H-pyrrolo[2,3-d]pyrimidin-4-yl)amino)ethyl)phenyl)methanesulfonamide

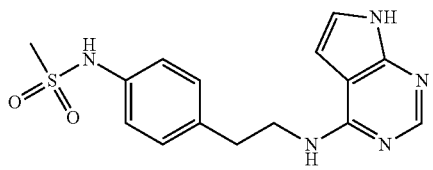 [SMILES: CS(=O)(=O)Nc1ccc(CCNc2ncnc3[nH]ccc23)cc1]

(a) Synthesis of N-(4-nitrophenethyl)-7H-pyrrolo[2,3-d]pyrimidin-4-amine

4-Chloro-7H-pyrrolo[2,3-d]pyrimidine (100.0 mg, 0.65 mmol), 2-(4-nitrophenyl)ethan-1-amine hydrochloride (132.0 mg, 0.65 mmol) and Et₃N (272.0 μL, 1.95 mmol) were added to i-PrOH (6.5 mL). The reaction mixture was stirred at 80° C. for 2 days. After addition of water, the reaction mixture was extracted with EtOAc, washed with brine, dried with Na₂SO₄, filtered and distilled under reduced pressure. The residue was purified by C18 reversed-phase silica gel column chromatography (CH₃CN:H₂O condition) and freeze-dried to obtain the yellow solid compound, N-(4-nitrophenethyl)-7H-pyrrolo[2,3-d]pyrimidin-4-amine (102.0 mg, 55%).

LC/MS ESI (+): 284 (M+1)

(b) Synthesis of N-(4-(2-((7H-pyrrolo[2,3-d]pyrimidin-4-yl)amino)ethyl)phenyl)methanesulfonamide N-(4-nitrophenethyl)-7H-pyrrolo[2,3-d]pyrimidin-4-amine (21.3 mg, 0.07 mmol) was dissolved in acetic acid (1.5 mL), and Zn (24.0 mg, 0.37 mmol) was added thereto at room temperature. The reaction mixture was stirred at room temperature for 1 hour and filtered with celite. After addition of water, the reaction mixture was extracted with EtOAc, washed with brine, dried with Na₂SO₄, filtered and distilled under reduced pressure. The residue was dissolved in pyridine (1.5 mL), and MsCl (7.03 μL, 0.57 mmol) was slowly added thereto at 0° C. The reaction mixture was stirred at room temperature for 1 hour and filtered with celite. After addition of water, the reaction mixture was extracted with EtOAc, washed with brine, dried with Na₂SO₄, filtered and distilled under reduced pressure. The residue was purified by C18 reversed-phase silica gel column chromatography (CH₃CN:H₂O condition) and freeze-dried to obtain the white solid compound, N-(4-(2-((7H-pyrrolo[2,3-d]pyrimidin-4-yl)amino)ethyl)phenyl)methanesulfonamide (5.0 mg, 20%).

1H NMR (400 MHz, DMSO-d6) δ=11.40 (br s, 1H), 9.54 (br s, 1H), 8.04 (s, 1H), 7.41 (br s, 1H), 7.18-7.12 (m, J=8.3 Hz, 2H), 7.10-7.04 (m, J=8.2 Hz, 2H), 6.98 (br s, 1H), 6.45 (br s, 1H), 3.62-3.54 (m, 2H), 2.87 (s, 3H), 2.80 (br t, J=7.5 Hz, 2H)

LC/MS ESI (+): 332 (M+1)

Example 71: Synthesis of N-(4-(2-(pyrido[3,4-b]pyrazin-5-ylamino)ethyl)phenyl)methanesulfonamide

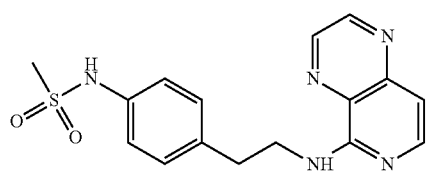 [SMILES: CS(=O)(=O)Nc1ccc(CCNc2nccc3nccnc23)cc1]

(a) Synthesis of N-(4-nitrophenethyl)pyrido[3,4-b]pyrazin-5-amine

5-Chloropyrido[3,4-b]pyrazine (100.0 mg, 0.64 mmol), 2-(4-nitrophenyl)ethan-1-amine hydrochloride (122.0 mg, 0.64 mmol) and DIPEA (527.0 μL, 3.02 mmol) were dissolved in sulforane (3.0 mL), and stirred at 160° C. for 18 hours. After addition of H₂O, the reaction mixture was stirred and extracted with EtOAc. The organic layer was washed with brine, dried with Na₂SO₄, filtered and concentrated under reduced pressure. The residue was purified by C18 reversed-phase silica gel column chromatography (CH₃CN containing 0.1% formic acid:H₂O containing 0.1% formic acid) to obtain the yellow solid, N-(4-nitrophenethyl)pyrido[3,4-b]pyrazin-5-amine (99.0 mg, 56%).

LC/MS ESI (+): 296 (M+1)

(b) Synthesis of N-(4-aminophenethyl)pyrido[3,4-b]pyrazin-5-amine 3N-(4-nitrophenethyl)pyrido[3,4-b]pyrazin-5-amine (99.0 mg, 0.33 mmol) was dissolved in a mixed solvent of methanol/water (6.7 mL, 10/1 v/v), and Zn (110.0 mg, 1.67 mmol) and ammonium formate (179.0 mg, 3.35 mmol) were added thereto at room temperature. The reaction mixture was stirred at 24° C. for 2 hours. After addition of H₂O the reaction mixture was extracted with CH₂Cl₂, washed with brine, dried with Na₂SO₄, filtered and distilled under reduced pressure. The residue was purified by C18 reversed-phase silica gel column chromatography (CH₃CN containing 0.1% formic acid:H₂O containing 0.1% formic acid) to obtain the yellow solid, N-(4-aminophenethyl)pyrido[3,4-b]pyrazin-5-amine (5.3 mg, 6%).

LC/MS ESI (+): 266 (M+1)

(c) Synthesis of N-(4-(2-(pyrido[3,4-b]pyrazin-5-ylamino)ethyl)phenyl)methanesulfonamide N-(4-aminophenethyl)pyrido[3,4-b]pyrazin-5-amine (5.3 mg, 0.02 mmol) was dissolved in pyridine (0.4 mL), and MsCl (1.55 μL, 0.02 mmol) was slowly added thereto at 24° C. After the reaction was terminated, the reaction mixture was extracted with CH₂Cl₂. The organic layer was washed with brine, dried with Na₂SO₄, filtered and distilled under reduced pressure. The residue was purified by C18 reversed-phase silica gel column chromatography (CH₃CN containing 0.1% formic acid:H₂O containing 0.1% formic acid) to obtain the white solid compound, N-(4-(2-(pyrido[3,4-b]pyrazin-5-ylamino)ethyl)phenyl)methanesulfonamide (5.0 mg, 72.3%).

1H NMR (400 MHz, DMSO-d6) δ=9.60 (br s, 1H), 9.00 (s, 1H), 8.78 (s, 1H), 8.15 (d, J=5.9 Hz, 1H), 7.92 (t, J=5.7 Hz, 1H), 7.26-7.20 (m, J=8.3 Hz, 2H), 7.16-7.11 (m, J=8.3 Hz, 2H), 6.97 (d, J=5.9 Hz, 1H), 3.78-3.70 (m, 2H), 2.93 (s, 3H), 2.90 (s, 2H)

LC/MS ESI (+): 344 (M+1)

Example 72: Synthesis of N-(4-(2-((3-methylquinolin-4-yl)amino)ethyl)phenyl)methanesulfonamide

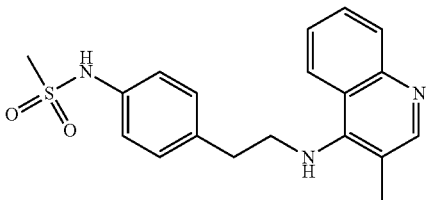 [SMILES: Cc1cnc2ccccc2c1NCCc1ccc(NS(C)(=O)=O)cc1]

(a) Synthesis of 3-methyl-N-(4-nitrophenethyl)isoquinolin-4-amine

4-Chloro-3-methylquinoline (100.0 mg, 0.56 mmol), 2-(4-nitrophenyl)ethan-1-amine hydrochloride (114.0 mg, 0.56 mmol) and DIPEA (492.0 µL, 2.81 mmol) were dissolved in sulforane (2.8 mL) and stirred at 160° C. for 18 hours. After addition of H₂O, the reaction mixture was stirred and extracted with EtOAc. The organic layer was washed with brine, dried with Na₂SO₄, filtered and concentrated under reduced pressure. The residue was purified by C18 reversed-phase silica gel column chromatography (CH₃CN containing 0.1% formic acid:H₂O containing 0.1% formic acid) to obtain the yellow solid, N-(4-nitrophenethyl)isoquinolin-1-amine (31.0 mg, 18%).

LC/MS ESI (+): 308 (M+1)

(b) Synthesis of N-(4-aminophenethyl)-3-methylquinolin-4-amine

3-Methyl-N-(4-nitrophenethyl)isoquinolin-4-amine (31.0 mg, 0.10 mmol) was dissolved in a mixed solvent of methanol/water (2.0 mL, 10/1 v/v), and Zn (33.0 mg, 0.50 mmol) and ammonium formate (54.0 mg, 1.00 mmol) were added thereto at room temperature. The reaction mixture was stirred at 24° C. for 2 hours. After addition of H₂O, the reaction mixture was extracted with CH₂Cl₂, washed with brine, dried with Na₂SO₄, filtered and distilled under reduced pressure. The residue was purified by C18 reversed-phase silica gel column chromatography (CH₃CN containing 0.1% formic acid:H₂O containing 0.1% formic acid) to obtain the yellow solid, N-(4-aminophenethyl)-3-methylquinolin-4-amine (11.0 mg, 39%).

LC/MS ESI (+): 278 (M+1)

(c) Synthesis of N-(4-(2-((3-methylquinolin-4-yl)amino)ethyl)phenyl)methanesulfonamide N-(4-aminophenethyl)-3-methylquinolin-4-amine (11.0 mg, 0.04 mmol) was dissolved in pyridine (0.79 mL), and MsCl (3.1 µL, 0.04 mmol) was slowly added thereto at 24° C. After the reaction was terminated, the reaction mixture was extracted with CH₂Cl₂. The organic layer was washed with brine, dried with Na₂SO₄, filtered and distilled under reduced pressure. The residue was purified by C18 reversed-phase silica gel column chromatography (CH₃CN containing 0.1% formic acid:H₂O containing 0.1% formic acid) to obtain the white solid compound, N-(4-(2-((3-methylquinolin-4-yl)amino)ethyl)phenyl)methanesulfonamide (7.0 mg, 50%).

1H NMR (400 MHz, DMSO-d6) δ=9.60 (br s, 1H), 8.35 (s, 1H), 8.13 (d, J=8.4 Hz, 1H), 7.79 (d, J=8.3 Hz, 1H), 7.57 (t, J=7.6 Hz, 1H), 7.41 (t, J=7.6 Hz, 1H), 7.19-7.12 (m, 2H), 7.12-7.08 (m, 2H), 5.89 (br t, J=6.1 Hz, 1H), 3.68 (q, J=6.8 Hz, 2H), 2.92 (s, 3H), 2.82 (t, J=7.4 Hz, 2H), 2.32 (s, 3H)

LC/MS ESI (+): 356 (M+1)

Example 73: Synthesis of N-(4-(2-(furo[3,2-c]pyridin-4-ylamino)ethyl)phenyl)methanesulfonamide

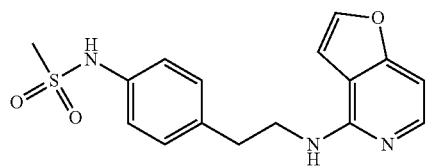 [SMILES: CS(=O)(=O)Nc1ccc(CCNc2nccc3occc23)cc1]

(a) Synthesis of N-(4-nitrophenethyl)furo[3,2-c]pyridin-4-amine

4-Chlorofuro[3,2-c]pyridine (150.0 mg, 0.98 mmol), 2-(4-nitrophenyl)ethan-1-amine hydrochloride (297.0 mg, 1.46 mmol), Pd₂(dba)₃ (44.7 mg, 0.05 mmol), BINAP (60.8 mg, 0.10 mmol) and Cs₂CO₃ (955.0 mg, 2.93 mmol) were dissolved in toluene/DMF (3.9 mL, 10/1, v/v), and stirred at 160° C. for 18 hours. After addition of H₂O, the reaction mixture was stirred and extracted with EtOAc. The organic layer was washed with brine, dried with Na₂SO₄, filtered and concentrated under reduced pressure. The residue was purified by C18 reversed-phase silica gel column chromatography (CH₃CN containing 0.1% formic acid:H₂O containing 0.1% formic acid) to obtain the yellow solid, N-(4-nitrophenethyl)furo[3,2-c]pyridin-4-amine (140.0 mg, 50.6%).

LC/MS ESI (+): 284 (M+1)

(b) Synthesis of N-(4-(2-(furo[3,2-c]pyridin-4-ylamino)ethyl)phenyl)methanesulfonamide N-(4-nitrophenethyl)furo[3,2-c]pyridin-4-amine (140.0 mg, 0.49 mmol) was dissolved in acetic acid (4.9 mL), and Zn (323 mg, 4.94 mmol) was added thereto at room temperature. The reaction mixture was stirred at room temperature for 1 hour and filtered with celite. After addition of H₂O, the reaction mixture was extracted with EtOAc, washed with brine, dried with Na₂SO₄, filtered and distilled under reduced pressure. The residue was dissolved in pyridine (4.9 mL), and MsCl (46.2 µL, 0.59 mmol) was slowly added thereto at 0° C. The reaction mixture was stirred at room temperature for 1 hour and filtered with celite. After addition of water, the reaction mixture was extracted with EtOAc, washed with brine, dried with Na₂SO₄, filtered and distilled under reduced pressure. The residue was purified by C18 reversed-phase silica gel column chromatography (CH₃CN:H₂O condition) and freeze-dried to obtain the white solid compound, N-(4-(2-(furo[3,2-c]pyridin-4-ylamino)ethyl)phenyl)methanesulfonamide (78.0 mg, 48%).

1H NMR (400 MHz, DMSO-d6) δ=9.53 (s, 1H), 7.80-7.77 (m, 1H), 7.74-7.72 (m, 1H), 7.18-7.11 (m, 2H), 7.09-7.04 (m, 2H), 7.04-7.00 (m, 1H), 7.00 (d, J=2.0 Hz, 1H), 6.73 (d, J=5.9 Hz, 1H), 3.61-3.49 (m, 2H), 2.87 (s, 3H), 2.80 (t, J=7.5 Hz, 2H)

LC/MS ESI (+): 332 (M+1)

Example 74: Synthesis of N-(4-(2-((4-chloroisoquinolin-1-yl)amino)ethyl)phenyl)methanesulfonamide

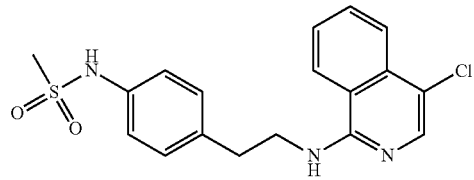 [SMILES: CS(=O)(=O)Nc1ccc(CCNc2ncc(Cl)c3ccccc23)cc1]

(a) Synthesis of 4-chloro-N-(4-nitrophenethyl)isoquinolin-1-amine 1,4-Dichloroisoquinoline (100.0 mg, 0.51 mmol), 2-(4-nitrophenyl)ethan-1-amine hydrochloride (124.0 mg, 0.51 mmol) and DIPEA (441.0 µL, 2.52 mmol) were dissolved in sulforane (5.0 mL) and stirred at 160° C. for 15 hours. After addition of H₂O, the reaction mixture was stirred and extracted with EtOAc. The organic layer was washed with brine, dried with Na₂SO₄, filtered and concentrated under reduced pressure. The residue was purified by C18 reversed-phase silica gel column chromatography (CH₃CN containing 0.1% formic acid:H₂O containing 0.1% formic acid) to obtain the yellow solid, 4-chloro-N-(4-nitrophenethyl)isoquinolin-1-amine (31.0 mg, 19%).

LC/MS ESI (+): 328 (M+1)

(b) Synthesis of N-(4-(2-((4-chloroisoquinolin-1-yl)amino)ethyl)phenyl)methanesulfonamide 4-Chloro-N-(4-nitrophenethyl)isoquinolin-1-amine (30.0 mg, 0.09 mmol) was dissolved in acetic acid (0.91 mL), and Zn (59.8 mg, 0.92 mmol) was added thereto at room temperature. The reaction mixture was stirred at room temperature for 1 hour and filtered with celite. After addition of H₂O, the reaction mixture was extracted with EtOAc, washed with brine, dried with Na₂SO₄, filtered and distilled under reduced pressure. The residue was dissolved in pyridine (4.9 mL), and MsCl (7.9 μL, 0.10 mmol) was slowly added thereto at 0° C. The reaction mixture was stirred at room temperature for 1 hour and filtered with celite. After addition of water, the reaction mixture was extracted with EtOAc, washed with brine, dried with Na₂SO₄, filtered and distilled under reduced pressure. The residue was purified by C18 reversed-phase silica gel column chromatography (CH₃CN:H₂O condition) and freeze-dried to obtain the white solid compound, N-(4-(2-((4-chloroisoquinolin-1-yl)amino)ethyl)phenyl)methanesulfonamide (24.0 mg, 70%).

1H NMR (400 MHz, DMSO-d6) δ=9.53 (br s, 1H), 8.23 (d, J=8.4 Hz, 1H), 7.92 (s, 1H), 7.87 (d, J=8.3 Hz, 1H), 7.77-7.73 (m, 1H), 7.73-7.67 (m, 1H), 7.55 (t, J=7.6 Hz, 1H), 7.19-7.13 (m, J=8.4 Hz, 2H), 7.09-7.04 (m, J=8.3 Hz, 2H), 3.65-3.56 (m, 2H), 2.87 (s, 3H), 2.86-2.83 (m, 2H)

LC/MS ESI (+): 376 (M+1)

Example 75: Synthesis of N-(4-(2-(isoquinolin-1-ylamino)ethyl)phenyl)methanesulfonamide

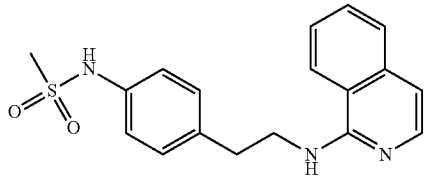 [SMILES: CS(=O)(=O)Nc1ccc(CCNc2nccc3ccccc23)cc1]

(a) Synthesis of N-(4-nitrophenethyl)isoquinolin-1-amine

1-Chloroisoquinoline (100 mg, 0.61 mmol), 2-(4-nitrophenyl)ethan-1-amine hydrochloride (124 mg, 0.61 mmol) and DIPEA (534 μL, 3.06 mmol) were dissolved in sulforane (6.0 mL) and stirred at 160° C. for 15 hours. After addition of H₂O, the reaction mixture was stirred and extracted with EtOAc. The organic layer was washed with brine, dried with Na₂SO₄, filtered and concentrated under reduced pressure. The residue was purified by C18 reversed-phase silica gel column chromatography (CH₃CN containing 0.1% formic acid:H₂O containing 0.1% formic acid) to obtain the yellow solid, N-(4-nitrophenethyl)isoquinolin-1-amine (32.0 mg, 17.8%).

LC/MS ESI (+): 294 (M+1)

1H NMR (400 MHz, CDCl3) δ=8.18 (d, J=8.7 Hz, 2H), 8.03 (d, J=5.9 Hz, 1H), 7.74-7.66 (m, 1H), 7.62 (m, 2H), 7.48-7.45 (dd, 7.8 Hz, 1.2 Hz, 1H), 7.43 (d, J=8.6 Hz, 2H), 6.99 (d, J=5.9 Hz, 1H), 5.26 (br s, 1H), 4.00-3.86 (m, 2H), 3.18 (t, J=6.9 Hz, 2H)

(b) Synthesis of N-(4-(2-(isoquinolin-1-ylamino)ethyl)phenyl)methanesulfonamide

N-(4-nitrophenethyl)isoquinolin-1-amine (31.0 mg, 0.11 mmol) was dissolved in acetic acid (1.0 mL), and Zn (69.1 mg, 1.06 mmol) was added thereto at 25° C. The reaction mixture was stirred at 25° C. for 2 hours and filtered with celite. After addition of H₂O, the reaction mixture was extracted with EtOAc, washed with brine, dried with Na₂SO₄, filtered and distilled under reduced pressure. The residue was dissolved in pyridine (1.0 mL), and MsCl (9.9 μL, 0.13 mmol) was slowly added thereto at 25° C. After the reaction was terminated, the reaction mixture was extracted with CH₂Cl₂. The organic layer was washed with brine, dried with Na₂SO₄, filtered and distilled under reduced pressure. The residue was purified by C18 reversed-phase silica gel column chromatography (CH₃CN containing 0.1% formic acid:H₂O containing 0.1% formic acid) to obtain the white solid compound, N-(4-(2-(isoquinolin-1-ylamino)ethyl)phenyl)methanesulfonamide (17.0 mg, 47.1%).

LC/MS ESI (+): 342 (M+1)

¹H NMR (300 MHz, DMSO-d₆) δ=9.59 (s, 1H), 8.21-8.17 (m, 1H), 7.88 (d, J=5.7 Hz, 1H), 7.72-7.66 (m, 1H), 7.61 (dt, J=1.0, 7.5 Hz, 1H), 7.50-7.48 (m, 1H), 7.48-7.44 (m, 1H), 7.27-7.21 (m, 2H), 7.17-7.09 (m, 2H), 6.88 (d, J=5.7 Hz, 1H), 3.72-3.64 (m, 2H), 2.94 (s, 3H), 2.93-2.89 (m, 2H)

Example 76: Synthesis of N-(4-(2-((2-methoxyquinolin-4-yl)amino)ethyl)phenyl)methanesulfonamide

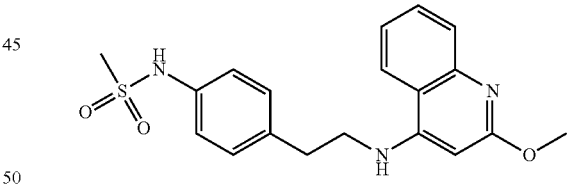

(a) Synthesis of 2-chloro-N-(4-nitrophenethyl)quinolin-4-amine 2,4-Dichloroquinoline (300.0 mg, 1.52 mmol), 2-(4-nitrophenyl)ethan-1-amine hydrochloride (307.0 mg, 1.52 mmol) and DIPEA (1.3 mL, 7.57 mmol) were dissolved in sulforane (7.5 mL) and stirred at 160° C. for 2 days. After addition of H₂O, the reaction mixture was stirred and extracted with EtOAc. The organic layer was washed with brine, dried with Na₂SO₄, filtered and distilled under reduced pressure. The residue was purified by C18 reversed-phase silica gel column chromatography (CH₃CN:H₂O condition) and freeze-dried to obtain the light brown solid compound, 2-chloro-N-(4-nitrophenethyl)quinolin-4-amine (130.0 mg, 25%).

¹H NMR (400 MHz, METHANOL-d₄) δ=8.17 (d, J=8.0 Hz, 2H), 8.00 (dd, J=0.7, 8.4 Hz, 1H), 7.74-7.69 (m, 1H), 7.69-7.63 (m, 1H), 7.52 (d, J=8.7 Hz, 2H), 7.45 (ddd, J=1.4, 6.8, 8.4 Hz, 1H), 6.51 (s, 1H), 3.70 (t, J=7.0 Hz, 2H), 3.17 (t, J=7.0 Hz, 2H)

LC/MS ESI (+): 328 (M+1)

(b) Synthesis of N-(4-(2-((2-chloroquinolin-4-yl) amino)ethyl)phenyl)methanesulfonamide 2-Chloro-N-(4-nitrophenethyl)quinolin-4-amine (130.0 mg, 0.40 mmol) was dissolved in acetic acid (4.0 mL), and Zn (259.0 mg, 3.97 mmol) was added thereto at room temperature. The reaction mixture was stirred at room temperature for 1 hour and filtered with celite. After addition of H₂O, the reaction mixture was extracted with EtOAc, washed with brine, dried with Na₂SO₄, filtered and distilled under reduced pressure. The residue was dissolved in pyridine (4.0 mL), and MsCl (34.0 μL, 0.44 mmol) was slowly added thereto at 0° C. The reaction mixture was stirred at room temperature for 1 hour and filtered with celite. After addition of H₂O, the reaction mixture was extracted with EtOAc, washed with brine, dried with Na₂SO₄, filtered and distilled under reduced pressure. The residue was purified by C18 reversed-phase silica gel column chromatography (CH₃CN:H₂O condition) and freeze-dried to obtain the white solid compound, N-(4-(2-((2-chloroquinolin-4-yl)amino)ethyl)phenyl)methanesulfonamide (100.0 mg, 67%).

¹H NMR (400 MHz, DMSO-d₆) δ=9.61 (s, 1H), 8.20 (d, J=8.3 Hz, 1H), 7.73-7.57 (m, 3H), 7.46 (t, J=7.0 Hz, 1H), 7.30-7.24 (m, J=8.4 Hz, 2H), 7.16-7.11 (m, J=8.4 Hz, 2H), 6.45 (s, 1H), 3.57-3.45 (m, 2H), 2.99-2.88 (m, 5H)

LC/MS ESI (+): 376 (M+1)

(c) Synthesis of N-(4-(2-((2-methoxyquinolin-4-yl) amino)ethyl)phenyl)methanesulfonamide N-(4-(2-((2-chloroquinolin-4-yl)amino)ethyl)phenyl)methanesulfonamide (20.0 mg, 2.66 mmol) was dissolved in methanol (1.0 mL), and sodium methoxide (144.0 mg, 2.66 mmol) was added thereto. The reaction mixture was stirred at 80° C. for 72 hours. After addition of sodium bicarbonate saturated solution, the reaction mixture was extracted with EtOAc, washed with brine, dried with Na₂SO₄, filtered and distilled under reduced pressure. The residue was purified by C18 reversed-phase silica gel column chromatography (CH₃CN:H₂O condition) and freeze-dried to obtain the white solid compound, N-(4-(2-((2-methoxyquinolin-4-yl)amino)ethyl)phenyl)methanesulfonamide (14.0 mg, 71%).

¹H NMR (400 MHz, DMSO-d₆) δ=9.61 (s, 1H), 8.06 (d, J=8.2 Hz, 1H), 7.60-7.57 (m, 1H), 7.55-7.50 (m, 1H), 7.29-7.24 (m, 3H), 7.14 (d, J=8.4 Hz, 2H), 7.09 (t, J=5.3 Hz, 1H), 5.89 (s, 1H), 3.88 (s, 3H), 3.48-3.40 (m, 2H), 2.94 (s, 3H), 2.93-2.90 (m, 2H)

LC/MS ESI (+): 372 (M+1)

EXPERIMENTAL EXAMPLES

With the compounds prepared in the Examples, the following experiments were carried out.

Cells and Reagents

Cancer cell lines used for evaluating the compounds of the Examples were purchased from ATCC (American Type Culture Collection) or KCLB (Korean Cell Line Bank), and cultured according to the vendor's recommendation. The human prostate cancer cell line stably expressing the STAT3 promoter (LNcaP stable cell line [plasmid STAT3-TA-luc])—which was prepared to evaluate the inhibitory effect of the compounds of the Examples against dimerization of STAT3—was cultured in RPMI1640 (Cat no. 11875, Gibco), 10% fetal bovine serum (Cat no. SH30071.03, Hyclone) and 150 μg/mL G418 solution (Cat no. 04 727 894 001, Roche).

In addition, to evaluate the inhibitory effect of the compounds of the Examples against dimerization of STAT1, total 12 g of luciferase reporter vector containing STAT1 response elements and b-galactosidase DNA at a ratio of 7:5 were transiently transfected into a human osteosarcoma cell line, and the experiment was carried out by the use of this cell line. The human osteosarcoma cell line was incubated in McCoy 5'A (Cat no. 16600, Gibco), 15% fetal bovine serum (Cat no. SH30071.03, Hyclone).

Information about experimental materials is as follows:
  rhIL-6 (Cat no. 206-IF, R&D system), rhIFN-γ (Cat no. 285-IF, R&D system), luciferase assay system (Cat no. E1501, Promega), pSTAT3-TA-luc (Cat no. PT-3535-5w, Takara bio), pGL4-STAT1-luc, pSV-β-Galactosidase control vector (Cat. #E1081, Promega), b-galactosidase enzyme assay sytem (Cat no. E2000, Promega), Jet-PEI transfection reagent (Cat no. 101-40, Polyplus) and Celltiter Glo luminescent cell viability assay (Cat no. G7573, Promega).

Experimental Example 1: STAT3 and STAT1 Activation Inhibition Experiment Via Reporter Gene Assay Experimental Example 1-1: STAT3 Activation Inhibition Assay The reporter gene assay of LNcap stable cell line was carried out by the use of RPMI 1640 medium containing 3% DCC-FBS (without G-418). The cell line was dispensed into two (2) white 96-well plates at 30,000 cells/well/50 μL. The cell line was incubated for 24 hours under the condition of 37° C. and 5% CO₂, and then the Example compounds of 50 mM DMSO stock were diluted to various concentrations and treated to two (2) white 96-well plates containing cells. Then, IL-6 was treated to a final concentration of 10 ng/mL. After the treatment of Example compounds and IL-6, the cells were cultured for 48 hours under the condition of 37° C. and 5% CO₂. After 48 hours, the 96-well plates were observed under a microscope to record the presence or absence of drug precipitation and specificities, and the 96-well plates were kept at room temperature for 30 minutes. Then, in the case of the first 96-well plate, the culture medium on the plate was removed to measure the luciferase activity, and treated with passive lysis buffer at 20 L/well and shaken for 30 minutes. The luciferase activity was measured on microLUMA LB96P (BERTHOLD) or Centro XS LB 960 (BERTHOLD) instrument using Luciferase assay system (Cat No. E1501, Promega Corporation). In the case of the second 96-well plate, 20 μL of Glo-mix solution was added to measure cytotoxicity by the compounds of the Examples, and the plate was well shaken for 10 minutes and analyzed on microLUMA LB96P (BERTHOLD) instrument using Glo-vial protocol. As a negative control, a 96 well-plate in which culture medium was added but cells were not plated was used. As a positive control, a 96 well-plate in which cells were plated and 0.1% DMSO and culture medium containing stimulation were added was used.

Experimental Example 1-2: STAT1 Activation Inhibition Assay

Human osteosarcoma U2OS cell line was plated with $2.0 \times 10^6$ cells/10 mL in a 100 mm² dish. After incubation under the condition of 37° C. and 5% $CO_2$ for 24 hours, total 12 µg of luciferase reporter vector containing STAT1 response elements and b-galactosidase DNA at a ratio of 7:5 were transfected by the use of a Jet-PEI transfection reagent. After incubation under the condition of 37° C. and 5% $CO_2$ for 4 hours, the transfected cell line was dispensed into a white 96-well plate at 25,000 cells/well/50 µL. After incubation under the condition of 37° C. and 5% $CO_2$ for 24 hours, the Example compounds of 50 mM DMSO stock were diluted to various concentrations and treated to the white 96-well plate containing cells. Then, IFN-g was treated to a final concentration of 50 ng/mL. After treatment of the Example compounds and IFN-g, the white 96-well plate was incubated under the condition of 37° C. and 5% $CO_2$ for 24 hours. After 24 hour incubation, the 96-well plate was observed under a microscope to record the presence or absence of drug precipitation and specificities, and the 96-well plate was kept at room temperature for 30 minutes. Then, the culture medium of the white 96-well plate was removed, and the plate was treated with MPER lysis buffer at 50 L/well and shaken for 30 minutes. Then, 30 L/well of the plate was taken and transferred to a new white 96-well plate. With this new white 96-well plate, the luciferase activity was measured on microLUMA LB96P (BERTHOLD) or Centro XS LB 960 (BERTHOLD) instrument using Luciferase assay system (Cat No. E1501, Promega Corporation). The remaining 20 L/well plate was measured with a UV detector (TECAN) at 405 nm using the b-galactosidase enzyme assay system to determine cytotoxicity by the Example compounds. As a negative control, a 96 well-plate in which culture medium was added but cells were not plated was used. As a positive control, a 96 well-plate in which cells were plated and 0.1% DMSO and culture medium containing stimulation were added was used.

The results of evaluating the inhibitory effects of the compounds of the Examples against dimerization of STAT3 and STAT1 via STAT3 and STAT1 reporter gene assay are represented in Table 1.

TABLE 1

| Example | $IC_{50}$ (µM) pSTAT3 | $IC_{50}$ (µM) pSTAT1 | Example | $IC_{50}$ (µM) pSTAT3 | $IC_{50}$ (µM) pSTAT1 |
|---|---|---|---|---|---|
| 1 | 2.6 | >50 | 2 | 0.85 | >50 |
| 3 | 10.5 | >50 | 4 | 20.9 | 40.9 |
| 5 | 38.1 | 46.2 | 6 | 0.71 | >50 |
| 7 | 0.038 | >50 | 8 | 7.8 | 46.4 |
| 9 | 3.0 | >50 | 10 | 3.9 | >50 |
| 11 | 1.6 | >50 | 12 | 5.8 | >50 |
| 13 | 3.1 | >50 | 14 | 0.59 | >50 |
| 15 | 3.1 | 46.1 | 16 | >50 | >50 |
| 17 | 1.6 | >50 | 18 | 0.21 | >50 |
| 19 | >50 | >50 | 20 | 0.75 | >50 |
| 21 | 2.3 | >50 | 22 | 0.10 | >50 |
| 23 | 0.26 | >50 | 24 | 4.1 | >50 |
| 25 | 1.9 | >50 | 26 | 0.15 | >50 |
| 27 | 0.14 | >50 | 28 | 32.3 | >50 |
| 29 | 0.64 | >50 | 30 | 2.2 | >50 |
| 31 | 0.12 | >50 | 32 | 3.3 | 45.2 |
| 33 | 6.0 | >50 | 34 | 6.9 | >50 |
| 35 | 2.3 | >50 | 36 | 0.023 | >50 |
| 37 | 20.3 | >50 | 38 | 0.17 | >50 |
| 39 | >50 | >50 | 40 | >50 | >50 |
| 41 | 9.8 | >50 | 42 | >50 | >50 |
| 43 | >50 | >50 | 44 | >50 | >50 |
| 45 | 13.1 | 50 | 46 | 33.7 | >50 |
| 47 | >50 | >50 | 48 | 7.3 | >50 |
| 49 | 5.6 | >50 | 50 | 13.9 | >50 |
| 51 | 24.1 | >50 | 52 | 3.1 | 47.4 |
| 53 | 3.0 | >50 | 54 | 11.0 | >50 |
| 55 | >50 | >50 | 56 | 6.6 | 28.9 |
| 57 | 17.9 | >50 | 58 | >50 | >50 |
| 59 | 0.35 | >50 | 60 | 14.0 | 33.9 |
| 61 | 0.053 | >50 | 62 | 12.1 | 41.8 |
| 63 | 0.75 | >50 | 64 | 0.063 | >50 |
| 65 | >50 | >50 | 66 | 0.74 | >50 |
| 67 | 4.4 | >50 | 68 | 0.076 | >50 |
| 69 | 0.046 | >50 | 70 | 3.8 | >50 |
| 71 | 9.6 | >50 | 72 | 0.62 | >50 |
| 73 | 35.9 | >50 | 74 | 3.9 | >50 |
| 75 | 4.3 | >50 | 76 | 1.2 | >50 |

Experimental Example 2: Cell Growth Inhibition Assay

Cancer cell inhibitory effects by the compounds of the Examples were evaluated as follows. The prostate cancer cell line (LNCap) used was cultured under the condition according to the vendor's recommendation. LNCap was dispensed into a 96-well plate at 10,000 cells/well. After incubation under the condition of 37° C. and 5% $CO_2$ for 24 hours, the Example compounds of 50 mM DMSO stock were diluted to various concentrations and treated to the 96-well plate containing cells. After treatment of the Example compounds, LNCap cells were incubated in an incubator (37° C., 5% $CO_2$) for 120 hours. After each incubation time, the 96-well plate was observed under a microscope to record the presence or absence of drug precipitation and specificities, and the 96-well plate was kept at room temperature for 30 minutes. Then, after addition of 20 µL of Celltiter Glo solution, the 96-well plate was well shaken for 30 minutes. The growth inhibitory activity was measured on microLUMA LB96P (BERTHOLD) instrument using Glo-vial protocol. As a negative control, a 96 well-plate in which culture medium was added but cells were not plated was used. As a positive control, a 96 well-plate in which cells were plated and 0.1% DMSO instead of drugs was added was used. The results of growth inhibitory effects of the Example compounds on prostate cancer cell line are represented in Table 2.

TABLE 2

| Example | $IC_{50}$ (µM) LNCap | Example | $IC_{50}$ (µM) LNCap | Example | $IC_{50}$ (µM) LNCap | Example | $IC_{50}$ (µM) LNCap |
|---|---|---|---|---|---|---|---|
| 1 | 3.5 | 2 | 0.81 | 3 | 5.1 | 4 | >50 |
| 5 | 47.3 | 6 | 0.69 | 7 | 0.078 | 8 | 16.0 |
| 9 | 7.7 | 10 | 2.6 | 11 | 2.6 | 12 | 9.3 |
| 13 | 2.5 | 14 | 1.9 | 15 | 1.6 | 16 | 21.8 |
| 17 | 4.7 | 18 | 0.48 | 19 | 18.4 | 20 | 0.74 |
| 21 | 2.4 | 22 | 0.074 | 23 | 0.25 | 24 | 6.2 |
| 25 | 9.6 | 26 | 0.23 | 27 | 0.14 | 28 | 44.1 |
| 29 | 2.5 | 30 | 7.0 | 31 | 0.21 | 32 | 33.8 |
| 33 | >50 | 34 | 15.7 | 35 | 7.3 | 36 | 0.093 |
| 37 | 10.6 | 38 | 0.18 | 39 | >50 | 40 | >50 |
| 41 | >50 | 42 | >50 | 43 | >50 | 44 | >50 |
| 45 | 13.1 | 46 | 18.9 | 47 | >50 | 48 | 14.2 |
| 49 | 14.1 | 50 | 23.1 | 51 | 27.7 | 52 | 6.6 |
| 53 | 15.7 | 54 | 14.1 | 55 | >50 | 56 | 13.9 |
| 57 | 8.6 | 58 | >50 | 59 | 0.16 | 60 | 29.5 |
| 61 | 0.19 | 62 | 23.5 | 63 | 1.9 | 64 | 0.23 |
| 65 | >50 | 66 | 0.71 | 67 | 3.7 | 68 | 0.27 |
| 69 | 0.13 | 70 | 10.8 | 71 | 20.9 | 72 | 1.4 |
| 73 | 33.0 | 74 | 13.1 | 75 | 6.0 | 76 | 3.9 |

The invention claimed is:
1. A compound of the following Formula 1, or a pharmaceutically acceptable salt thereof:

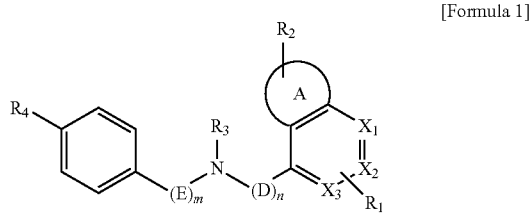

[Formula 1]

wherein
each of $X_1$, $X_2$ and $X_3$ is independently C or N, provided that at least one of $X_1$, $X_2$ and $X_3$ is N;
$R_1$ is hydrogen, halo, alkyl, haloalkyl, alkoxy or alkylamino;
$R_2$ is hydrogen, hydroxy, halo, carboxy, —C(=O)—NH—NH$_2$, alkyl, alkoxy, haloalkoxy, alkoxy-carbonyl, carboxy-alkoxy, aminocarbonyl-alkoxy, alkoxy-carbonyl-alkoxy, aryl, aryl-oxy, aryl-alkyl-aminosulfonyl, aryl-carbonyl, aminocarbonyl, 5- to 8-membered heterocycloalkyl or 5- to 8-membered heterocycloalkyl-carbonyl, wherein the heterocycloalkyl has 1 to 3 heteroatoms selected from N, O and S, and the aryl is optionally substituted with nitro or halo;
$R_3$ is hydrogen or aryl-alkyl;
$R_4$ is nitro, nitroso, amino, alkylsulfonyl-amino, alkylsulfonylhydroxyamino(-N(OH)S(O$_2$)alkyl) or haloalkylsulfonyl-amino; provided that when $R_1$ is alkyl, $R_4$ is not alkylsulfonyl-amino; and when $R_1$ is hydrogen or methyl, $R_4$ is not amino or nitro;
A ring is aryl or 3- to 8-membered saturated or unsaturated heterocycle having 1 to 3 heteroatoms selected from N, O and S;
D is —CH$_2$—;
E is —CH$_2$— optionally substituted with halo;
n is an integer of 0 to 2; and
m is an integer of 2 to 4;
provided that when $X_1$ and $X_3$ are N, $X_2$ is C, and $R_1$ is hydrogen; n is 0, m is 2, $R_2$ is hydrogen or aryl substituted with halo, and $R_4$ is nitro, alkylsulfonyl-amino or haloalkylsulfonyl-amino,
provided that the compound of Formula 1 is not 2-methyl-N-(4-nitrophenethyl)quinoline-4-amine, N-[2-(4-nitrophenyl)ethyl]thieno[2,3-d]pyrimidin-4-amine, or N-[2-(4-nitrophenyl)ethyl]thieno[3,2-d]pyrimidin-4-amine; and
provided that A ring is not 5-membered unsaturated heterocycle having 2 nitrogen atoms.
2. The compound, or a pharmaceutically acceptable salt thereof according to claim 1, wherein
each of $X_1$, $X_2$ and $X_3$ is independently C or N, provided that at least one of $X_1$, $X_2$ and $X_3$ is N;
$R_1$ is hydrogen, halo, $C_1$-$C_6$-alkyl, halo-$C_1$-$C_6$-alkyl, $C_1$-$C_6$ alkoxy or $C_1$-$C_6$-alkylamino;
$R_2$ is hydrogen, hydroxy, halo, carboxy, —C(=O)—NH—NH$_2$, $C_1$-$C_6$-alkyl, $C_1$-$C_6$-alkoxy, halo-$C_1$-$C_6$-alkoxy, $C_1$-$C_6$-alkoxy-carbonyl, carboxy-$C_1$-$C_6$-alkoxy, aminocarbonyl-$C_1$-$C_6$-alkoxy, $C_1$-$C_6$-alkoxy-carbonyl-$C_1$-$C_6$-alkoxy, $C_6$-$C_{10}$-aryl, $C_6$-$C_{10}$-aryl-oxy, $C_6$-$C_{10}$-aryl-$C_1$-$C_6$-alkyl-aminosulfonyl, $C_6$-$C_{10}$-aryl-carbonyl, aminocarbonyl, 5- to 8-membered heterocycloalkyl or 5- to 8-membered heterocycloalkylcarbonyl, wherein the heterocycloalkyl has 1 to 3 heteroatoms selected from N, O and S, and the aryl is optionally substituted with nitro or halo;
$R_3$ is hydrogen or $C_6$-$C_{10}$-aryl-$C_1$-$C_6$-alkyl;
$R_4$ is nitro, nitroso, amino, $C_1$-$C_6$-alkylsulfonyl-amino, $C_1$-$C_6$-alkylsulfonylhydroxyamino or halo-$C_1$-$C_6$-alkylsulfonyl-amino; provided that when $R_1$ is $C_1$-$C_6$-alkyl, $R_4$ is not $C_1$-$C_6$-alkylsulfonyl-amino; and when $R_1$ is hydrogen or methyl, $R_4$ is not amino or nitro;
A ring is $C_6$-$C_{10}$-aryl or 5- or 6-membered saturated or unsaturated heterocycle having 1 to 3 heteroatoms selected from N, O and S;
D is —CH$_2$—;
E is —CH$_2$— optionally substituted with halo;
n is an integer of 0 to 2; and
m is an integer of 2 to 4;
provided that when $X_1$ and $X_3$ are N, $X_2$ is C, and $R_1$ is hydrogen; n is 0, m is 2, $R_2$ is hydrogen or $C_6$-$C_{10}$-aryl substituted with halo, and $R_4$ is nitro, $C_1$-$C_6$-alkylsulfonyl-amino or halo-$C_1$-$C_6$-alkylsulfonyl-amino.
3. The compound, or a pharmaceutically acceptable salt thereof according to claim 1, wherein $X_1$ is N, and each of $X_2$ and $X_3$ is independently C or N.
4. The compound, or a pharmaceutically acceptable salt thereof according to claim 1, wherein $R_1$ is halo, $C_1$-$C_6$-alkyl, halo-$C_1$-$C_4$-alkyl, $C_1$-$C_4$ alkoxy or $C_1$-$C_4$-alkylamino.
5. The compound, or a pharmaceutically acceptable salt thereof according to claim 1, wherein $R_2$ is hydrogen, hydroxy, halo, carboxy, —C(=O)—NH—NH$_2$, $C_1$-$C_4$-alkyl, $C_1$-$C_4$-alkoxy, halo-$C_1$-$C_4$-alkoxy, $C_1$-$C_4$-alkoxy-carbonyl, carboxy-$C_1$-$C_4$-alkoxy, aminocarbonyl-$C_1$-$C_4$-alkoxy, $C_1$-$C_4$-alkoxy-carbonyl-$C_1$-$C_4$-alkoxy, phenyl, phenoxy, phenyl-$C_1$-$C_4$-alkyl-aminosulfonyl, phenyl-carbonyl, aminocarbonyl, 5- or 6-membered heterocycloalkyl, or 5- or 6-membered heterocycloalkylcarbonyl, wherein the heterocycloalkyl has 1 to 3 heteroatoms selected from N, O and S, and the phenyl is optionally substituted with nitro or halo.
6. The compound, or a pharmaceutically acceptable salt thereof according to claim 1, wherein $R_3$ is hydrogen or phenyl-$C_1$-$C_4$-alkyl.
7. The compound, or a pharmaceutically acceptable salt thereof according to claim 1, wherein $R_4$ is nitro, nitroso, amino, $C_1$-$C_4$-alkylsulfonyl-amino, $C_1$-$C_4$-alkylsulfonylhydroxyamino or halo-$C_1$-$C_4$-alkylsulfonyl-amino.
8. The compound, or a pharmaceutically acceptable salt thereof according to claim 1, wherein A ring is phenyl or 5- or 6-membered unsaturated heterocycle having 1 to 3 heteroatoms selected from N and S.
9. A compound selected from the group consisting of:
2-chloro-N-(4-nitrophenethyl)quinolin-4-amine;
N-(4-(2-((2-chloroquinolin-4-yl)amino)ethyl)phenyl)-N-hydroxymethanesulfonamide;
4-(2-((2-chloroquinolin-4-yl)amino)ethyl)benzenesulfonamide;
4-(2-((2-chloroquinolin-4-yl)(phenethyl)amino)ethyl) benzenesulfonamide;
2-methyl-N-(4-nitrophenethyl)quinolin-4-amine;
N-(4-(2-((2-chloroquinolin-4-yl)amino)ethyl)phenyl) methanesulfonamide;
2-chloro-8-ethyl-N-(4-nitrophenethyl)quinolin-4-amine;
2-chloro-6-methoxy-N-(4-nitrophenethyl)quinolin-4-amine;
2-chloro-8-methoxy-N-(4-nitrophenethyl)quinolin-4-amine;
N-(4-(2-((2-chloro-6-methoxyquinolin-4-yl)amino)ethyl) phenyl)methanesulfonamide;
2-chloro-N-(4-nitrophenethyl)-7-(trifluoromethoxy)quinolin-4-amine;

2-chloro-N-(4-nitrophenethyl)-5-(trifluoromethoxy)quinolin-4-amine;
2-chloro-6-fluoro-N-(4-nitrophenethyl)quinolin-4-amine;
2-chloro-8-methyl-N-(4-nitrophenethyl)quinolin-4-amine;
ethyl 2-chloro-4-((4-nitrophenethyl)amino)quinolin-6-carboxylate;
N-(4-nitrophenethyl)quinolin-4-amine;
2-chloro-N-(4-nitrophenethyl)quinazolin-4-amine;
2-chloro-N-(4-nitrophenethyl)-4-((4-nitrophenethyl)amino)quinolin-6-sulfonamide;
2-chloro-N-(4-nitrosophenethyl)quinolin-4-amine;
N-(4-(2-((6-fluoroquinolin-4-yl)amino)ethyl)phenyl)methanesulfonamide;
N-(4-(2-((2-chloro-6-fluoroquinolin-4-yl)amino)ethyl)phenyl)methanesulfonamide;
N-(4-(2-((2-chloroquinazolin-4-yl)amino)ethyl)phenyl)methanesulfonamide;
N-(4-(2-((2-chloro-7-(trifluoromethoxy)quinolin-4-yl)amino)ethyl)phenyl)methanesulfonamide;
N-(4-(2-((7-(trifluoromethoxy)quinolin-4-yl)amino)ethyl)phenyl)methanesulfonamide;
N-(4-(2-((2-chloro-5-(trifluoromethoxy)quinolin-4-yl)amino)ethyl)phenyl)methanesulfonamide;
N-(4-(2-((5-(trifluoromethoxy)quinolin-4-yl)amino)ethyl)phenyl)methanesulfonamide;
2-chloro-6-morpholino-N-(4-nitrophenethyl)quinolin-4-amine 2,2,2-trifluoroacetate;
2-chloro-5-fluoro-N-(4-nitrophenethyl)quinolin-4-amine;
2-chloro-7-fluoro-N-(4-nitrophenethyl)quinolin-4-amine;
2-chloro-8-fluoro-N-(4-nitrophenethyl)quinolin-4-amine;
2,6-dichloro-N-(4-nitrophenethyl)quinolin-4-amine;
2-chloro-N-(4-nitrophenethyl)-6-phenoxyquinolin-4-amine;
(2-chloro-4-((4-nitrophenethyl)amino)quinolin-6-yl)(phenyl)methanone:
2-chloro-4-((4-nitrophenethyl)amino)quinolin-6-ol;
N-(4-nitrophenethyl)quinazolin-4-amine;
ethyl 2-((2-chloro-4-((4-nitrophenethyl)amino)quinolin-6-yl)oxy)acetate;
N-(4-(2-(quinazolin-4-ylamino)ethyl)phenyl)methanesulfonamide;
2-((2-chloro-4-((4-nitrophenethyl)amino)quinolin-6-yl)oxy)acetamide;
2-chloro-4-((4-nitrophenethyl)amino)quinolin-6-carboxylic acid;
2-chloro-4-((4-nitrophenethyl)amino)quinolin-6-carboxamide;
(2-chloro-4-((4-nitrophenethyl)amino)quinolin-6-yl)(morpholino)methanone;
2-((2-chloro-4-((4-nitrophenethyl)amino)quinolin-6-yl)oxy)acetic acid;
2-chloro-4-((4-nitrophenethyl)amino)quinolin-6-carbohydrazide;
N-(4-(2-((2-chloro-8-fluoroquinolin-4-yl)amino)ethyl)phenyl)methanesulfonamide;
N-(4-(2-((8-fluoroquinolin-4-yl)amino)ethyl)phenyl)methanesulfonamide;
2-chloro-N-(4-nitrophenethyl)-9H-purin-6-amine;
N-(4-nitrophenethyl)-2-(trifluoromethyl)quinazolin-4-amine;
N-(4-nitrophenethyl)-2-(trifluoromethyl)quinolin-4-amine;
2-fluoro-N-(4-nitrophenethyl)-9H-purin-6-amine;
$N^2$-methyl-$N^4$-(4-nitrophenethyl)quinolin-2,4-diamine 2,2,2-trifluoroacetate;
N-(4-(2-((2-(trifluoromethyl)quinolin-4-yl)amino)ethyl)phenyl)methanesulfonamide;
N-(4-(2-((2-(trifluoromethyl)quinazolin-4-yl)amino)ethyl)phenyl)methanesulfonamide;
6-(2,4-dichlorophenyl)-N-(4-nitrophenethyl)quinazolin-4-amine;
2-chloro-6-(2,4-dichlorophenyl)-N-(4-nitrophenethyl)quinolin-4-amine;
N-(4-(2-((6-(2,4-dichlorophenyl)quinazolin-4-yl)amino)ethyl)phenyl)methanesulfonamide;
N-(4-(2-((2-chloro-6-(2,4-dichlorophenyl)quinolin-4-yl)amino)ethyl)phenyl)methanesulfonamide;
2-chloro-N-(4-(methylsulfonamido)benzyl)quinolin-4-carboxamide;
N-(2,2-difluoro-2-(4-nitrophenyl)ethyl)quinazolin-4-amine;
1,1,1-trifluoro-N-(4-(2-(quinazolin-4-ylamino)ethyl)phenyl)methanesulfonamide;
N-(4-nitrophenethyl) isoquinolin-4-amine;
N-(4-(2-(isoquinolin-4-ylamino)ethyl)phenyl)methanesulfonamide;
2-(4-nitrophenyl)-N-(quinazolin-4-yl)acetamide;
N-(4-(2-(thieno[3,2-d]pyrimidin-4-ylamino)ethyl)phenyl)methanesulfonamide;
2-chloro-N-(4-nitrophenethyl)pyrido[2,3-d]pyrimidin-4-amine;
N-(4-(2-(thieno[2,3-d]pyrimidin-4-ylamino)ethyl)phenyl)methanesulfonamide;
N-(4-(2-(thiazolo[5,4-d]pyrimidin-7-ylamino)ethyl)phenyl)methanesulfonamide;
N-(4-(2-((7H-pyrrolo[2,3-d]pyrimidin-4-yl)amino)ethyl)phenyl)methanesulfonamide;
N-(4-(2-(pyrido[3,4-b]pyrazin-5-ylamino)ethyl)phenyl)methanesulfonamide;
N-(4-(2-((3-methylquinolin-4-yl)amino)ethyl)phenyl)methanesulfonamide;
N-(4-(2-(furo[3,2-c]pyridin-4-ylamino)ethyl)phenyl)methanesulfonamide;
N-(4-(2-((4-chloroisoquinolin-1-yl)amino)ethyl)phenyl)methanesulfonamide;
N-(4-(2-(isoquinolin-1-ylamino)ethyl)phenyl)methanesulfonamide; and
N-(4-(2-((2-methoxyquinolin-4-yl)amino)ethyl)phenyl)methanesulfonamide,
or a pharmaceutically acceptable salt thereof.

10. A pharmaceutical composition comprising a compound, or a pharmaceutically acceptable salt thereof as defined in claim 1 as an active ingredient, and a pharmaceutically acceptable carrier.

11. The pharmaceutical composition according to claim 10, which is for the treatment of a disease associated with the activation of STAT3 protein.

12. The pharmaceutical composition according to claim 11, wherein the disease associated with the activation of STAT3 protein is selected from the group consisting of solid tumor, blood cancer, radiation or drug-resistant cancer, metastatic cancer, inflammatory disease, immune system disease, diabetes, macular degeneration, papillomavirus infection and tuberculosis.

13. The pharmaceutical composition according to claim 11, wherein the disease associated with the activation of STAT3 protein is selected from the group consisting of breast cancer, lung cancer, stomach cancer, prostate cancer, uterine cancer, ovarian cancer, renal cancer, pancreatic cancer, liver cancer, colon cancer, skin cancer, head and neck cancer, thyroid cancer, osteosarcoma, acute or chronic leukemia, multiple myeloma, non-Hodgkin's lymphoma, autoimmune diseases, psoriasis, hepatitis, inflammatory bowel disease, Crohn's disease, diabetes, macular degeneration, papillomavirus infection and tuberculosis.

14. A pharmaceutical composition comprising a compound, or a pharmaceutically acceptable salt thereof as defined in claim 9 as an active ingredient, and a pharmaceutically acceptable carrier.

15. The pharmaceutical composition according to claim 14, which is for the treatment of a disease associated with the activation of STAT3 protein.

16. The pharmaceutical composition according to claim 15, wherein the disease associated with the activation of STAT3 protein is selected from the group consisting of solid tumor, blood cancer, radiation or drug-resistant cancer, metastatic cancer, inflammatory disease, immune system disease, diabetes, macular degeneration, papillomavirus infection and tuberculosis.

17. The pharmaceutical composition according to claim 15, wherein the disease associated with the activation of STAT3 protein is selected from the group consisting of breast cancer, lung cancer, stomach cancer, prostate cancer, uterine cancer, ovarian cancer, renal cancer, pancreatic cancer, liver cancer, colon cancer, skin cancer, head and neck cancer, thyroid cancer, osteosarcoma, acute or chronic leukemia, multiple myeloma, non-Hodgkin's lymphoma, autoimmune diseases, psoriasis, hepatitis, inflammatory bowel disease, Crohn's disease, diabetes, macular degeneration, papillomavirus infection and tuberculosis.

* * * * *